(12) United States Patent
Goldstein et al.

(10) Patent No.: US 8,956,571 B2
(45) Date of Patent: Feb. 17, 2015

(54) CARBON MONOXIDE SENSOR SYSTEM AND RELATED METHODS

(71) Applicant: Quantum Group, Inc., San Diego, CA (US)

(72) Inventors: Mark K. Goldstein, Del Mar, CA (US); Michelle S. Oum, Chula Vista, CA (US)

(73) Assignee: Quantum Group Inc., San Diego, CA (US)

( * ) Notice: Subject to any disclaimer, the term of this patent is extended or adjusted under 35 U.S.C. 154(b) by 122 days.

(21) Appl. No.: 13/657,776

(22) Filed: Oct. 22, 2012

(65) Prior Publication Data

US 2013/0071290 A1 Mar. 21, 2013

Related U.S. Application Data

(63) Continuation-in-part of application No. 13/037,094, filed on Feb. 28, 2011, now abandoned, and a continuation-in-part of application No. 13/565,327, filed on Aug. 2, 2012, which is a continuation of (Continued)

(51) Int. Cl.
*G01N 21/00* (2006.01)
*G01N 21/01* (2006.01)
(Continued)

(52) U.S. Cl.
CPC .............. *G01N 21/783* (2013.01); *G01N 31/22* (2013.01); *B82Y 30/00* (2013.01); *G01N 21/53* (2013.01)
USPC .............. 422/91; 422/83; 422/88; 422/400; 422/401; 422/402; 73/23.2; 73/23.21; 73/23.31; 73/31.02; 73/31.05

(58) Field of Classification Search
USPC .............. 73/23.2, 23.21, 23.31, 31.01–31.05; 422/50, 400–404, 420, 421, 424–426, 422/429, 83, 88, 91
See application file for complete search history.

(56) References Cited

U.S. PATENT DOCUMENTS 4,043,934 A 8/1977 Shuler et al.
4,059,658 A 11/1977 Shoup et al.
(Continued)

FOREIGN PATENT DOCUMENTS

WO WO 88/05911 8/1988

OTHER PUBLICATIONS

U.S. Appl. No. 10/997,646, filed Nov. 24, 2004, Goldstein et al.
(Continued)

*Primary Examiner* — In Suk Bullock
*Assistant Examiner* — Robert Eom
(74) *Attorney, Agent, or Firm* — Christie, Parker & Hale, LLP

(57) ABSTRACT

A miniature lower cost optical sensing apparatus and method are provided for determining the concentration and/or hazard from a target gas by means of IR or visible photon monitoring one or more sensors that responds to carbon monoxide. The apparatus comprises a photon source optically coupled to the sensor and at least a portion of the photon intensity passing through the sensor is quantified by one or more photodiode(s) in a system, so that the photon flux is a function of at least one sensor's response to the target gas, e.g., transmits light through the sensor to the photodiode. The photo current from the photodiode is converted to a sensor reading value proportional to the optical characteristics of the sensors and is loaded into a microprocessor or other logic circuit. In the microprocessor, the sensor readings may be differentiated to determine the rate of change of the sensor readings and the total photons absorbed value may be used to calculate the CO concentration and/or dose.

35 Claims, 44 Drawing Sheets

Related U.S. Application Data application No. 13/037,094, filed on Feb. 28, 2011, now abandoned, which is a continuation of application No. 11/786,883, filed on Apr. 13, 2007, now abandoned.

(60) Provisional application No. 60/792,103, filed on Apr. 13, 2006.

(51) Int. Cl.
*G01N 21/53* (2006.01)
*G01N 21/75* (2006.01)
*G01N 21/78* (2006.01)
*G01N 31/22* (2006.01)
*B82Y 30/00* (2011.01)

(56) References Cited

U.S. PATENT DOCUMENTS

| | | | |
|---|---|---|---|
| 4,221,578 | A | 9/1980 | Shoup et al. |
| 4,803,052 | A * | 2/1989 | Abromaitis et al. ............ 422/91 |
| 5,063,164 | A | 11/1991 | Goldstein |
| 5,618,493 | A | 4/1997 | Goldstein et al. |
| 6,251,344 | B1 | 6/2001 | Goldstein |
| 6,429,019 | B1 | 8/2002 | Goldstein et al. |
| 2007/0192041 | A1 | 8/2007 | Goldstein et al. |
| 2008/0317636 | A1 * | 12/2008 | Brahim et al. ................. 422/98 |
| 2009/0043515 | A1 | 2/2009 | Goldstein et al. |

OTHER PUBLICATIONS

U.S. Appl. No. 60/711,748, filed Aug. 25, 2005, Gonzales et al.

\* cited by examiner

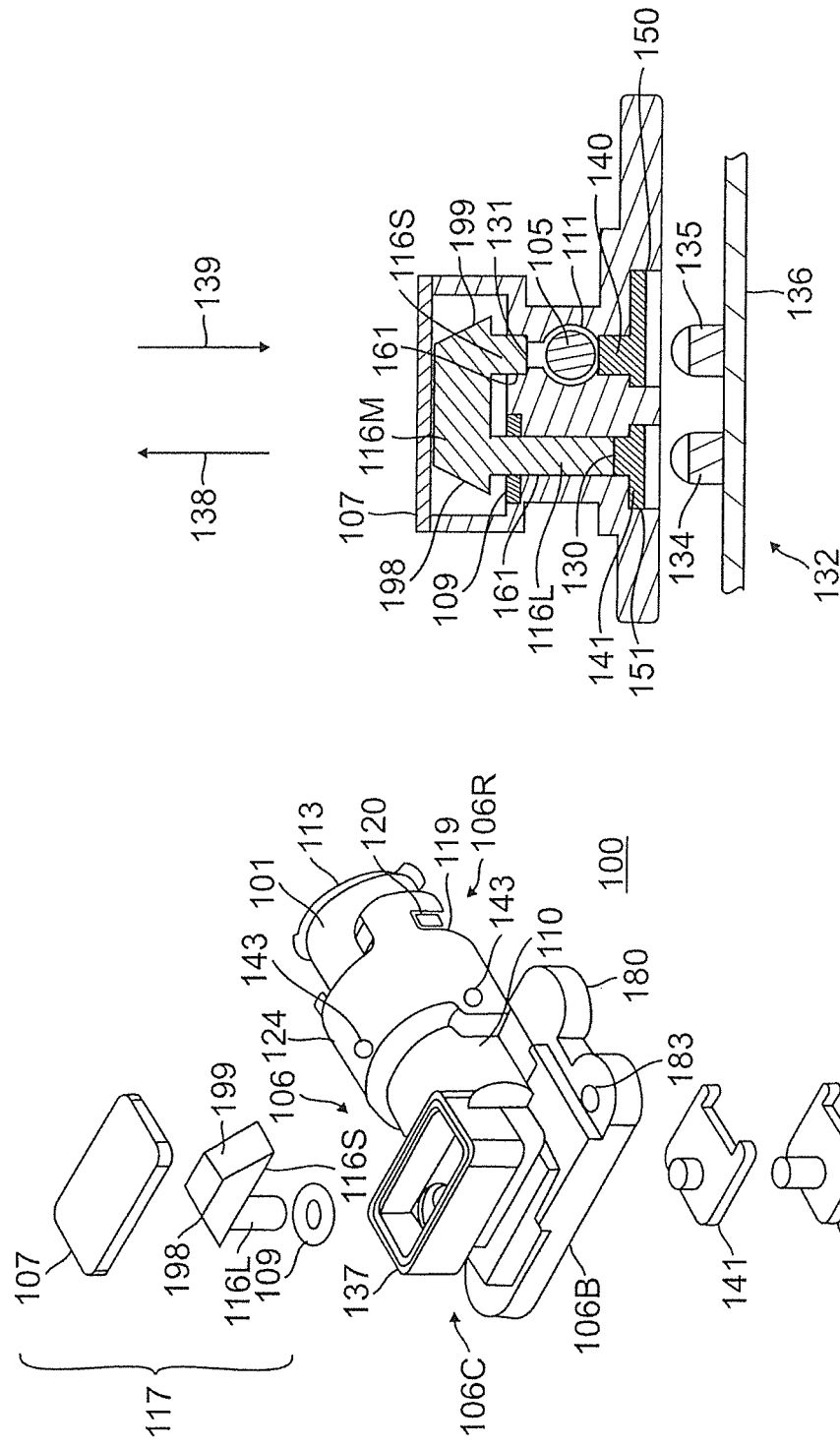

FIG. 5     SIR SYSTEM 300

FIG. 6  SIR SYSTEM 400

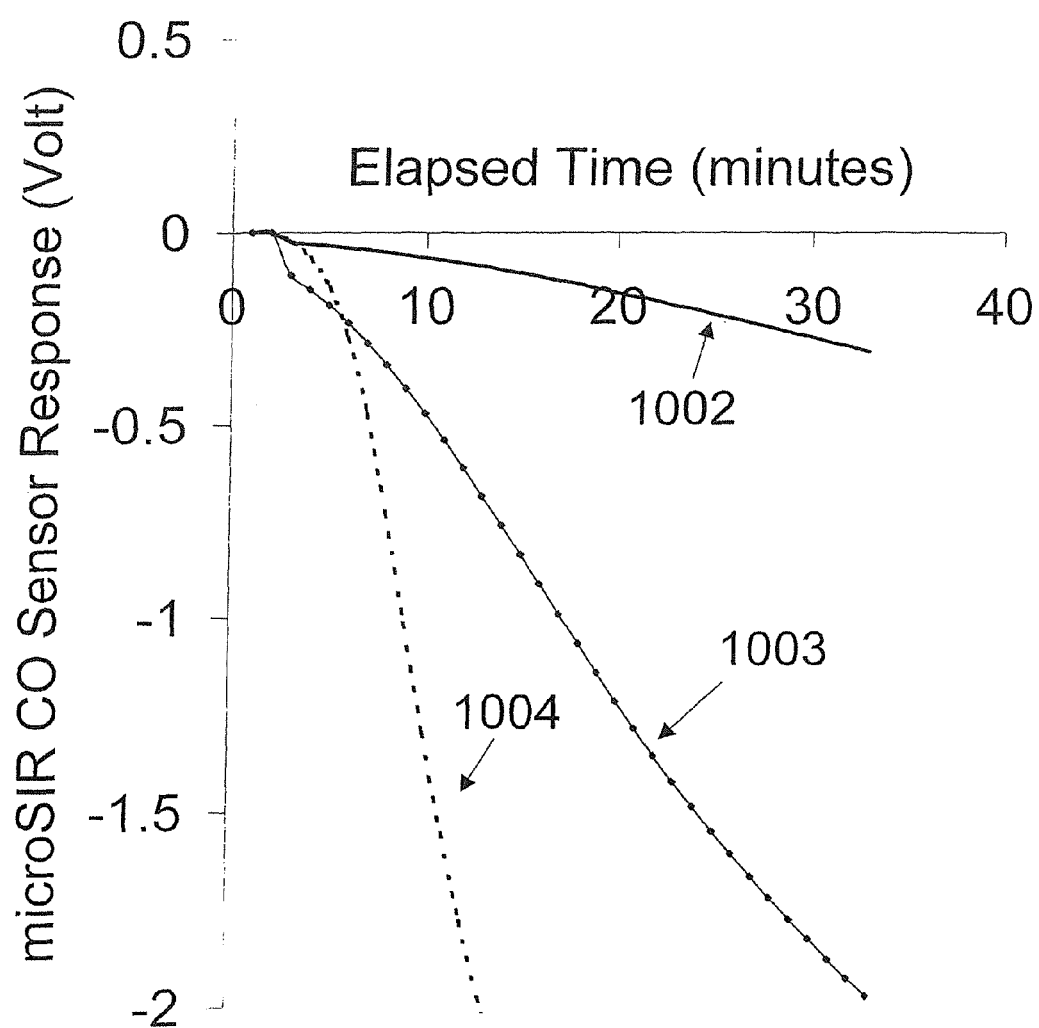

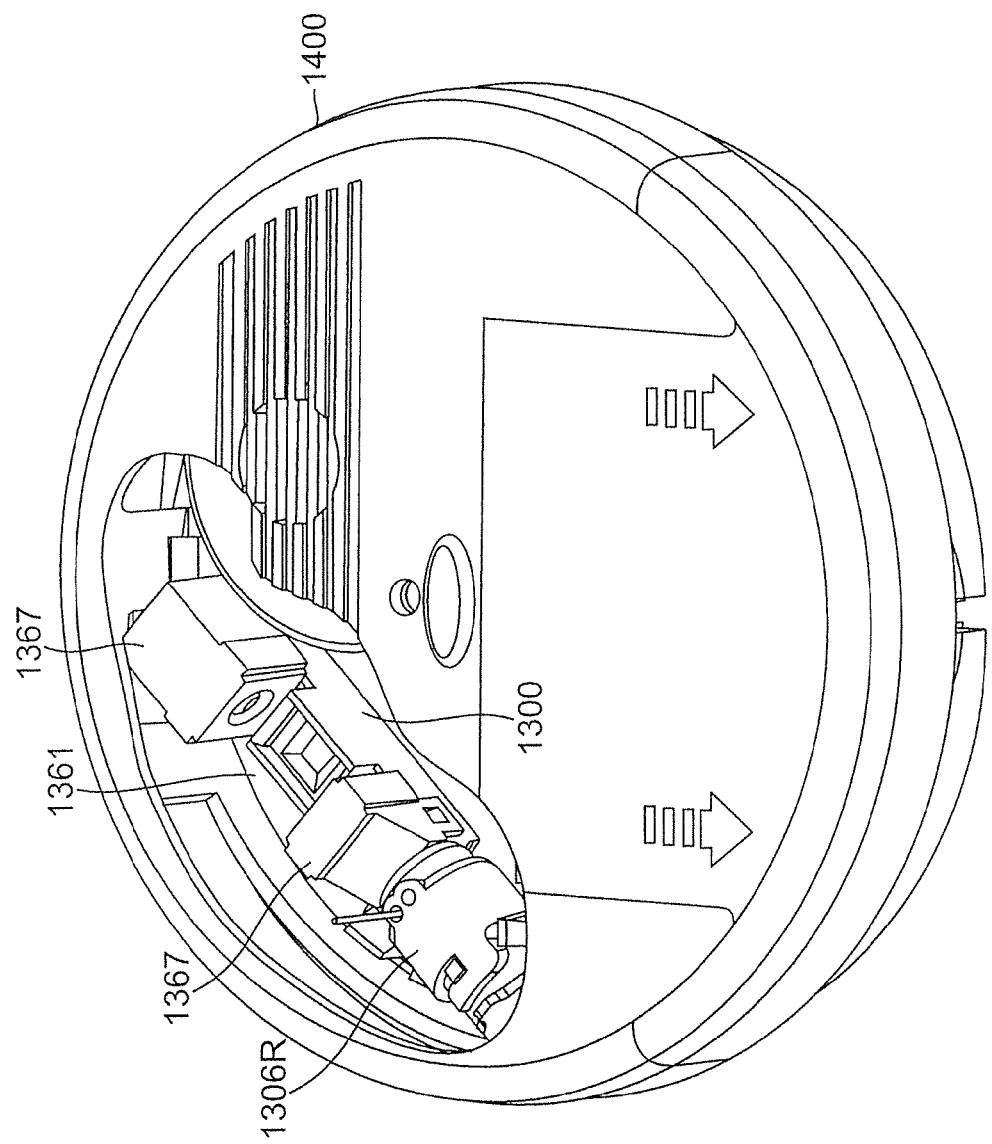

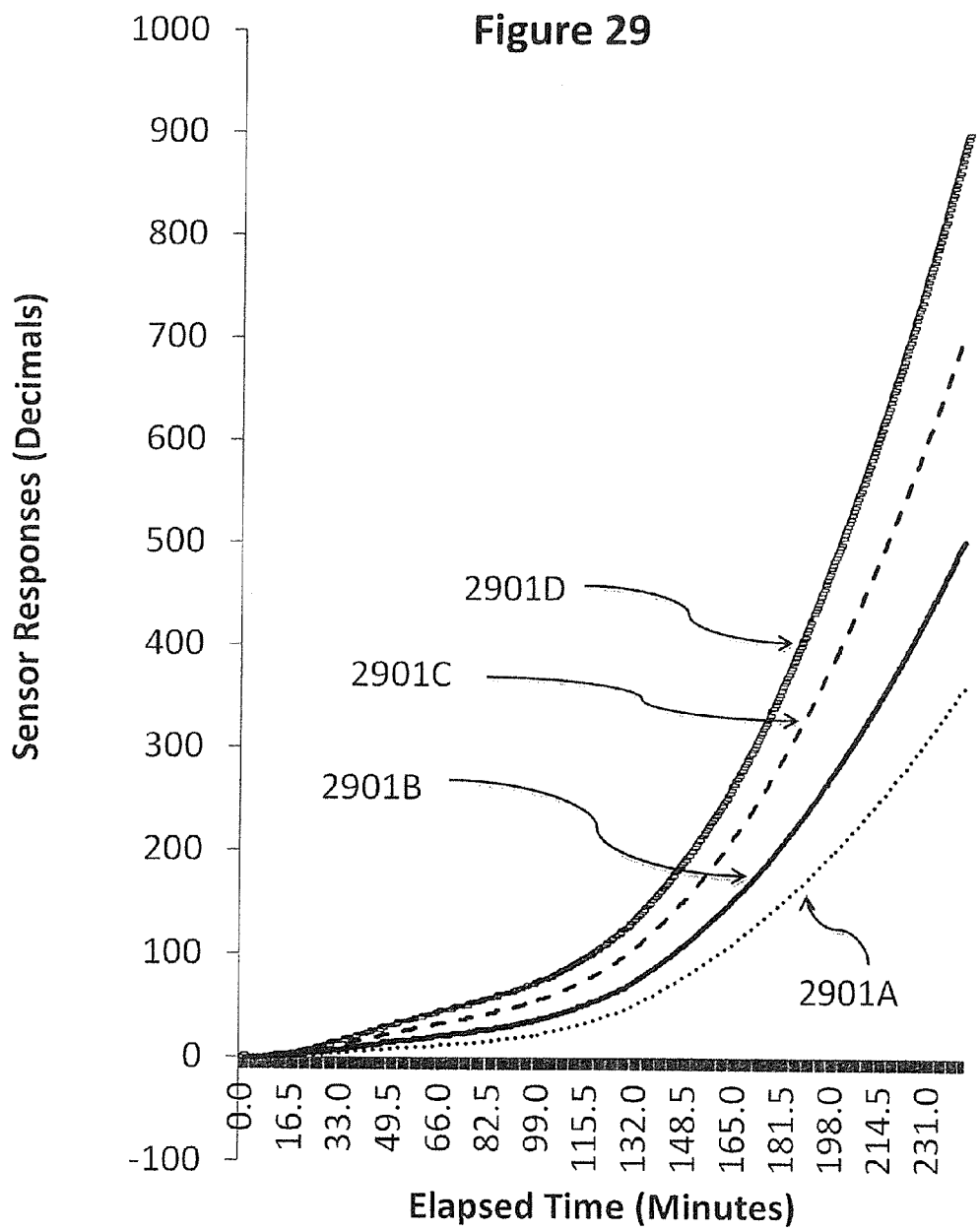

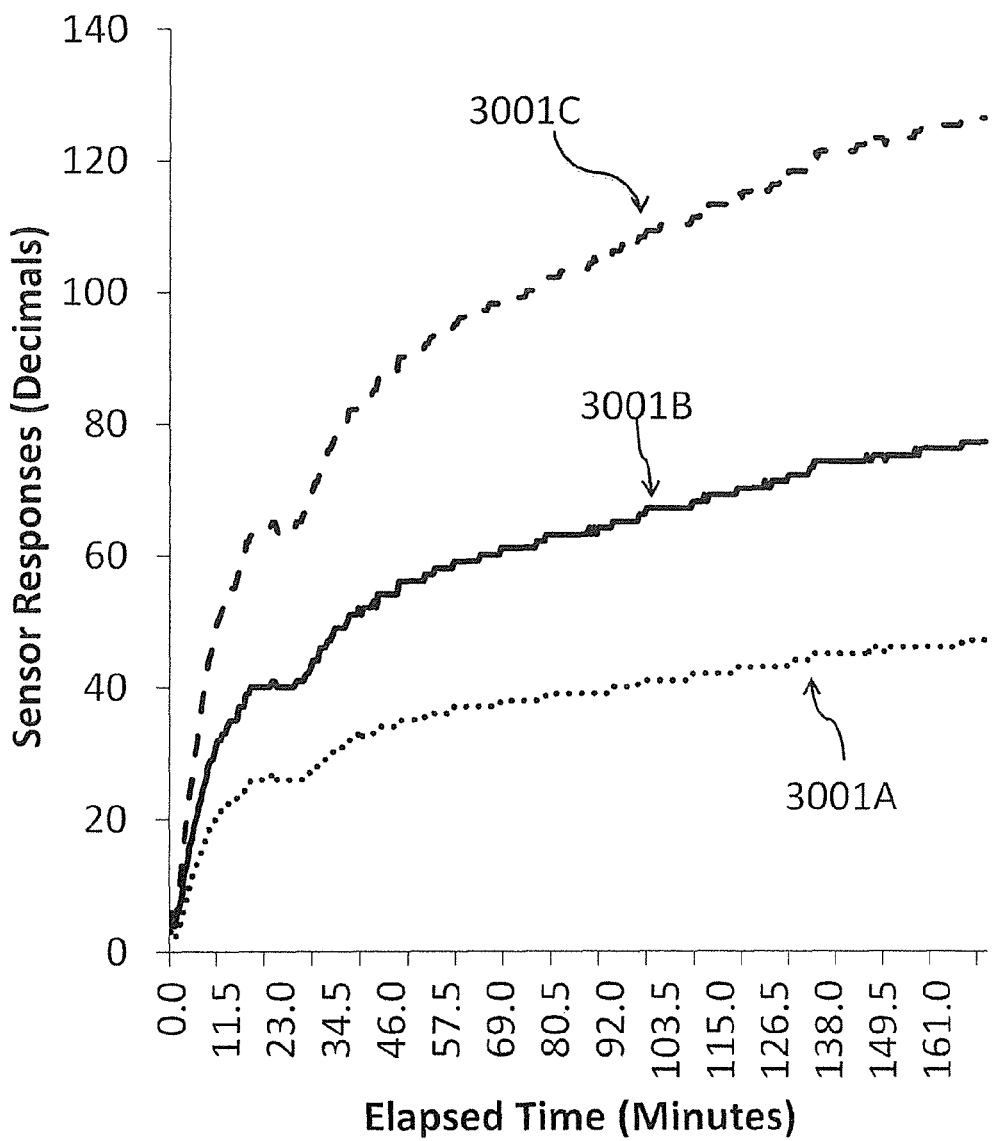

CARBON MONOXIDE SENSOR SYSTEM AND RELATED METHODS

CROSS-REFERENCE TO RELATED APPLICATIONS

This application is a continuation in part of U.S. patent application Ser. No. 13/565,627 filed on Aug. 2, 2012 which is a continuation of U.S. patent application Ser. No. 13/037,094, filed on Feb. 28, 2011 (Publication No. 2011/0142719, Published Jun. 16, 2011—Abandoned), which is a continuation of U.S. patent application Ser. No. 11/786,883, filed on Apr. 13, 2007 (Publication No. 2008/0173817, Published Jul. 24, 2008—Abandoned), which claims the benefit of U.S. Provisional Patent Application No. 60/792,103, filed Apr. 13, 2006.

FIELD OF THE INVENTION

The present invention relates to several novel improvements for detecting the presence of carbon monoxide using improved optically responding sensor chemistry, mechanical design, improved substrate and improved getter system to make a CO sensor with a useful life of at least ten years. In some cases, this chemistry needs only one instead of two solid-state sensing elements, for example, for residential and commercial applications that are considered by UL to be conditioned (heater and air conditioned) space as defined by Underwriters Laboratory (UL)/American National Standards Institute (ANSI) standards for carbon monoxide alarms in the United States, also known as UL 2034 (for single station home with conditioned space and for RV and other unconditioned space) and UL 2075 (for system detectors connect to a central panel which is most often monitored such as in a hotel). This improved chemistry complex of the present invention is coated onto porous silica substrates with a very thin layer (e.g. about 1 Angstroms to 100 Angstroms thick) of boron oxide to produce CO sensors that perform better at minus 40 C and are more stable and therefore live longer.

A brief review of the history of this invention and the state of the art is given below. The invention U.S. Pat. No. 5,618,493 discloses carbon monoxide sensors, which meet UL 2034 but used two sensing elements to pass residential section of UL 2034 effective 2009. The new novel MicroSIR of the present invention with single sensor is smaller and less expensive yet out performs and lives twice as long the larger SIR (which uses dual sensing disks in a much larger system) in accelerated age testing, although for safety reason we are expressing the useful life of the single sensor as ten years minimum. The single (sensing element) sensor is integrated into a humidity and air quality control device (chamber with small through-hole(s) or opening(s) to the outside environment), which regulates the humidity in the micro-environment provided in the housing described in detail below. The goal of humidity control is to prevent condensation and drying for better response at extreme conditions as specified in UL 2034 and UL 2075. Thus, for practical definition, the humidity is controlled between about 20% and 90% RH even during extended testing of 168 hours at 10% RH or 95% RH. Air diffusing from the outside passes through one or two small holes, each of about 0.034 inch in diameter, and then through a getter system that removes basic gases and vapors as well as other compounds, such as trichloroethylene, that could damage the sensor. The amount of precious and expensive materials (e.g., cyclodextrins, palladium salts, and molybdosilicic acid) used to make these new smaller sensors is about 25 times less than the previous SIR sensors, and thus lowers its material cost, which is a novel improvement of the present invention, along with its smaller size and longer life.

BACKGROUND AND SUMMARY OF THE INVENTION

Toxic gases and vapors such as carbon monoxide, and other reducing agents can be detected by a single rather two substrate formulation of the invention and still pass UL 2034 effective August 2009 and current UL 2075 (which include system detector connected to a central panel and ventilation controls to turn on fans). These toxic compounds are difficult to detect accurately (plus or minus 5%) without false alarms without expensive technology such as instruments costing over $100 to $100,000 depending upon the accuracy and type of technology used.

Carbon monoxide (CO) has no smell, cannot be seen or tasted, but is very toxic. Such gases are hazardous to humans in automobiles, airplanes, mines, residential and commercial buildings, and other environments in which humans live, work or spend time.

For many years various chemical sensors have been used to detect the presence of toxins. For example, the use of palladium and molybdenum salts for carbon monoxide detection is described in Analytical Chemistry, Vol. 19, No. 2, pages 77-81 (1974). Later, K. Shuler and G. Schrauzer improved upon this technology by adding a third metallic salt component, which produces a self-regenerating catalyst that is short-lived. The catalyst disclosed in U.S. Pat. No. 4,043,934 uses the impregnation of a carbon monoxide-sensitive chemical catalyst solution into powdered silica-gel substrates to give detectors sensitivity to low concentrations of atmospheric carbon monoxide. While this system is effective in detecting carbon monoxide, it has not met with commercial acceptance due to the short functional life of the catalyst of less than 6 months.

It is generally recognized that, for a carbon-monoxide sensor system to be commercially useful in alarms and/or detectors, it must have a functional life of at least three years according to UL and, preferably 10 years or more. Tests have shown that the material described in U.S. Pat. No. 4,043,934 has a working life of only two to four months at room temperature and only three to four days at forty degrees Celsius (40° C.) in an oven.

U.S. Pat. No. 5,063,164 provided a method for detecting CO, which has a (useful) functional life of at least six years without calibration and it can withstand 50 C for 30 days in a chamber. However, these formulations, which used only one solid-state substrate does not provide adequate sensitivity under high humidity and high temperature conditions, which cannot resist false alarm limits as specified in the Underwriters Laboratories (UL) 2034.

U.S. Pat. No. 5,618,493 is an improvement over U.S. Pat. Nos. 5,063,164 and 4,043,934. U.S. Pat. No. 5,618,493 discloses carbon monoxide sensors, which met UL 2034 effective April of 1992 and October of 1995. Hereafter these above patents are incorporated herein by reference. U.S. Pat. No. 5,618,493 requires two solid-state bio-derived organometallic complexes coated onto a transparent porous silica substrate to produce CO sensors in order to satisfy the performance requirement listed under UL 2034 for residential and RV. The yellow solid-state bio-derived organometallic sensor detects CO well at ambient to low humidity conditions while the red sensor detects CO at ambient to high humidity conditions.

U.S. Pat. No. 5,618,493 by itself failed to meet the stringent sequential test requirements specified by the 2nd. Edition of UL 2034, which became effective October 1 of 1998. A new invention was made by Mark Goldstein, U.S. Pat. No. 6,251,344 issued on Jun. 26, 2001, hereafter incorporated herein by reference, was made to better control the humidity and remove potential interference chemicals, which might damage the sensor's sensitivity to CO. In or about November of 2003, Goldstein and Oum made additional improvements to U.S. Pat. No. 6,251,344, which described a means to further maintain relative humidity and certain air quality contaminates within a predetermined range for a predetermined period of time within a chamber, which is connected to the atmosphere by one or more small openings. The objective is to maintain a specific air quality including relative humidity (RH) within a predetermined range for extended period of time under real world conditions as well as extreme conditions specified by the UL 2034 and UL 2075. The controlled chamber(s) is contained within a housing that has one or more small openings to the atmosphere. The relative humidity control system also comprises at least one opening to a reservoir of chemicals including a salt with water in at least some solid or a solution containing at least some excess solid phase salt such as manganese chloride ($MnCl_2 \times 4H_2O$), manganese bromide ($MnBr_2 \times 4H_2O$), or mixtures of the two. The humidity control system uses a hydrophobic membrane to containing the liquid solution and solid salt(s) within the reservoir chamber but allowing gases and water vapor to exchange with the atmosphere in the sensing chamber where the CO sensors are located. This control system maintains predetermined RH % range (between about 15% and 90% or in most case even better such that the sensor system is able to meet UL 2034 and UL 2075) within the "Controlled Chamber" for a given temperature range regardless of the humidity variations in the outside environment, even allowing operation in condensing conditions. Such a system is referred as "reservoir," hereafter. The reservoir allows the sensor formulations disclosed in U.S. Pat. No. 5,618,493 to meet the stringent sequential tests as required by the 2nd. Edition of UL 2034 by maintaining the humidity inside the micro-environment surrounding the sensors as close to ambient condition as possible. The controlled humidity condition prolongs the life of the sensors as they are subjected to extreme test conditions ranging from about $-40°$ C. to $+70°$ C. and from 7.5% RH to 95% RH sequentially without having to the replace any sensors from start to finish over a period of several months. In 95% humidity where condensing sometimes occurs depending on the location and operation, this reservoir prevents adverse effect from this condensing. And in low humidity conditions, it prevents the sensor from dehydrating. Although reservoir adds significant cost to manufacturing of the CO detectors, it is much needed along with a getter system in order to meet the UL 2034 requirements and to protect humans. (For extended periods of time such as 5 to 6 years depending sensor configuration and application, i.e. we set end of life for SIR at 5 years in passenger cars, truck and marine applications and 6 years in homes, apartments and hotels as well as other condition space.) With the improved chemistry, substrate, reservoir and getter, the MicroSIR will operate successfully for 10 years in conditioned space as defined by UL2034 and UL2075. This increased life and improved accelerated age testing is due to a combination of improvements and not one factor.

The present invention eliminates the need for two sensing disks in 90% of the single station market by the new chemical formulations of the chemistry as described in detail below for residential and other conditioned applications as specified in UL 2034 effective 2009 and current and proposed UL 2075. The chemistry was reformulated using a single MicroSIR Mini-size sensing improved substrate disk. The invention involves new formulations of sensing chemistry, specially combined and optimized so that only ONE instead of TWO sensing elements is enough to meet the requirement residential requirements specified under UL 2034 and live for over 10 years. Residential and commercial single station applications are 90% of the market and therefore most important from an economic point of view. The new single sensing chemistry formulations have been proven to perform better than both the regular-sized SIR sensors in the SIR assembly and to live longer (in fact twice as long in all accelerated age tests as shown below in detail. The micro-sized porous silica substrates are similar in composition to prior substrates but slightly different in pore diameter and structure, and have a thin coating on their surfaces of boron oxide, the coating having a thickness ranging between about 1 Angstrom and about 500 Angstroms. In some embodiments, the boron oxide may have a thickness of about 1 Angstrom to about 100 Angstroms. In some embodiments, the boron oxide layer thickness may be an average thickness (and generally, the slower the boron oxide layer is produced, the more uniform it is). The preferred embodiment using Quantum SPS substrate is 1 Angstrom to about 100 Angstroms; however for larger pore size material increase thickness is feasible such as was made by Robert Shoup U.S. Pat. No. 4,221,578 with pore size of about 1000 Angstroms to 10,000 Angstroms with average above 2000 Angstroms. Quantum's SPS has a typical pore diameter of 260 Angstroms with a surface area about 121.8 square meters per grams. The weight of the SIR disk is 0.054 grams. The density of amorphous SPS silica is about 2.2 grams/cc; however the SPS density due to the large number of hole is much less than 2.2 grams. It is 0.84 grams/cc. The SIR typical sized substrates are ~0.100 inch thick and ~0.230 inch in diameter as compared to the smaller mini-disks with boron oxide which are about ~0.050 inch thick by ~0.100 inch in diameter. The new sensing chemistry formulations can be applied to the substrates by either injection or immersion method. The injection method eliminates waste and has economic advantages because it has little or no waste and it uses much less of the more expensive materials (less than about ⅕ the cost of materials of the soak method).

The new single CO sensing element can replace the "dual CO sensing elements" in the current SIR CO alarm when the regular-size substrates are used. However, it requires UL approval testing from all over again and would not provide the advantages of longer life and better performance under extreme 30 day high temperature testing, which is an accelerated age test.

The time and money to obtain UL approval for switching from a dual to a single regular-sized CO sensing element is better justified when the single CO sensing chemistry is based on micro- or mini-sized substrates in MICROSIR; however, either size works well and passes all tests.

The new invention reduces the cost of sensor manufacturing by eliminating the need for two sensing disks to pass UL 2034 effective August 2009 residential section as well as by miniaturizing the sensing disk to require only 1/10 to 1/20 of the current starting materials for the sensor, which are expensive including cyclodextrin and its derivatives, palladium salts and molybdosilicic acid. The miniaturized single-sensing element requires less than 1/25 of the chemical sensing materials and less than 1/10 of the reservoirs materials (plastic, membrane, and chemical content). Bottom line, the new invention is expected to yield a net saving of 30 to 40% of the current manufacturing cost while exceeding or at least maintaining the same or better performance as the current SIR CO sensors which required TWO regular sized sensing elements. The Single-Sensing Micro-SIR has been shown to meet the latest UL 2034 for residential applications and live twice as long under accelerated age testing using ammonia as the life testing parameter. Several studies have shown that the limiting life mechanism is resistance of the sensing component(s) of the current sensor to ammonia, which has been found to average about 25 parts per million in a home (Helen H Suh, Petros Koutrakts, and John D. Spengler, Harvard School of Public Health, Journal of Exposure, Analysis and Environmental Epidemiology, Vol. 4, no. 1, 1994). However, it is desirable to design for extreme condition such as people who have several cats. In these cases, depending on the locations of the litter boxes and alarms, the ammonia concentration can be two to three times higher for some period of time. These cases have been shown to reduce the effective life of the sensor getter system of current SIR to a 6 year useful life.

Like the dual sensing elements counterpart, the new sensing element also needs a reservoir in order to meet the current UL 2034 standard and UL 2075 standard.

Here are a few examples of applications for the new Single-Sensing-SIR:

1. CO Alarms for Residential and Commercial single station and Residential and commercial system.

As mentioned above, the new Single-Sensing-SIR has been shown to meet the UL 2034 and 2075 for protecting human life against CO poisoning at homes, in commercial buildings, as well as in recreational vehicles and boats.

2. Visual CO Indicator

The new invention can be used as a visual CO detector for detecting the presence of CO. As visual CO detectors, the sensors made according to the formulations according to this invention require no power, no electronic, nor software. In the presence of CO (or at least a threshold level of CO), the sensor changes from one color to another color or one shade of color to another shade of color, e.g., tan-orange to dark-blue, at about 5-10% COHb. In the absence of CO, the sensors self-regenerate within a few hours to its original color and are reusable. These sensors also have over 6 years of operational life compared to 3 months for other technologies such as AIR-ZONE and DEAD-STOP. In addition to their amazing long sensor life, they also outperformed both AIR-ZONE and DEAD-STOP under wider range of relative humidity and temperature.

3. Digital CO Alarms and/or CO Instrumentation.

Results have indicated that the new Single-Sensing-SIR offers real potential for designing and manufacturing reliable, low cost CO alarms and potentially CO analyzers that allow digital display of the CO concentration on liquid crystal display (LCD). Most users do not know how to interpret CO levels and simply need to know the danger level. It may be an improvement to calculate the level of hazard, which is related to the percent carboxyhemoglobin in a human's blood. Once the hazard level is calculated, action plans can be announced by the alarm such as "open windows", "call a service person" or "evacuate now and call from an outside phone". These are two different action plans which would depend on the rate of rise as well as percent hemoglobin in the occupant's blood at the time.

In a preferred embodiment of a method of manufacturing a single sensor element, a substrate is coated first with boron oxide by heating the imbibed boric acid to over 160 C for about 2.5 hours. Then after cooling to room temperature, the substrate is coated with a supramolecular chemical reagent as described below to form a hybrid sensor. These hybrid sensors are referred to as the S6e and S66e sensor series. These sensors are well suited for detecting CO in the range of about 30 to 1,000 ppm. Other sensor formulations are better suited for detecting greater than about 1,000 ppm CO. The S6e and S66e sensor series re-gain their light transmittance in the presence of clean air (CO concentration <15 ppm) in about 1 to 2 hours. Any combinations of the three sensor series of S6e, or S66e with KYb to form a TWO element sensing system are referred to as a S34 series, as is done for marine, RV, or other unconditioned space applications.

Additional new CO sensing formulations that have increased sensitivity to CO after having been stored in low relative humidity for an extended period of time are referred to as the MO37-32b series, which occurs only with the boron oxide pre-coat of the substrate. The exact reason is not known.

Also the addition of $ZnCl_2$ and $ZnBr_2$ and/or $MnCl_2$ and $MnBr_2$ to replace a portion or all of the calcium chloride and calcium bromide in a group of the single sensor chemical formulation increases sensitivity under extreme aging conditions such 70 C for 30 days, which is an accelerated condition and very important for attaining the longest life sensor as possible.

The single sensor of the MICROSIR system of the present invention is small with a very low profile, which makes it suitable for many applications where small size is desired. The MICROSIR has at least seven additional advantages over the current SIR sensor system. These advantages of MICROSIR with improved substrate and chemistry over SIR include:

1. Lower cost per sensor manufacturing cost,

2. Better controlled-gas-path, therefore more accurate and more precision,

3. Better getter system therefore longer life (as shown by ammonia accelerated age tests the life resistance to basic gases such as ammonia is doubled), and 4. Better RESERVOIR SYSTEM THEREFORE BETTER Humidity CONTROL AT BOTH LOW AND HIGH (as shown by sensor response curves).

5. The MICROSIR "Edgeview" orientation of the sensor is faster and meets the European fire detection via CO also called enhanced smoke, and 6. More easily automated as the board of alarms use surface mount and MICROSIR is a surface mount part that attaches over surface mount optic after soldering.

7. Much smaller and therefore the alarm can be smaller and greener as there is less plastic and other materials as well as reducing shipping cost significantly.

BRIEF DESCRIPTION OF THE DRAWINGS

FIG. 1B is an exploded perspective view of the system of FIG. 1A, including an optical detection assembly.

FIG. 1C is an end cross-sectional view of the optical detection assembly of FIG. 1A, taken along line C-C.

FIG. 12 is graphical representation showing response characteristics of a ONE mini-sized CO sensor type S66 in a MICROSIR MOD1-01 to 70 ppm 1002, 150 ppm 1003, and 400 ppm CO 1004 at 23±3° C. and 55±5% RH, as specified in criteria 1.

FIG. 13B is graphical representation showing response characteristics of the same MICROSIR CO sensor system from FIG. 13A to 70 ppm 11B02, 150 ppm 11B03, and 400 ppm CO 11B04 at 66° C. and 40% RH, as specified in UL 2034 Section 69.1a.

FIG. 28 is a perspective view of a gas and smoke sensor system housed in alarm housing, in accordance with one embodiment of the present invention.

FIG. 29 is a graphical representation showing comparative response characteristics of the S66e CO sensing chemistry on SPS disks with different concentrations of boron oxide coating and without (control). The sensors were made according to Example 12A. These were responses to 70 ppm CO for 4 hours at minus (−) 40° C. as specified in UL 2034 Section 69.1b, except there was no prior 30 days preconditioning at 66° C. Both the software and hardware used were the 2011 UL approved "9SG1bb__36" for SIR CO detection system. According to FIG. 29, the response to CO is directly proportional to the concentrations of boron oxide coating ranging from zero 2901A (control), to 0.1N 2901B, to 0.5N 2901C, and to 1.0N boron oxide coating 2901D.

FIG. 30 is a graphical representation showing comparative response characteristics of the S66e CO sensing chemistry on SPS disks with different concentrations of boron oxide coating and without (control). The sensors were manufactured according to Example 12A. Shown are responses to 70 ppm CO for 4 hours at 66° C. and 40% RH following 4 days (instead of 30 days) of preconditioning at the same conditions, as specified in UL 2034 Section 69.1a. Both the software and hardware used were the 2011 UL approved "9SG1bb__36" for SIR. According to FIG. 30, the response to CO is proportional to the concentrations of boron oxide coating from zero 3001A (control), to 0.1N 3001B, and to 0.5N boron oxide coating 3001C.

DETAILED DESCRIPTION OF THE INVENTION

Figure 1A:
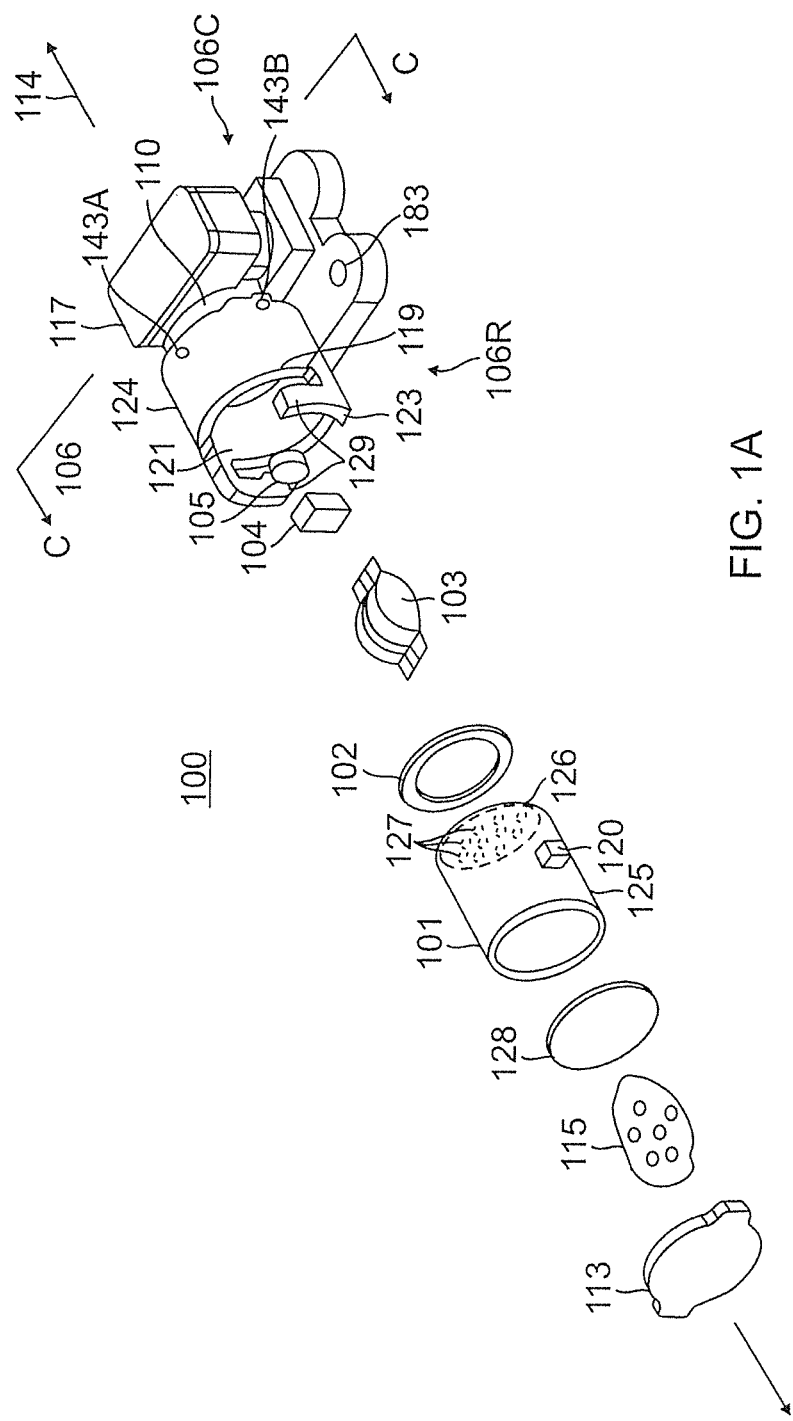
FIG. 1A is an exploded perspective view of a MICROSIR MOD3-01 gas sensor system 100 with only ONE, mini-sized CO sensing element located inside a controlled sensor chamber, in accordance with one embodiment of the present invention.

The present invention relates to an improved optical responding carbon monoxide sensor and related methods, wherein the sensor may use only a single porous, translucent substrate coated with chemical reagents including boron oxide and a mixture of cyclodextrins and their derivatives, palladium chloride and bromide salts, molybdosilicic acid, copper chloride and bromide salts, zinc and/or manganese chloride and bromide salts. Examples of the formulations are given below in detail. The optically responding carbon monoxide (CO) sensor constructed according to the principle of this invention is an improvement over the dual sensor system disclosed in U.S. Pat. Nos. 5,618,493 and 5,063,164 and lives for more than 10 years as opposed to 6 years. The porous silica is made by a modification of U.S. Pat. No. 4,059,658 to Robert Shoup. Shoup produced porous silica with pores sized around 4000 nm which is more than ten times greater than the size of the pores in the silica porous substrate of the present invention. The large pores made by Robert Shoup are strong but opaque and not suited for an optically responding sensor using transmission.

The dual CO sensor system disclosed in U.S. Pat. No. 5,618,493 uses light that is emitted by an IR light emitting diode (LED) to pass through two different sensors or sensing elements, and detected by a photo detector (photodiode). When the new improved ten year CO sensor of the present invention is exposed to CO, it darkens in a similar fashion in the near infrared, thereby reducing the amount of light transmitted but only one sensing element is required as its rate of change is greater than the two sensing elements thus making a better performing sensor with greater signal to noise ratio. The rate of change of the light transmittance reduction as registered by the photodiode is function of CO concentrations in the air. The light transmittance increases as the sensor regenerates when the CO is removed or reduced from an environment. In short, like the dual sensing system, the single sensing system also changes its optical properties in such a way as to allow easy detection of response by visible or infrared radiation, e.g., by means of a light emitting diode (LED) such as a 940 nm LED and a photo detector of the same photodiode and are described in more detailed below.

The improved CO sensor system using only one sensor disk that detects carbon monoxide and self-regenerates in air is fabricated from a semi-transparent silica porous substrate that is first coated or impregnated with a solution of 0.1 N boric acid (e.g., by adding 16 microliters of this solution to the substrate and allowing it to come to equilibrium) and then coated with a chemical reagent mixture sensitive to CO. This CO sensor disk is initially tan-orange after receiving the boric acid and the chemical reagent mixture (as described below under Example of Sensor Formulation with Boron Oxide), turns to first green when initially exposed to CO, and then, on continued exposure to CO, turns dark blue. However, there is a thermal test for stability, which is an estimate of sensor life.

The boron oxide coated sensors have a longer life compared to uncoated porous silica. For example, uncoated porous silica has a life of six years compared to 10 years for boron-oxide enhanced substrate.

The improved CO sensor system performs best between about 7.5 to 95% relative humidity from about −40° C. to +70° C. A new chemical reservoir assembly keeps the sensor in a narrower humidity range under most all real world conditions.

Figure 7:
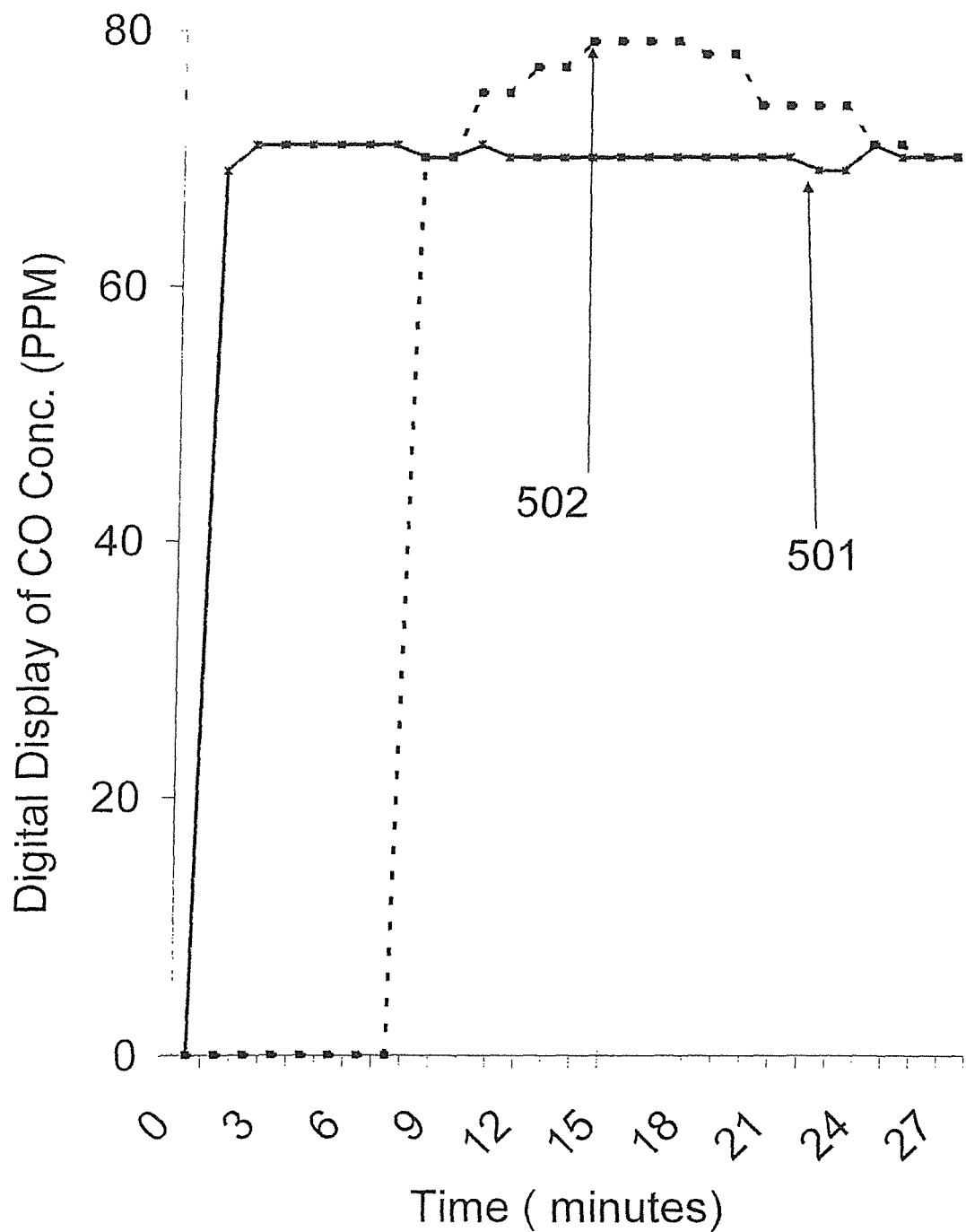
FIG. 7 is a plot of digital display of ppm CO versus time in 70 ppm CO test.
Figure 8:
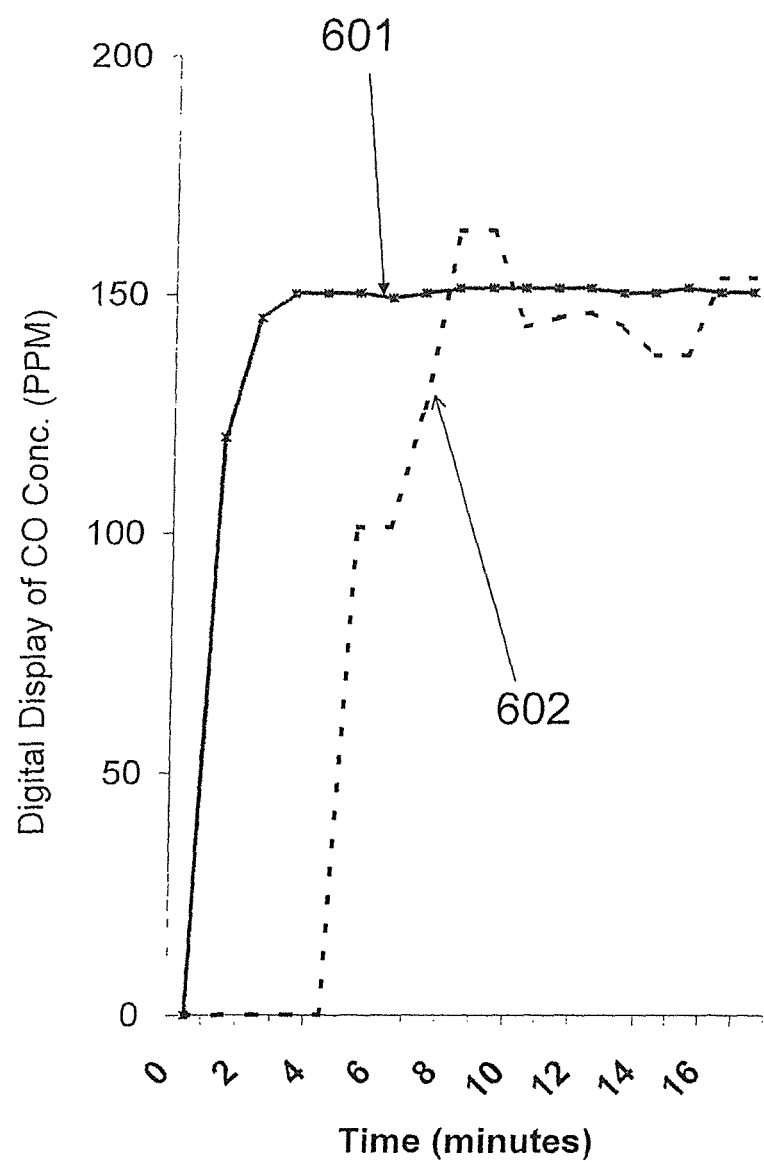
FIG. 8 are a plot of digital display of ppm CO versus time in 150 ppm CO test.

When tested in combination with the new chemical reservoir system as described in the, "Improved Chemical System for Controlling Relative Humidity and Air Quality," U.S. patent application Ser. No. 10/997,646, filed Nov. 24, 2004, now abandoned, the new Single-Sensing MicroSIR of the present invention performs well to meet stringent requirement as specified in UL 2034 and UL 2075. The results that verify this statement are shown in FIGS. 12 through 16. For the Single-Sensing MicroSIR when combined with the appropriate electronic circuitry and software equations, some preliminary test results that demonstrate this capability are shown in FIGS. 7 and 8.

Example of Sensor Formulation with Boron Oxide

The new improved CO optically responding sensor is made by impregnating semi-transparent porous silica disks with boric acid, followed by drying and heating the impregnated disks to 160 C, which converts the boric acid to boron oxides to form a boron oxide coating. For example, in some embodiments, the boric acid concentration may be in a range of about 0.001 N to about 2.1 N. For example, the boric acid concentration may be 0.001 N, 0.01 N, 0.1 N, 0.5 N, 1.0 N, 1.5 N, 2.0 N, or 2.1 N. In some embodiments, the drying step may be performed at about 40° C. for about 18 hours. Then the samples may be heated, and the temperature of the disks may be ramped up to about 160° C. over about 20 hours (for example, the temperature may increase about 10 degrees every 1.5 hours). After being at about 160° C. for about 3 hours, the disks may be cooled. Next the substrate is coated by self-assembly with a mixture including at least one chemical reagent from each of the following groups:

Group 1: Palladium salts selected from the group including palladium chloride, palladium bromide, $CaPdCl_4$, $CaPdBr_4$, $Na_2PdCl_4$, $Na_2PdBr_4$, $K_2PdCl_4$, $K_2PdBr_4$, $Na_2PdBr_4$, $CaPdCl_xBr_y$, $K_2PdBr_xCl_y$, $Na_2PdBr_xCl_y$ (where x can be 1 to 3 if y is 4 or vice versa), and mixtures of any portion or all of the above;

Group 2: Molybdenum compounds selected from the group consisting of silicomolybdic acid, phosphomolybdic acids, and their soluble salts, alkali metal, or alkaline earth metal salts of the silicomolybdic acid, mixed heteropolymolybdates, and mixtures of any portion or all of the above;

Group 3: Copper chloride, copper bromide, or mixtures thereof;

Group 4: Supramolecular complexing molecules selected from the group including cyclodextrin family including alpha, beta, and gamma as well as their soluble derivatives such as hydroxymethyl, hydroxyethyl, and hydroxypropyl beta cyclodextrins, and mixtures of any portion or all of the above; in some embodiments, at least two cyclodextrin supramolecular complexing molecules may be used;

Group 5: Soluble metal salts of bromide and chlorides, and in some embodiments, non-Ca soluble metal salts of bromide and chloride selected from $AlCl_3$, $AlBr_3$, $CdCl_2$, $CdBr_2$, $CoCl_2$, $CoBr_2$, $CeCl_3$, $CeBr_3$, $CrCl_3$, $CrBr_2$, $FeCl_3$, $FeBr_3$, $MnCl_2$, $MnBr_2$, $NiCl_2$, $NiBr_2$, $SrCl_2$, $SrBr_2$, $ZnCl_2$, $ZnBr_2$, $SnCl_2$, $SnBr_2$, $BaCl_2$, $BaCl_2$, $MgCl_2$, $MgBr_2$, and any mixture thereof;

Group 6: Organic solvent and/or co-solvent and trifluorinated organic anion selected from the group including trichloroacetic acid, trifluoroacetate, copper trifluoroacetylacetonate, or mixtures thereof;

Group 7: Soluble acids such as hydrochloric acid, Nitric acid and triflic acid or a mixture thereof;

Group 8: Strong oxidizer such as nitric acid and or hydrogen peroxide, or a mixture thereof.

The mole ratio ranges for the components of the reagent solution mixture used to formulate this new sensor, such as sensor named S6e and S66e "single CO sensing element" series for CO detection from 30 to 550 ppm are as follows:

Group 1 Group 3=10.19:1 to 16.98:1
Group 2 Group 3=3.04:1 to 5.07:1
Group 4 Group 3=1.04:1 to 1.74:1
Group 5 Group 3=34.11:1 to 56.84:1
Group 6 Group 3=1.07:1 to 1.79:1
Group 7 Group 3=0.004:1 to 0.04:1
Group 8 Group 3=0.04:1 to 0.08:1

And the mole ratio ranges for the components of the reagent solution mixture used to formulate this new KYb "single CO sensing element" for detecting CO ranges from 550 to 10,000-ppm CO are as follows:

Group 2 Group 1=0.30:1 to 0.35:1
Group 3 Group 1=0.10:1 to 4.75:1
Group 4 Group 1=0.05:1 to 0.1:1
Group 5 Group 1=1.75:1 to 2.92:1
Group 6 Group 1=0.00:1 to 0.00:1
Group 7 Group 1=0.62:1 to 1.03:1
Group 8 Group 1=0.70:1 to 1.16:1

The reagent solution mixtures, which contains at least one of the substances selected from groups 1 through 8 above, is further coated onto or encapsulated within a solid porous substrates of at least partial optical transparency to become "Single Sensing Element" for detecting CO. Some of these substrates are listed in Groups 9, 10, and 11 below.

Group 9: Porous silica substrates include, but are not limited to, porous silica gel coated with boron oxides coated; these substrates can be made in many sizes and shapes. Disk-shape is most preferred due to high yield. The silica is made by mixing colloidal silica with potassium silicate.

Group 10: Porous silica substrates from group 9 coated with boron oxides or mixed metal oxides that are not soluble or do not react with any of the chemical reagents described in-groups 1 through 8 such as the oxide of boron $Al_2O_3$, ZnO, and mixtures thereof.

Group 11: Porous silica gel such as in bead form, which is commercially available from many suppliers of silica gel or porous silicon dioxide. Such porous silica beads contain average pore diameters ranging from 80 to 150 Angstroms (15 nm) with surface area of 250 to 600 m/gram. An example of this material includes the Grade TS-1 supplied by CHEM SOURCE-EAST, Inc. 7865 Quarterfield Road Severn, Md. 21144, Telephone No. 410-969-3390, which contains bead sizes ranging from 1 mm to 5 mm., pore diameters range from 110 to 130 angstroms pore, and surface areas range from 340 to 400 $m_2$/gram surface area, and pore volumes range 0.9 to 1.1 cc/g. The substrate performs better when coated with boron oxides as it stabilizes the aging process allowing much longer life sensors from 1.5 years on a visual sensor to 3 years in a visual detector with a small getter system.

These substrates also have performed exceptionally well as substrate support CO oxidation catalysts, especially when certain mixed oxide containing copper and chromium.

There are many applications for carbon monoxide sensors of this type and therefore there are many preferred embodiments for each of the applications, several of these formulations are described below.

The formulations described below are examples of Single CO Sensing Chemistry types S6 and S66 series on regular-size and mini-sized silica porous substrate (SPS) disks with boron oxide coating.

Figure 5:
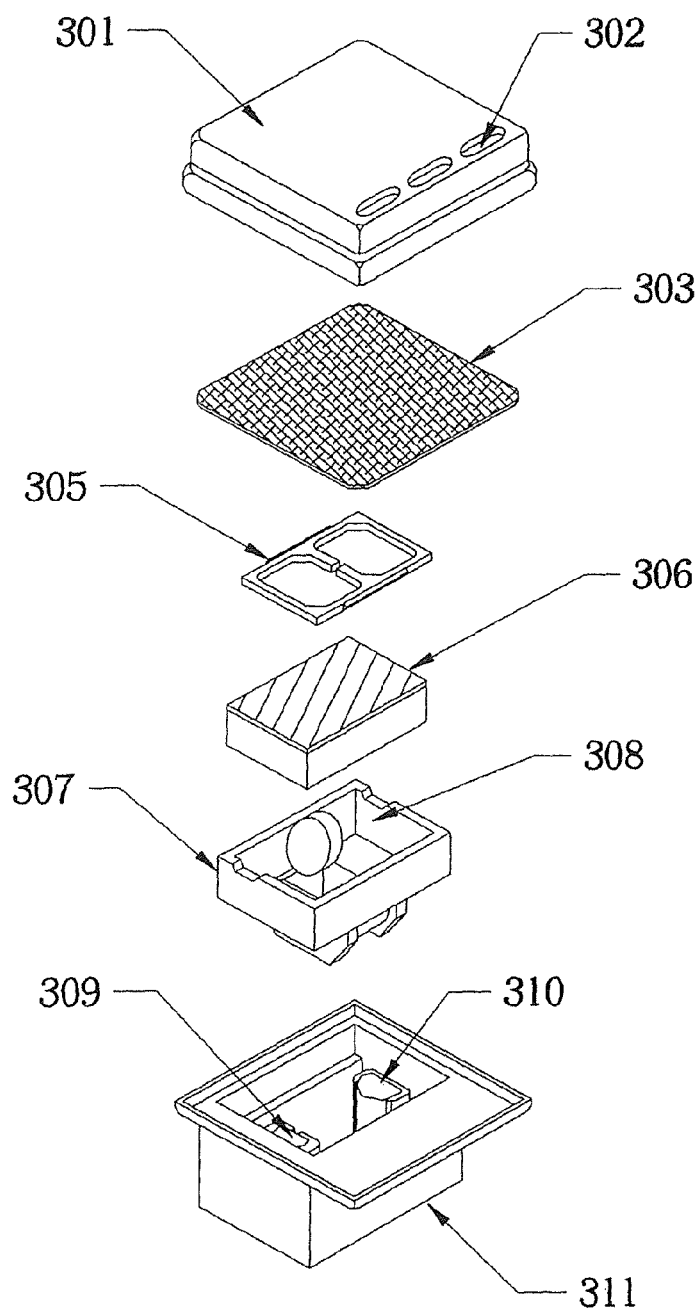
FIG. 5 is an assembly drawing of SIR-01 system 300 with ONE, standard-sized CO sensing element located inside a controlled sensor chamber.

When the regular-sized disks are impregnated with the new hybrid, single CO sensing chemistry, the resulted regular-sized Single CO Sensing elements are to be installed SINGLY inside SIR-01 assembly configuration as shown in FIG. 5. Using the new reservoir content as detailed in a co-pending patent application, "Improved Chemical System for Controlling Relative Humidity and Air Quality," U.S. patent application Ser. No. 10/997,646 (now abandoned), filed Nov. 24, 2004, the Single Sensing Element of the present invention can effectively replace DUAL CO sensing system for residential and commercial condition space as specified by UL 2034 and UL 2075, hence; reducing cost in the current COSTAR® CO alarms such as Models 3RV, 3 mSIR, and 12-24 mSIR. However, they must first be improved to pass the new UL requirement proposed for UL 2075 but not yet issued to the public.

Figure 6:
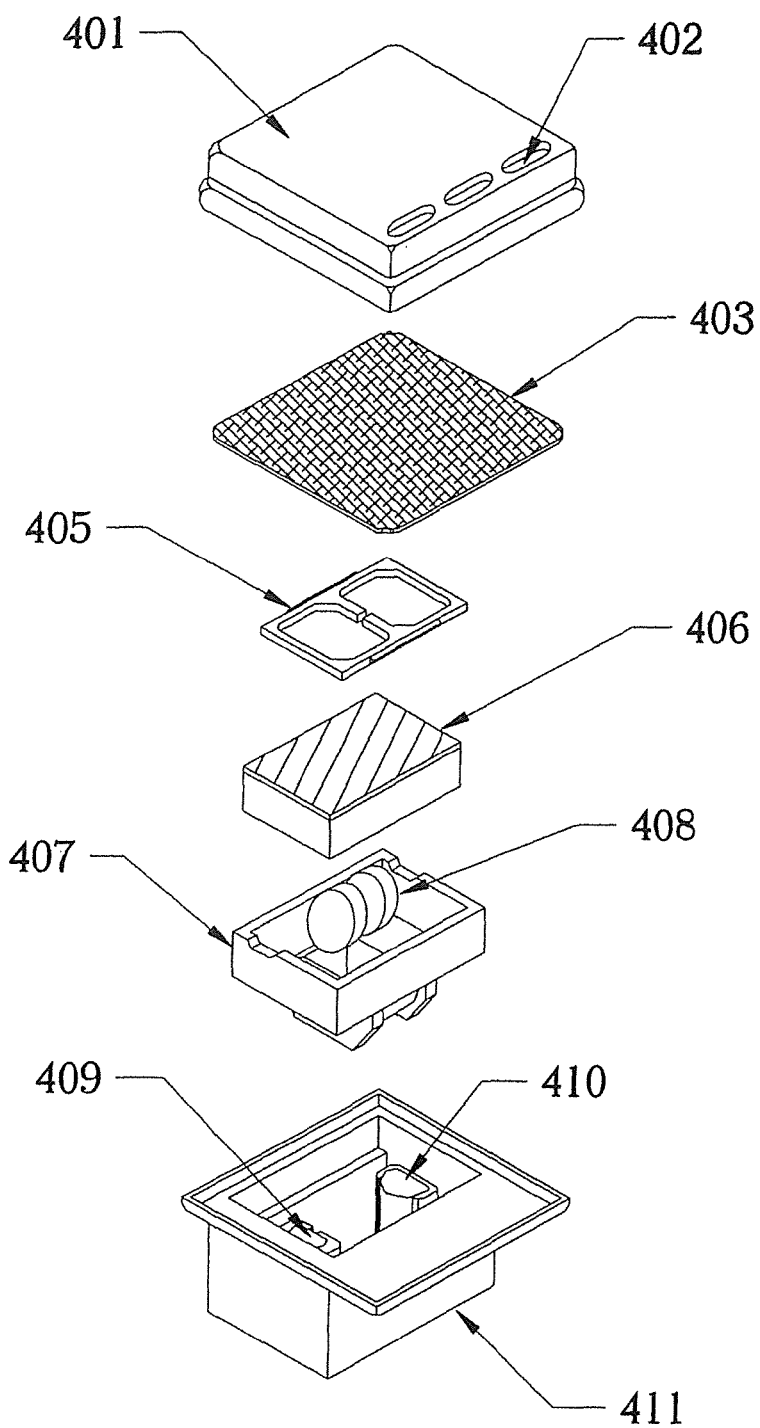
FIG. 6 is an assembly drawing of SIR-02 system 400 with TWO, standard-sized, CO sensing elements in regular SIR reservoir assembly and shows how MicroSIR overcomes the problem of size, controlled gas path and thus longer life with ammonia.

A SECOND, regular-sized, CO sensing element type KYb series is needed to meet the 550 to 6,000 ppm CO response and recovery requirement for "recreational boats" application under UL 2034. The TWO sensing elements system is referred to as the S34 CO sensor series and to be installed in a SIR-02 assembly configuration as shown in FIG. 6. The marine sensor comprised a pair of S6e or S66e and KYb that provides CO detection range from 30 to 6,000 ppm.

Figure 4:
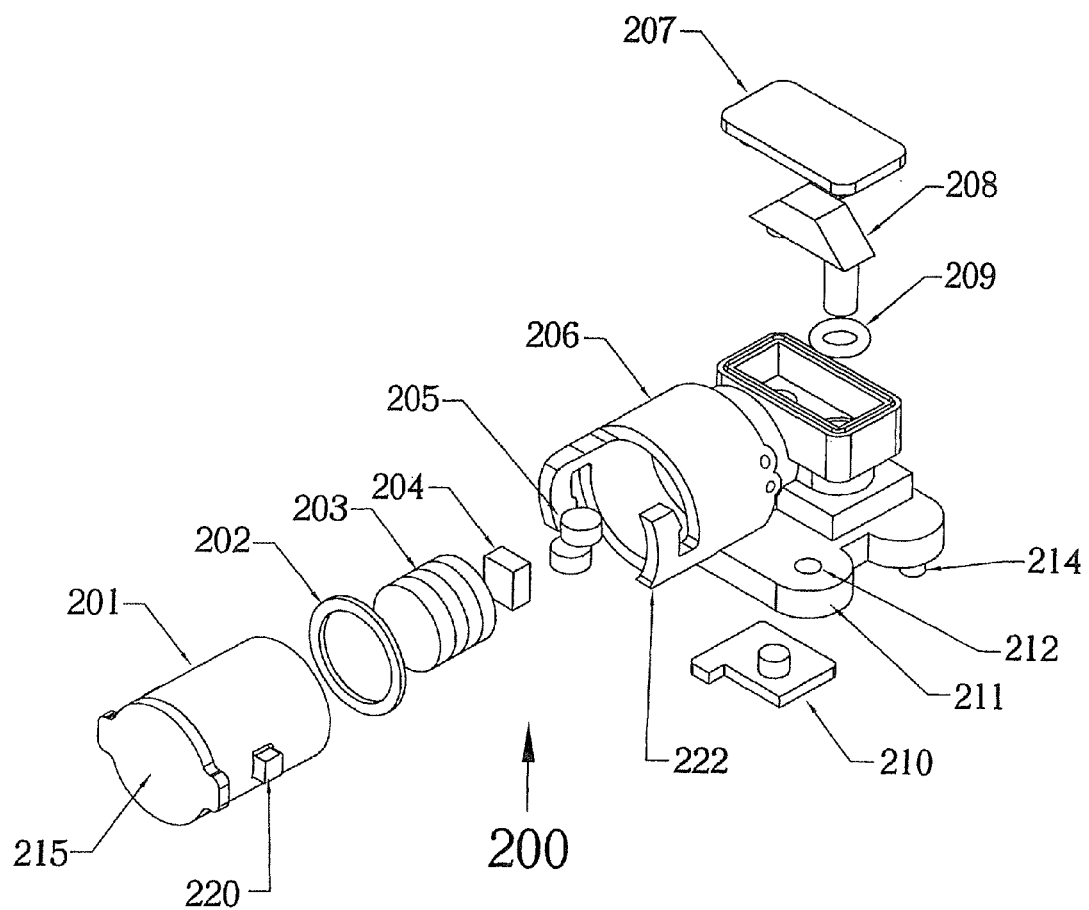
FIG. 4 is an assembly drawing of MICROSIR MOD3-02 system 200 with TWO, mini-sized CO sensing elements located inside a controlled sensor chamber.

When the mini-sized disks are impregnated with boric acid and the converted to a coating of boron oxides and then the new single CO sensing chemistry in accordance with the present invention, the resulting mini-SPS Single CO Sensing element is installed SINGLY in a MICROSIR assembly such as the MOD1-01 (FIG. 9) or the MOD3 (FIG. 1A) and tested according to UL 2034 and UL 2075 for residential and commercial applications. A SECOND, mini-sized, CO sensing element type KYb series is needed to meet the 550 to 6,000 ppm CO response and recovery requirement for "recreational boats" application under UL 2034. The TWO mini-sized sensing elements are referred to as the mini-disks for CO sensor series and to be installed in MICROSIR MOD1-02 (FIG. 10) and MICROSIR MOD3-02 (FIG. 4). The mini-S34 CO sensor series comprise any pair of mins-S6e or mini-S66e and mini-KYb; and provides CO detection range from about 30 to 6,000 ppm.

Figure 33:
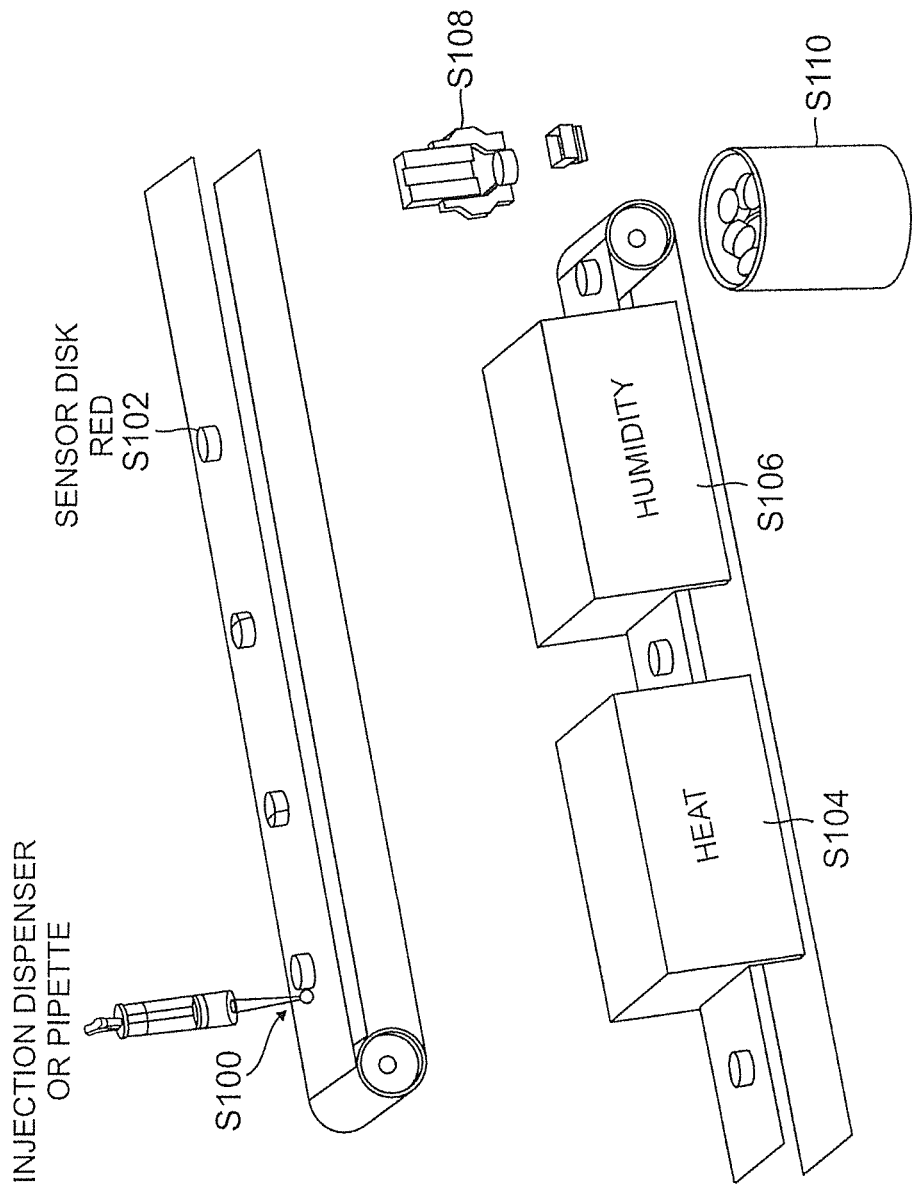
FIG. 33 is a schematic drawing showing a method of injecting reagent into a substrate according to an embodiment of the present invention.

"Soak method" is currently used to fabricate the sensors and is described in the examples below. This method may unnecessarily waste about 67% of the sensing reagents per standard-size SPS and 72% per mini-sized SPS, when compares to "Injection method." However, the cost of labor for the "manual injection method" outweighs the cost of the wasted sensing reagents. Future manufacturing of these sensors should be based on an "automated injection method" to save on both labor and material costs in the future. As shown in FIG. 33, the injection method (whether automated or manual) refers to a capillary injection method where in step S100, an amount of reagent is expelled from a dispenser (e.g., a pipette) adjacent to a substrate disk. In step S102, through capillary action, the reagent is absorbed into the substrate disk (or adsorbed on a surface of the substrate disk) and may coat and/or permeate the substrate disk. An appropriate amount of reagent is selected so that enough reagent is used to coat and/or permeate the disk without providing excess reagent. Once the reagent has coated and/or permeated the disk, the disk is heated in step S104 to dry the disk, and subjected to controlled humidity in step S106. The specific heating and humidifying steps may be similar to those used in the soaking method, and may be, for example, dried at room temperature at controlled humidity prior to heating. Then, the coated disks may be directly placed in a housing in step S108 or placed into a tray in step S110.

Either method of immersion or injection works for any sensor formulations on standard-size SPS and mini-size SPS and SPS coated with boron oxides. Example 1A and 1B described both methods in details.

Preferred Embodiment 1

Visual CO Indicator

Example 1A

Single CO Sensing Formulation S6e on Regular-Sized SPS for SIR

"Soak Method"

100 of 0.100" diameter×0.050" thick silica porous silicate disks with pore diameter ranging from 200 to 300 angstroms and surface area ranging from 100 to 200 square meter per gram with boron oxide coating are soaked in a 15-mL of the new S6e sensing formulation containing 7.7 mmole of $H_4SiMo_{12}O_{40}.xH_2O$, 77.7 mmole of $CaCl_2.2H_2O$, 2.7 mmole of $CCl_3COOH$, 0.16 mmole of copper trifluoroacetylacetonate, 1.74 mmole of $CuCl_2.2H_2O$, 8.6 mmole of $ZnBr_2.2H_2O$, 1.126 mmole of Gamma-Cyclodextrin, 0.97 mmole of Hydroxy-Beta-Cyclodextrin, 1.89 mmole of $Na_2PdCl_4$, 23.89 mmole of $PdCl_2$, and 0.55 mmole of Beta-Cyclodextrin. After 1 day of soaking, the excess solution is removed and the sensor dried using Kimwipe tissue paper. Sensors are spread flat on a clean Pyrex or plastic tray and allowed to dry slowly inside a polyester felt pillow case inside the humidity and temperature controlled room or chamber with relative humidity maintain within 45 to 55% and temperature within 20 to 26° C. After 1 day, the pillowcase is removed and the sensors are allowed to further air dry in the same controlled room for 1 more day. Then the sensor tray is placed inside 40° C. drying oven for 1 to 2 days. The sensor tray is removed and stored inside the humidity and temperature controlled chamber. The sensors are now ready for use or for test.

Manual Injection Method 100 of 0.100" diameter×0.050" thick silica porous silicate disks with pore diameter ranging from 200 to 300 angstroms and surface area ranging from 100 to 200 square meter per gram are coated with boron oxide are spread flat on a clean Pyrex tray or polyethylene tray.

Using a micropipette, inject 50-microliters of the new S6e sensing formulation containing 7.7 mmole of $H_4SiMoO40.xH2O$, 77.7 mmole of $ZnCl_2.2H_2O$, 2.7 mmole of $CCl_3COOH$, 0.16 mmole of copper trifluoroacetylacetonate, 1.74 mmole of $CuCl_2.2H_2O$, 8.6 mmole of $MnBr_2.2H_2O$, 1.126 mmole of Gamma-Cyclodextrin, 0.97 mmole of Hydroxy-Beta-Cyclodextrin, 1.89 mmole of $Na_2PdCl_4$, 23.89 mmole of $PdCl_2$, and 0.55 mmole of Beta-Cyclodextrin on the bottom-side of each disk. The tray is inserted inside a polyester felt pillow case, while sitting inside a humidity and temperature controlled room or chamber with relative humidity maintain within 45 to 55% and temperature within 20 to 26° C. for optimal self-assembly of the supramolecular layering. After 14 to 24 hours, the pillowcase is removed and the sensors are allowed to further air dry in the same controlled room for an additional 14 to 24 hours. Then the sensor tray is placed inside 40° C. drying oven for 14 to 24 hours. Then the sensor tray is removed and stored inside the humidity and temperature controlled chamber. The sensors are now ready for use or for test.

Preferred Embodiment 2

Single Sensing Element MICROSIR for CO Alarm that Meets UL 2034

Example 1B

Single Sensing Formulation S6e on Mini-SPS for MICROSIR

"Soak Method"

600 of the mini-sized silica porous silicate disks with pore diameter ranging from 200 to 300 angstroms and surface area ranging from 100 to 200 square meter per gram are soaked with boric acid, dried and the heated to 16° C. for 3 hours. Then they are cooled to room temperature soaked in a 15-mL of the new S6e sensing formulation containing 7.7 mmole of $H_4SiMo_{12}O_{40}.xH_2O$, 38.8 mmole of $CaCl_2.xH_2O$ and 38.8 mmole of $MgCl_2.xH2O$, 2.7 mmole of $CCl_3COOH$, 0.16 mmole of copper trifluoroacetylacetonate, 1.74 mmole of $CuCl_2.xH_2O$, 4.3 mmole of $ZnBr_2.4H_2O$ and 4.3 mmole of $MnBr_2.4H_2O$, 1.126 mmole of Gamma-Cyclodextrin, 0.97 mmole of Hydroxy-Beta-Cyclodextrin, 1.89 mmole of $Na_2PdCl_4$, 23.89 mmole of $PdCl_2$, and 0.55 mmole of Beta-Cyclodextrin. After 1 day of soaking, the excess solution is removed and the sensor dried using Kimwipe tissue paper. Sensors are spread flat on a clean Pyrex or plastic tray and allowed to dry slowly inside a polyester felt pillow case inside the humidity and temperature controlled room or chamber with relative humidity maintain within 45 to 55% and temperature within 20 to 26° C. After 1 day, the pillowcase is removed and the sensors are allowed to further air dry in the same controlled room for 1 more day. Then the sensor tray is placed inside 40° C. drying oven for 1 to 2 days. The sensor tray is removed and stored inside the humidity and temperature controlled chamber. The sensors are now ready for use or for test.

"Injection Method"

Mini-sized SPS coated with boron oxides are spread flat on a clean Pyrex or plastic tray. 7 to 10 microliters of the single sensing element reagent mixture S6e containing 7.7 mmole of $H_4SiMo_{12}O_{40}.xH_2O$, 77.7 mmole of $CaCl_2.2H_2O$, 2.7 mmole of $CCl_3COOH$, 0.16 mmole of copper trifluoroacetylacetonate, 1.74 mmole of $CuCl_2.2H_2O$, 8.6 mmole of $ZnBr_2.2H_2O$, 1.126 mmole of Gamma-Cyclodextrin, 0.97 mmole of Hydroxy-Beta-Cyclodextrin, 1.89 mmole of $Na_2PdCl_4$, 23.89 mmole of $PdCl_2$, and 0.55 mmole of Beta-Cyclodextrin is injected directly onto a mini-sized porous silica substrate (SPS) having the dimensions of 0.100" diameter×0.050" thick. The tray is inserted inside a polyester felt pillow case, while sitting inside a humidity and temperature controlled room or chamber with relative humidity maintain within 45 to 55% and temperature within 20 to 26° C. for optimal self-assembly of the supramolecular layering. After 14 to 24 hours, the pillowcase is removed and the sensors are allowed to further air dry in the same controlled room for an additional 14 to 24 hours. Then the sensor tray is placed inside 40° C. drying oven for 14 to 24 hours. Then the sensor tray is removed and stored inside the humidity and temperature controlled chamber. The sensors are now ready for use or for test.

Example 3A

Single Sensing Formulation S66e on Regular-Size SPS for SIR 100 of 0.230" diameter×0.100" thick silica porous silicate disks with pore diameter ranging from 200 to 300 angstroms and surface area ranging from 100 to 200 square meter per gram are soaked in a 15 mL of the new S66e sensing reagent mixture containing 7.87 mmole of $H_4SiMo_{12}O_{40}.xH_2O$, 38 mmole of $CaCl_2.xH_2O$ and 38 mmole of $MnCl_2.xH_2O$ and, 2.7 mmole of $CCl_3COOH$, 0.16 mmole of copper trifluoroacetylacetonate, 1.74 mmole of $CuCl_2.2H_2O$, 8.6 mmole of $ZnBr_2.2H_2O$, 1.126 mmole of Gamma-Cyclodextrin, 0.97 mmole of Hydroxy-Beta-Cyclodextrin, 2.25 mmole of $Na_2PdCl_4$, 23.89 mmole of $PdCl_2$, and 0.55 mmole of Beta-Cyclodextrin. After 1 day of soaking, the excess solution is removed and the sensor dried using Kimwipe tissue paper. Sensors are spread flat on a clean Pyrex or plastic tray and allowed to dry slowly inside a polyester felt pillow case inside a humidity and temperature control room or chamber with relative humidity maintain with 45 to 55% and temperature within 20 to 26° C. After 1 day of soaking, the excess solution is removed and the sensor dried using Kimwipe tissue paper. Sensors are spread flat on a clean Pyrex or plastic tray and allowed to dry slowly inside a polyester felt pillow case inside the humidity and temperature controlled room or chamber with relative humidity maintain within 45 to 55% and temperature within 20 to 26° C. After 1 day, the pillowcase is removed and the sensors are allowed to further air dry in the same controlled room for 1 more day. Then the sensor tray is placed inside 40° C. drying oven for 1 to 2 days. The sensor tray is removed and stored inside the humidity and temperature controlled chamber. The sensors are now ready for use or for test.

Example 3B

Single Sensing Formulation S66e on Mini-SPS, MICROSIR 7 to 10 microliters of the single sensing element reagent mixture containing 7.87 mmole of $H_4SiMo_{12}O_{40}.xH_2O$, 77.7 mmole of $CaCl_2.XH_2O$, 2.7 mmole of $CCl_3COOH$, 0.16 mmole of copper trifluoroacetylacetonate, 1.74 mmole of $CuCl_2.2H_2O$, 8.6 mmole of $ZnBr_2.XH_2O$, 1.126 mmole of Gamma-Cyclodextrin, 0.97 mmole of Hydroxy-Beta-Cyclodextrin, 2.25 mmole of $Na_2PdCl_4$, 23.89 mmole of $PdCl_2$, and 0.55 mmole of Beta-Cyclodextrin is injected directly onto a mini-sized porous silica substrate (SPS) having the dimensions of 0.100" diameter×0.050" thick. The impregnated mini-sized substrates are spread flat on a clean Pyrex or plastic tray inside a polyester felt pillow case, while sitting inside a humidity and temperature controlled room or chamber with relative humidity maintain within 45 to 55% and temperature within 20 to 26° C. for optimal self-assembly of the supramolecular layering. After 14 to 24 hours, the pillowcase is removed and the sensors are allowed to further air dry in the same controlled room for an additional 14 to 24 hours. Then the sensor tray is placed inside 40° C. drying oven for 14 to 24 hours. Then the sensor tray is removed and stored inside the humidity and temperature controlled chamber. The sensors are now ready for use or for test.

Example 4A

Single Sensing Formulation S66L on Regular-Size SPS for SIR 100 of 0.230" diameter×0.100" thick silica porous silicate (SPS) disks with pore diameter ranging from 200 to 300 angstroms and surface area ranging from 100 to 200 square meter per gram are soaked in a 15 mL of the new single sensing element reagent mixture type S66L containing 8.25 mmole of $H_4SiMo_{12}O_{40}.xH_2O$, 77.7 mmole of $CaCl_2.2H_2O$, 2.7 mmole of $CCl_3COOH$, 0.16 mmole of copper trifluoroacetylacetonate, 1.74 mmole of $CuCl_2.2H_2O$, 8.6 mmole of $ZnBr_2.2H_2O$, 1.126 mmole of Gamma-Cyclodextrin, 0.97 mmole of Hydroxy-Beta-Cyclodextrin, 3.33 mmole of $Na_2PdCl_4$, 23.89 mmole of $PdCl_2$, and 0.55 mmole of Beta-Cyclodextrin. After 1 day of soaking, the excess solution is removed and the sensor dried using Kimwipe tissue paper. Sensors are spread flat on a clean Pyrex or plastic tray and allowed to dry slowly inside a polyester felt pillow case inside humidity and temperature controlled room or chamber with relative humidity maintain within 45 to 55% and temperature within 20 to 26° C. After 1 day, the pillowcase is removed and the sensors are allowed to further air dry in the same controlled room for 1 more day. Then the sensor tray is placed inside 40° C. drying oven for 1 to 2 days. The sensor tray is removed and stored inside the humidity and temperature controlled chamber. The sensors are now ready for use or for test.

Preferred Embodiment 4

Example 4B

Single Sensing Formulation S66L on Mini-SPSb for MICROSIR M1 and M3

7 to 10 microliters of the single sensing element reagent mixture containing 8.25 mmole of $H_4SiMo_{12}O_{40}.xH_2O$, 77.7 mmole of $CaCl_2.2H_2O$, 2.7 mmole of $CCl_3COOH$, 0.16 mmole of copper trifluoroacetylacetonate, 1.74 mmole of $CuCl_2.2H_2O$, 8.6 mmole of $CaBr_2.2H_2O$, 1.126 mmole of Gamma-Cyclodextrin, 0.97 mmole of Hydroxy-Beta-Cyclodextrin, 3.33 mmole of $Na_2PdCl_4$, 23.89 mmole of $PdCl_2$, and 0.55 mmole of Beta-Cyclodextrin is injected directly onto a mini-sized porous silica substrate (SPS) having the dimensions of 0.100" diameter×0.050" thick. The impregnated mini-sized substrates are spread flat on a clean Pyrex or plastic tray inside a polyester felt pillow case, while sitting inside a humidity and temperature controlled room or chamber with relative humidity maintain within 45 to 55% and temperature within 20 to 26° C. for optimal self-assembly of the supramolecular layering. After 14 to 24 hours, the pillowcase is removed and the sensors are allowed to further air dry in the same controlled room for an additional 14 to 24 hours. Then the sensor tray is placed inside 40° C. drying oven for 14 to 24 hours. Then the sensor tray is removed and stored inside the humidity and temperature controlled chamber. The sensors are now ready for use or for test.

The new formulations for a ONE sensing element system described above have CO detection capability ranges from 30 to 550 ppm. The formulations can be further tuned to have wider ranges of CO detection capabilities simply by increasing the Cu ions concentration from 100 to 1000%. This is necessary for CO alarms to have in order to meet UL 2034 for "Recreational Boats" approval. The current UL 2034 requires CO alarms to detect 6,000 ppm CO within 3 minutes. Since UL also requires that the same CO alarm must also detect as low as 70 ppm CO, "two sensing elements" are needed to cover the full range from 30 to 6,000 ppm CO. Effective Mar. 8, 2007, UL 2034 lowered the upper detection limit to 5,000 ppm for Recreational Boats application.

To differentiate between low and high CO detection range sensors, bromide ions can be removed to give the high-CO-range sensors the yellow appearance, leaving the tan-orange to red appearance for low-CO-range sensors. The yellow high-CO-range sensors are referred to as the "KYb" series. Several examples of these formulations with these higher ranges of CO detection capability are shown below.

Preferred Embodiment 5

Example 5A

SIR-02, UL 2034, "Recreational Boats" Applications 100 of 0.230" diameter×0.105" thick silica porous silicate (SPS) disks coated with boron oxide with pore diameter ranging from 200 to 300 angstroms and surface area ranging from 100 to 200 square meter per gram are soaked in a 15-mL of 7KY type solution, which contains 0.008226391M $H_4SiMo_{12}O_{40}$, 0.071897966M $MnCl_2.4H_2O$, 0.014567462M $CuCl_2.2H_2O$, 0.001069612M Gamma-CD, 0.002013936M $Na_2PdCl_4$, 0.028761424M $PdCl_2$, 0.000913589M Beta-CD. After 1 day of soaking, the excess solution is removed and the sensor dried using Kimwipe tissue paper. Sensors are spread flat on a clean Pyrex or plastic tray and allowed to dry slowly inside a polyester felt pillow case inside humidity and temperature controlled room or chamber with relative humidity maintain within 45 to 55% and temperature within 20 to 26° C. After 1 day, the pillowcase is removed and the sensors are allowed to further air dry in the same controlled room for 1 more day. Then the sensor tray is placed inside 40° C. drying oven for 1 to 2 days. The sensor tray is removed and stored inside the humidity and temperature controlled chamber. The sensors are now ready for use or for test

Preferred Embodiment 6

Example 5B

Mini-S34 Sensor Series Comprising a Mini-7KYb Sensor+a Mini-S6e or Mini-S66e Series in a MICROSIR MOD1-02 (M1-02) or a MOD3-02 (M3-02) for "Recreational Boats" Application Per UL 2034

7 to 10 microliters of the 7KYb solution containing 0.008226391M $H_4SiMo_{12}O_{40}$, 0.071897966M $ZnCl_2.4H_2O$, 0.014567462M $CuCl_2.2H_2O$, 0.001069612M Gamma-CD, 0.002013936M $Na_2PdCl_4$, 0.028761424M $PdCl_2$, and 0.000913589M Beta-CD is injected directly onto a mini-sized porous silica substrate (SPS) having the dimensions of 0.100" diameter×0.050" thick. The impregnated mini-sized substrates are spread flat on a clean Pyrex or plastic tray inside a polyester felt pillow case, while sitting inside a humidity and temperature controlled room or chamber with relative humidity maintain within 45 to 55% and temperature within 20 to 26° C. for optimal self-assembly of the supramolecular layering. After 14 to 24 hours, the pillowcase is removed and the sensors are allowed to further air dry in the same controlled room for an additional 14 to 24 hours. Then the sensor tray is placed inside 40° C. drying oven for 14 to 24 hours.

Then the sensor tray is removed and stored inside the humidity and temperature controlled chamber. The sensors are now ready for use or for test.

Other new formulations to increase to the SENSITIVITY of the chemical sensors to CO after having been stored at very low relative humidity for an extended period of time involved the replacement hydrates of $CaCl_2$ with the hydrates of $AlCl_3$, $CdCl_2CeCl_3$, $FeCl_3$, $NiCl_2$, $MnCl_2$, $SrCl_2$, $ZnCl_2$, $SnCl_2$, $BaCl_2$, and $MgCl_2$ and mixtures thereof. The formulations are referred to as the MO37-32 and MO37-64 series. Some of the formulations that yielded positive results are described below.

Preferred Embodiment 6

Example 6

Single CO Sensing SIR, UL Residential and Recreational Vehicle 100 of 0.230" diameter×0.105" thick silica porous silicate (SPS) disks coated with boron oxide with pore diameter ranging from 200 to 300 angstroms and surface area ranging from 100 to 200 square meter per gram are soaked in a 15-mL 0.008226398M $H_4SiMo_{12}O_{40}$, 0.001069613M Gamma-CD, 0.00091359 M Beta-CD, 0.071898031M $MnCl_2.4H_2O$, 0.00202082M $CuCl_2.2H_2O$, 0.002013938M $Na_2PdCl_4$, and 0.02876145M $PdCl_2$. After 1 day of soaking, the excess solution is removed and the sensor dried using Kimwipe tissue papers. Sensors are spread flat on a clean Pyrex or plastic tray and allowed to dry slowly inside a polyester felt pillow case inside the humidity and temperature controlled room or chamber with relative humidity maintain within 45 to 55% and temperature within 20 to 26° C. After 1 day, the pillowcase is removed and the sensors are allowed to further air dry in the same controlled room for 1 more day. Then the sensor tray is placed inside 40° C. drying oven for 1 to 2 days. The sensor tray is removed and stored inside the humidity and temperature controlled chamber. The sensors are now ready for use or for test.

Preferred Embodiment 7

Example 7

Single CO Sensing SIR, UL Residential and Recreational Vehicle 100 of 0.230" diameter×0.105" thick silica porous silicate (SPS) disks coated with boron oxides with pore diameter ranging from 200 to 300 angstroms and surface area ranging from 100 to 200 square meter per gram are soaked in a 15-mL 0.008226398M $H_4SiMo_{12}O_{40}$, 0.001069613M Gamma-CD, 0.00091359M Beta-CD, 0.071898031M $CeCl_3$, 0.00202082M $CuCl_2.2H_2O$, 0.002013938M $Na_2PdCl_4$, and 0.02876145M $PdCl_2$. After 1 day of soaking, the excess solution is removed and the sensor dried using Kimwipe tissue paper. Sensors are spread flat on a clean Pyrex or plastic tray and allowed to dry slowly inside a polyester felt pillow case inside the humidity and temperature controlled room or chamber with relative humidity maintain within 45 to 55% and temperature within 20 to 26° C. After 1 day, the pillowcase is removed and the sensors are allowed to further air dry in the same controlled room for 1 more day. Then the sensor tray is placed inside 40° C. drying oven for 1 to 2 days. The sensor tray is removed and stored inside the humidity and temperature controlled chamber. The sensors are now ready for use or for test.

Ca chloride or bromide partial or complete replacement by chloride and bromide salts of Sr, Zn, Ni, and Mn has resulted in increases in the sensitivity to CO at extreme test conditions such as 66° C./40% RH for 30 days, which is an accelerated age test so it indicates an increase life and 61° C./93% RH is also an accelerated age test at high humidity another extreme, which implies much longer life. It was also observed that different mixture proportions of these salts yield different level of sensitivity gain/loss. One of most desired proportions is detailed in "preferred embodiment 8" below.

Preferred Embodiment 8

Example 8B

Single Sensing Mini-SPS S6e w/ Ca Replaced by Zn to Increase Sensitivity at 66° C./40% RH and 61° C./93% RH "Soak Method"

600 of the mini-sized silica porous silicate disks with pore diameter ranging from 200 to 300 angstroms and surface area ranging from 100 to 200 square meter per gram are soaked in a 15-mL of the new S6e sensing formulation containing 7.7 mmole of $H_4SiMo_{12}O_{40}.xH2O$, 38.9 mmole $ZnCl_2$, 38.9 mmole $ZnBr_2$, 2.7 mmole of $CCl_3COOH$, 0.16 mmole of copper trifluoroacetylacetonate, 1.74 mmole of $CuCl_2.2H_2O$, 8.6 mmole of $CaBr_2.2H_2O$, 1.126 mmole of Gamma-Cyclodextrin, 0.97 mmole of Hydroxy-Beta-Cyclodextrin, 1.89 mmole of $Na_2PdCl_4$, 23.89 mmole of $PdCl_2$, and 0.55 mmole of Beta-Cyclodextrin. After 1 day of soaking, the excess solution is removed and the sensor dried using Kimwipe tissue paper. Sensors are spread flat on a clean Pyrex or plastic tray and allowed to dry slowly inside a polyester felt pillowcase inside the humidity and temperature controlled room or chamber with relative humidity maintain within 45 to 55% and temperature within 20 to 26° C. After 1 day, the pillowcase is removed and the sensors are allowed to further air dry in the same controlled room for 1 more day. Then the sensor tray is placed inside 40° C. drying oven for 1 to 2 days. The sensor tray is removed and stored inside the humidity and temperature controlled chamber. The sensors are now ready for use or for test.

Another new group of formulations to increase to the SENSITIVITY of the chemical sensors to CO after having been stored at very low relative humidity for an extended period of time involved the addition of $AlCl_3$, $CdCl_2$, $CoCl_2$, $CeCl_3$, $CrCl_3$, $FeCl_3$, $MnCl_2$, $NiCl_2$, $SrCl_2$, or $ZnCl_2$ to the Single Sensing Formulation type S6e as detailed in Example 1. This new group of formulations is known as the MO37-141 series. Additives such as $AlCl_3$, $CdCl_2$, $CrCl_3$, $MnCl_2$, $SrCl_2$, and $ZnCl_2$ were confirmed to have increased SENSITIVITY to CO at low relative humidity conditions.

Table 1

Low 11% Relative Humidity Long-Term-CO Sensitivity Measurement

MO37-141 Series involves additions of various chlorides including aluminum and certain transition metal to the Single CO sensing formulation S6e. Comparison of Confirmed CO Sensitivities for S6e+Additives and those of S6e without additives and the current dual sensing disks S34: Sensors only (no reservoir effect), were stored inside a chamber containing a saturated salt of LiCl for maintaining relative humidity within 11-15% RH at room temperature. After 168 hours, the CO was injected to create 150 ppm. Sensitivity of each sensor was measured at the end of 20 minutes at 150 ppm CO. A sensitivity of 2 represents a 50% change. A single sensing element S6e is more sensitive than the dual sensing elements S34. Additives No. 1, 2, 5, 7, 9, and 10 cause the sensor sensitivity to be greater than those of S6e and S34.

TABLE 1

| ADDITIVES TO S6e | QTY. OF SENSING ELEMENT | CONFIRMED SENSITIVITY AT 13 ± 2% RH |
|---|---|---|
| 1 $AlCl_3$ | 1 | 3.5 |
| 2 $CdCl_2$ | 1 | 3.3 |
| 3 $CoCl_2$ | 1 | 2.3 |
| 4 $CeCl_3$ | 1 | 1.0 |
| 5 $CrCl_3$ | 1 | 4.9 |
| 6 $FeCl_3$ | 1 | 1.8 |
| 7 $MnCl_2$ | 1 | 2.7 |
| 8 $NiCl_2$ | 1 | 2.2 |
| 9 $SrCl_2$ | 1 | 2.5 |
| 10 $ZnCl_2$ | 1 | 3.7 |
| S6e control | 1 | 2.4 |
| S34 current | 2 | 2.1 |

Table 2

CO Sensitivity Measurements at 66° C. and 40% RH Following 30 Days of Preconditioning at the Same 66° C. and 40% RH Conditions Additional confirmed improved performance at 66° C. and 40% RH was found in formulations involving partial to complete replacement $CaCl_2$ in S6e with $MnCl_2.XH_2O$ and $MnBr_2.XH_2O$. Also found was a decreased in sensitivity when a partial to complete $CaCl_2$ replacement was made with $SrCl_2$ and $SrBr_2$. It was discovered that different proportions of $CoCl_2$, $MnCl_2$, $MnBr_2$, $SrCl_2$ and/or $SrBr_2$ yielded different levels of CO sensitivity. Single sensing mini-sized SPS was used in this experiment. They were singly installed in the MICROSIR MOD1-01 assembly configuration (FIG. 9) then mounted on the 8UP-MICROSIR-voltage output board, so the sensor output is converted to a voltage level corresponding to the obscuration of light passing through the MICROSIR CO sensing element. The signal conditioning is performed by a test circuit containing an operational amplifier (OpAmp). The amplification circuit is set to attain an initial value of 4 Volts output in the absence of CO. As the sensor responds to CO, the voltage output decreases. This voltage-output board is a subject of a co-pending U.S. Provisional Patent Application No. 60/711,748, filed on Aug. 25, 2005. The complete assembled samples were then stored inside a Thermotron environmental chamber, which maintained at 66° C. and 40% RH for 30 days. At the end of the 30$^{th}$ day, CO was injected to create and maintain at 400±10 ppm for 15 minutes. Changes in voltage in response to CO were calculated and summarized below. Proportion combination #1 is the control S6e. It has a change in voltage of less than (<) 0.05 volt. Two proportion combinations, which have better performances than that of the control, are #3 and 5 as shown in Table 2. All other proportion combinations are less sensitive to CO than the control.

TABLE 2

| Proportion Combination # | $CaCl_2$ | $MnCl_2$ | $MnBr_2$ | Confirmed Performance at 66° C./40% RH |
|---|---|---|---|---|
| 1 | 1 | 0 | 0 | <0.05 |
| 2 | 0 | 1 | 0 | <0.05 |
| 3 | 0 | 0.5 | 0.5 | 0.1 |
| 4 | 0.5 | 0.5 | 0 | 0.05 |
| 5 | 0.5 | 0 | 0.5 | 0.07 |
| 7 | 0 | 1 | 0 | <0.01 |
| 8 | 0 | 0.5 | 0.5 | <0.01 |
| 9 | 0.5 | 0.5 | 0 | 0.01 |
| 10 | 0.5 | 0 | 0.5 | 0.05 |

While partial to full replacement of $CaCl_2$ with $MnCl_2$, $MnBr_2$, $SrCl_2$, and/or $SrBr_2$ yielded some improved performances at 66° C./40% RH, addition of these same chemicals to S6e formulation does not yield fruitful results in either a −40° C. or a 66° C./40% RH test.

Table 3

CO Sensitivity Measurements at 66° C. and 40% RH Following 30 Days of Preconditioning at 66° C. and 40% RH Additional confirmed improved performance at 66 C and 40% RH was found in formulations involving partial to complete replacement of $CaCl_2$ in S6e with $ZnCl_2$ and $ZnBr_2$. Also found was a decrease in sensitivity when a partial to complete $CaCl_2$ replacement was made with $NiCl_2$ and $NiBr_2$. It was discovered that different proportions of $CaCl_2$, $ZnCl_2$, $ZnBr_2$, $NiCl_2$ and/or $NiBr_2$ yielded different levels of CO sensitivity. Single sensing mini-sized SPS disks were used in this experiment. They were singly installed in the MICROSIR MOD1-01 assembly configuration (FIG. 9) then mounted on the same 8UP-MICROSIR-voltage output OpAmp board used to generate the results show in TABLE 2 above. The complete assembled samples were then stored inside a Thermotron environmental chamber, which maintained at 66° C. and 40% RH. At the end of the 30$^{th}$ day, CO was injected to create and maintain at 400±10 ppm for 15 minutes. Changes in voltage in response to 400 ppm CO for 15 minutes was calculated and summarized in Table 3 below. Proportion combination #1 is the control S6e with change in voltage of 0.15V. Note it may seem contradicting when comparing the performance of the control used in this experiment to that of the control S6e used in Table 2. The differences may be caused by a test-to-test variation for it is important to compare the performances of the experimental sensors to that of the control used in the same given test. Proportion combinations involving $ZnCl_2$ and $ZnBr_2$ that yielded better response than the control are C, D, and 9 with the voltage change of 0.3V, 0.2V, and 0.9V, respectively. None of proportion combinations involving $NiCl_2$ and $NiBr_2$ yielded any better performances than the control, which had voltage change of 0.15V. Following this test, the samples were further tested at 61° C./93% RHC and are shown in Table 4.

TABLE 3

| Proportion Combination # | $CaCl_2$ | $ZnCl_2$ | $ZnBr_2$ | Confirmed Performance at 66° C./40% RH Change in Voltage (Volt) |
|---|---|---|---|---|
| A | 1 | 0 | 0 | 0.15 (Control) |
| B | 0 | 1 | 0 | 0.04 |
| C | 0 | 0.5 | 0.5 | 0.3 |
| D | 0.5 | 0.5 | 0 | 0.2 |
| E | 0.5 | 0 | 0.5 | 0.9 |
| F | 0 | 1 | 0 | 0.03 |
| G | 0 | 0.5 | 0.5 | 0.06 |
| H | 0.5 | 0.5 | 0 | 0.05 |
| I | 0.5 | 0 | 0.5 | 0.07 |

Table 4

CO Sensitivity Measurement at 61° C. and 93% RH Following 10 Days of Preconditioning at 61° C. and 93% RH The results shown in Table 4 were produced by the exact same samples reported in Table 3. The samples were preconditioned inside a Thermotron environmental chamber at 61° C. and 93% RH. At the end of the 10$^{th}$ day, CO was injected into the chamber to create and to maintain within 400±10 ppm CO for 15 minutes. Changes in voltage in response to 400 ppm CO for 15 minutes were calculated and summarized below. According to data, all obtainable results for proportion combinations C, G, H, and I are at least 4 times more sensitive than the control.

TABLE 4

| Proportion Combination # | CaCl$_2$ | ZnCl$_2$ | ZnBr$_2$ | Confirmed Performance at 61° C./93% RH Change in Voltage (Volt) |
|---|---|---|---|---|
| A | 1 | 0 | 0 | 0.05 (Control) |
| C | 0 | 0.5 | 0.5 | 0.3 |
| G | 0 | 0.5 | 0.5 | 0.3 |
| H | 0.5 | 0.5 | 0 | 0.2 |
| I | 0.5 | 0 | 0.5 | 0.3 |

Based on the obtainable results shown in Tables 3 and 4, proportion combination C appears to be the best among all other combinations because it is two times more sensitive than the control at 66° C./40% RH and six times better than the control at 61° C./93% RH.

Table 5

High % Relative Humidity, Long-Term-CO Sensitivity Measurement

Based on the confirmed CO sensitivity measurements of the MO37-141 and MO37-34 Series, it is predicted that a combination of bromide and chloride salts of the same transitional metal would results in increase CO sensitivity after the sensors have been stored at both LOW and HIGH relative humidity conditions for an extended period.

Predicted CO Sensitivity for the following: S6e with the additions of bromide and chloride salts of transitional metals, S6e with bromide and chloride salts of Ca replaced by bromide and chloride salts of transitional metals,

TABLE 5

| ADDITIVES TO S6e | # OF SENSING ELEMENT | CONFIRMED CO SENSITIVITY AT 13 ± 2% RH | PREDICTED CO SENSITIVITY AT 95 ± 4% RH |
|---|---|---|---|
| 1. AlCl$_3$&AlBr$_3$ | 1 | + | + |
| 2. CdCl$_2$&CdBr$_2$ | 1 | + | + |
| 3. CoCl$_2$&CoBr$_2$ | 1 | − | − |
| 4. CeCl$_3$&CeBr$_3$ | 1 | − | − |
| 5. CrCl$_3$&CrBr$_3$ | 1 | ++ | ++ |
| 6. FeCl$_3$&FeBr$_3$ | 1 | −− | −− |
| 7. MnCl$_2$&MnBr$_2$ | 1 | + | + |
| 8. NiCl$_2$&NiBr$_2$ | 1 | − | − |
| 9. SrCl$_2$ & ZnBr$_2$ | 1 | + | + |
| 10. ZnCl$_2$ & ZnBr$_2$ | 1 | + | + |
| S6e control | 1 | S6e control | S6e control |
| S34 current | 2 | S34 control | S34 control |

Based on the fact that bromide and chloride salts of certain transitional metals made the sensing elements TOO SENSITIVE at 0° C., it is also suggested that any mixture combinations of these salts might also INCREASE SENSITIVITY to CO at the extreme temperature conditions.

Table 6

Minus (−) 40° C. and +70° C.: CO Sensitivity Testing

Predicted increase in CO Sensitivity at extreme temperature of minus (−) 40° C. and +70° C. "+"=INCREASE in SENSITIVITY by having Bromide and Chloride Salts of Transitional metals in the S6e or S66 or the fast recovery sensor series KY formulations.

"−"=DECREASE in SENSITIVITY by having Bromide and Chloride Salts of Transitional metals in the S6e or S66 or the KY sensing formulations.

Bromide and Chloride Salts of Transitional metal, # of Sensing ElementsPredicted CO Sensitivity at minus (−) 40° C., Predicted CO Sensitivity at +70° C.

TABLE 6

| BROMIDE AND CHLORIDE SALTS OF TRANSITIONAL METAL | # OF SENSING ELEMENT | PREDICTED CO SENSITVITY AT MINUS (−)40° C. | PREDICTED CO SENSITIVITY AT +70° C. |
|---|---|---|---|
| 1. AlCl$_3$&AlBr$_3$ | 1 | + | + |
| 2. CdCl$_2$&CdBr$_2$ | 1 | + | + |
| 3. CoCl$_2$ & CoBr$_2$ | 1 | − | − |
| 4. CeCl$_3$ & CeBr$_3$ | 1 | + | + |
| 5. CrCl$_3$ & CrBr$_3$ | 1 | + | + |
| 6. FeCl$_3$ & FeBr$_3$ | 1 | − | − |
| 7. MnCl$_2$ & MnBr$_2$ | 1 | + | + |
| 8. NiCl$_2$ & NiBr$_2$ | 1 | − | − |
| 9. SrCl$_2$ & SrBr$_2$ | 1 | + | + |
| 10. ZnCl$_2$ & ZnBr$_2$ | 1 | + | + |

Preferred Embodiment 9

Example 9

SIR-01, Single CO Sensing Element, UL 2034 Residential and RV 100 of 0.100" diameter×0.050" thick silica porous silicate disks with pore diameter ranging from 200 to 300 angstroms and surface area ranging from 100 to 200 square meter per gram are soaked in a 15 mL of the new S6e sensing formulation containing 7.7 mmole of H$_4$SiMo$_{12}$O$_{40}$.xH$_2$O, 77.7 mmole of CaCl$_2$.2H$_2$O, 35.5 mmole of a 50:50 mixture of MnCl$_2$.4H$_2$O and MnBr$_2$.4H$_2$O, 2.7 mmole of CCl$_3$COOH, 0.16 mmole of copper trifluoroacetylacetonate, 1.74 mmole of CuCl$_2$.2H$_2$O, 8.6 mmole of CaBr$_2$.2H$_2$O, 1.126 mmole of Gamma-Cyclodextrin, 0.97 mmole of Hydroxy-Beta-Cyclodextrin, 1.89 mmole of Na$_2$PdCl$_4$, 23.89 mmole of PdCl$_2$, and 0.55 mmole of Beta-Cyclodextrin. After 1 day of soaking, the excess solution is removed and the sensors are dried using Kimwipe tissue paper. Sensors are spread flat on a clean Pyrex or plastic tray and allowed to dry slowly inside a polyester felt pillowcase inside humidity and temperature controlled room or chamber with relative humidity maintain within 45 to 55% and temperature within 20 to 26° C. After 1 day, the pillowcase is removed and the sensors are allowed to further air dry in the same controlled room for 1 additional day. Then the sensor tray is placed inside a 40° C. drying oven for 1 to 2 days. The sensor tray is removed and stored inside humidity and temperature controlled chamber. The sensors are now ready for test.

Example 9a

SIR-01, S6e Single CO Sensing Element, UL 2034 Residential and RV 100 of 0.100" diameter×0.050" thick silica porous silicate (SPS) disks with pore diameter ranging from 200 to 300 angstroms and surface area ranging from 100 to 200 square meter per gram are soaked in a 15 mL of the new S6e sensing formulation containing 7.7 mmole of H$_4$SiMO$_{12}$O$_{40}$.xH$_2$O, 77.7 mmole of CaCl$_2$.2H$_2$O, 35.95 mmole CdCl$_2$, 2.7 mmole of CCl$_3$COOH, 0.16 mmole of copper trifluoroacetylacetonate, 1.74 mmole of CuCl$_2$.2H$_2$O, 8.6 mmole of CaBr$_2$.2H$_2$O, 1.126 mmole of Gamma-Cyclodextrin, 0.97 mmole of Hydroxy-Beta-Cyclodextrin, 1.89 mmole of $Na_2PdCl_4$, 23.89 mmole of $PdCl_2$, and 0.55 mmole of Beta-Cyclodextrin. After 1 day of soaking, the excess solution is removed and the sensors are dried using Kimwipe tissue paper. Sensors are spread flat on a clean Pyrex or plastic tray and allowed to dry slowly inside a polyester felt pillowcase inside humidity and temperature controlled room or chamber with relative humidity maintain within 45 to 55% and temperature within 20 to 26° C. After 1 day, the pillowcase is removed and the sensors are allowed to further air dry in the same controlled room for 1 more day. Then the sensor tray is placed inside a 40° C. drying oven for 1 to 2 days. The sensor tray is removed and stored inside the humidity and temperature controlled chamber. The sensors are now ready for test.

Example 10

One preferred embodiment for detecting CO in dry low humidity application such as 7-10% RH is shown below in example 10.

(SIR-01, S6e Single CO Sensing Element, UL 2034 Residential and RV 100 of 0.100" diameter×0.050" thick silica porous silicate disks with pore diameter ranging from 200 to 300 angstroms and surface area ranging from 100 to 200 square meter per gram are soaked in a 15 mL of the new S6e sensing formulation containing 7.7 mmole of $H_4SiMO_{12}O_{40}.xH_2O$, 77.7 mmole of $CaCl_2.2H_2O$, 35.95 mmole $CrCl_3$, 2.7 mmole of $CCl_3COOH$, 0.16 mmole of copper trifluoroacetylacetonate, 1.74 mmole of $CuCl_2.2H_2O$, 8.6 mmole of $CaBr_2.2H_2O$, 1.126 mmole of Gamma-Cyclodextrin, 0.97 mmole of Hydroxy-Beta-Cyclodextrin, 1.89 mmole of $Na_2PdCl_4$, 23.89 mmole of $PdCl_2$, and 0.55 mmole of Beta-Cyclodextrin. After 1 day of soaking, the excess solution is removed and the sensors are dried using Kimwipe tissue paper. Sensors are spread flat on a clean Pyrex or plastic tray and allowed to dry slowly inside a polyester felt pillowcase inside humidity and temperature controlled room or chamber with relative humidity maintained within 45 to 55% and temperature within 20 to 26° C. After 1 day, the pillowcase is removed and the sensors are allowed to further air dry in the same controlled room for 1 more day. Then the sensor tray is placed inside a 40° C. drying oven for 1 to 2 days. The sensor tray is removed and stored inside the humidity and temperature controlled chamber. The sensors are now ready for test.

Preferred Embodiment 10

Example 11

One preferred embodiment for detecting low concentrations of CO ranging from 5 to 10 ppm CO is shown below in example 11. (MICROSIR Models M1-01e, M1-02e, M3-01e, and M3-02e with S50 Single CO Sensing Element, an aid for early fire detection and elimination of false alarm).

"Soak Method"

600 of the mini-sized silica porous silicate disks with pore diameter ranging from 200 to 300 angstroms and surface area ranging from 100 to 200 square meter per gram are soaked in a 15-mL of the new S50 sensing formulation containing 0.01233965M $H_4SiMo_{12}O_{40}$, 0.001069613M Gamma-Cyclodextrin, 0.00091359 Beta-Cyclodextrin, 0.071898031M, $CaCl_2.2H_2O$, 0.00202082M $CuCl_2.2H_2O$, 0.018073268M $Na_2PdCl_4$, and 0.02876145M $PdCl_2$. After 1 day of soaking, the excess solution is removed and the sensors are dried using Kimwipe tissue paper. Sensors are spread flat on a clean Pyrex or plastic tray and allowed to dry slowly inside a poly-ester felt pillowcase inside humidity and temperature controlled room or chamber with relative humidity maintained within 45 to 55% and temperature within 20 to 26° C. After 1 day, the pillowcase is removed and the sensors are allowed to further air dry in the same controlled room for 1 more day. Then the sensor tray is placed inside a 40° C. drying oven for 1 to 2 days. The sensor tray is removed and stored inside the humidity and temperature controlled chamber. The sensors are now ready for test.

Example 12A

Step 1: Boron Oxide Coating of SPS Using "Soak Method"

100 of 0.230" diameter×0.100" thick silica porous silicate disks with pore diameter ranging from 200 to 300 angstroms and surface area ranging from 100 to 200 square meter per gram are soaked in a 15 mL of boric acid solution with concentrations ranging from 0.001 to 2.0N. After about 1 day of soaking, the excess solution is removed and the SPS disks are dried using Kimwipe tissue paper. Then the disks are spread flat on a clean Pyrex tray to dry inside humidity and temperature controlled room or chamber with relative humidity maintain with 45 to 55% and temperature within 20 to 26° C. The tray and its content are then transferred to an oven where they are heated at 160° C. for several hours then cool to room temperature. The boron oxide coated SPS disks are now ready to be coated with CO sensing material as described in step 2 below.

Step 2: Coating of Boron Oxide SPS with Single Sensing Formulation S66e Using "Soak Method"

The 100 of boron oxide coated SPS disks are immersed in 15 mL of the S66e CO sensing reagent mixture containing 7.87 mmole of $H_4SiMo_{12}O_{40}.xH_2O$, 38 mmole of $CaCl_2.xH_2O$ and 38 mmole of $MnCl_2.xH_2O$ and, 2.7 mmole of $CCl_3COOH$, 0.16 mmole of copper trifluoroacetylacetonate, 1.74 mmole of $CuCl_2.2H_2O$, 8.6 mmole of $ZnBr_2.2H_2O$, 1.126 mmole of Gamma-Cyclodextrin, 0.97 mmole of Hydroxy-Beta-Cyclodextrin, 2.25 mmole of $Na_2PdCl_4$, 23.89 mmole of $PdCl_2$, and 0.55 mmole of Beta-Cyclodextrin. After 1 day of soaking, the excess solution is removed and the sensors are dried using Kimwipe tissue paper. Sensors are spread flat on a clean Pyrex or plastic tray and allowed to dry slowly inside a polyester felt pillowcase inside a humidity and temperature control room or chamber with relative humidity maintained within 45 to 55% and temperature within 20 to 26° C. After 1 day, the pillowcase is removed and the sensors are allowed to further air dry in the same controlled room for 1 more day. Then they are placed inside a 40° C. drying oven for 1 to 2 days. The sensors are subsequently removed and stored inside the humidity and temperature controlled chamber. The sensors are now ready for test.

The new Single-Chemical-Sensing Element detects CO without any power. It functions adequately, by itself, without a reservoir, as a visual indicator for CO in real-world conditions.

However, like the current Dual-Chemical-Sensing-Elements, the new Single-Chemical-Sensing Element with the reservoir is preferred for certain applications such as to meet the stringent requirements in UL 2034 and 2075 as well as CSA6.19-01. Some of the UL test requirements are not real world related such as those described in CRITERION 9 below.

The reservoir, according to a co-pending U.S. patent application titled, "Chemical System for Controlling Relative Humidity and Air Quality," U.S. patent application Ser. No. 10/997,646, filed Nov. 24, 2004, now abandoned, and U.S. Pat. No. 6,251,344 contains a chemical mixture for controlling relative humidity within a specified space.

In these documents, Goldstein et al. and Goldstein describe a means to maintain relative humidity and certain air quality contaminates within a predetermined range for a predetermined period of time within a chamber, which is connected to the atmosphere. The objective is to maintain a specific air quality including relative humidity (RH) within a predetermined range for extended period of time under real-world conditions as well as extreme conditions. The controlled chamber(s) is contained within a housing that has one or more small openings to the atmosphere. The relative humidity control system also comprises at least one opening to a reservoir of chemicals including a salt with water in at least some solid or a solution containing at least some excess solid phase salt. This control system maintains predetermined RH % range within the "Controlled Chamber" for a given temperature range regardless of the humidity variations in the outside environment, even allowing operation in a condensing environments. Either the solid or saturated salts in the reservoir can be isolated from the controlled chamber by means of a hydrophobic membrane. These membranes may include, but not limited to, UPE (a polyethylene membrane manufactured by Millipore of Bedford, Mass.) or Goretex (a Teflon membrane manufactured by W. L. Gore & Associates, Inc.).

These membranes allow water to pass in the gaseous state but not liquid solution or solid. The membrane allows the system to be orientation in any direction, i.e., to be placed in any orientation even with the membrane facing down. The membrane is thermal welded to a supporting grid.

In addition, a getter system is provided which can remove specific airborne contaminants, pollutants, and or warfare agents. The getter can keep items such as chemical sensors to be protected in the controlled environmental chamber, free from contamination and in a specified RH range thus increase its operating life and effectiveness.

Previously, the Dual-CO-Sensing-Elements were used in conjunction with a reservoir system, which contains a mixture of $Mg(NO_3)_2.6H_2O$ and $MgSO_4.7H_2O$. While this mixture enables the Dual-CO-Sensing-Elements to pass the UL 2034 "Sequential Tests," from start to finish, it is unable to successfully allow the new Single-CO-Sensing Element to pass the same sequential testing. The new Single-CO-Sensing Element needs a new improved reservoir system in order to meet the UL 2034 and UL 2075 residential requirements. The reservoir system is detailed in a co-pending U.S. patent application Ser. No. 10/997,646, filed first in Nov. 24, 2004, now abandoned. The new reservoir contains salt of $MnCl_2.4H_2O$ and/or a mixture of $MnCl_2.4H_2O$ and $MnBr_2.4H_2O$ instead of the mixture of $Mg(NO_3)_2.6H_2O$ and $MgSO_4.7H_2O$.

The following criteria were taken from UL 2034, 2nd. Edition, effective Oct. 1, 1998. Criteria 1 through 10 must be carried out in the extract order presented. In order for either the dual or the single CO sensing system to pass, it must be able to pass all four different gas concentrations within the allowed lower and upper time limits at the test conditions as specified by UL's SEQUENTIALLY from Criterion 1 to Criterion 11 without having to replace a sensor component.

Table 7

Various CO Concentrations Vs. Time Limits as Specified Under UL 2034

Shown are Five CO concentrations along with the upper and lower time limits and acceptance criteria. The four CO concentrations can be introduced in any other in a given test condition as long as the order of the test conditions are kept in the "SEQUENCE" from Criteria 1 to 11. The first four are applicable to all 11 criteria below. CO Ramp Test is applicable to Criterion 1.

TABLE 7

| CO ppm | LOWER TIME LIMITS | UPPER TIME LIMITS | ACCEPTANCE CRITERIA |
|---|---|---|---|
| 30 | 8 hr. | 8 hr. | Must not alarm for 8 hours. |
| 70 | 60 min. | 240 min. | Must not alarm before 60 minutes and must alarm by 240 minutes. |
| 150 | 10 min. | 50 min. | Must not alarm before 10 minutes and must alarm by 50 minutes. |
| 400 | 4 min. | 15 min. | Must not alarm before 4 minutes and must alarm by 15 minutes. |
| 0-480 ppm Ramp Test | >19 min. | <30 min. | Ramp CO from 0 to 480 ppm at the rate of 16 ppm per minute. Time response must be after 19 minutes and before 30 minutes. |

Criterion 1: Sensitivity Tests

Preconditioning test samples for 48 hours in a controlled test chamber of about 20-26° C. and about 30-70% RH. After 48 hours, expose the samples to the following CO concentrations. First, expose the samples to 70 ppm CO for 240 minutes, and then regenerate the samples in air for 2 to 4 hours. Second, expose the samples to 150 ppm CO for 50 minutes; next regenerate the samples in air for 4 to 6 hours. Third, expose the samples to 400 ppm CO for 15 minutes, and then regenerate the samples in air for 8 to 16 hours. Fourth, expose the samples to 30 ppm CO for 8 hours. Allow samples to recover in air over night. Then finally, the samples are subjected to a CO ramp test from 0 to 480 ppm by introducing CO into the chamber at the rate of 16 ppm per minute for 30 minutes. At the end of 30 minutes, the CO concentration should be within 480±15 ppm. During the CO ramp up, it is considered acceptable when a CO detector activates an alarm mode after 19 minutes and before 30 minutes.

Criterion 2: Stability Test

The exact same samples from criterion 1 are placed inside an environmental chamber (Thermotron), which is programmed to ramp temperature and percent relative humidity cycling from 23° C. and 55% to 0° C. and 15% RH in 15 minutes and hold at 0° C. and 15% RH for 30 minutes, then ramp up to 49° C. and 15% RH in 15 minutes and hold at 49° C. and 15% RH for 15 minutes. The samples must resist false alarming throughout all 10 cycles between 0° C. and 49° C.

Criterion 3: Sensitivity Test Post Stability Test

The samples from Criteria 2 are preconditioned for 16-24 hours in a controlled test chamber of about 20-26° C. and about 30-70% RH. Then, first expose the samples to 70 ppm CO for 240 minutes, then regenerate the samples in air for 2 to 4 hours. Second, expose the samples to 150 ppm CO for 50 minutes, and then regenerate the samples in air for 4 to 6 hours. Third, expose the samples to 400 ppm CO for 15 minutes, and then regenerate the samples in air for 8 to 16 hours. Fourth, expose the samples to 30 ppm CO for 8 hours Criterion 4: Selectivity Test Inside a test chamber at 20-26° C. and 30-70% RH, the same samples from criterion 3 are to be exposed for 2 hours in each of the following gases with approximately 1 hour of regeneration time in air between gases: 500 ppm methane, 300 ppm butane, 500 ppm Heptane, 200 ppm ethyl acetate, 200 ppm isopropanol, and 5,000 ppm carbon dioxide. Samples must resist false alarming to all of the 6 gases.

Criterion 5: Sensitivity Test Post Selectivity Test

The same samples from Criteria 4 are preconditioned for 16-24 hours in a controlled test chamber of about 20-26° C. and about 30-70% RH. Then, first expose the samples to 70 ppm CO for 240 minutes, then regenerate the samples in air for 2 to 4 hours. Second, expose the samples to 150 ppm CO for 50 minutes, and then regenerate the samples in air for 4 to 6 hours. Third, expose the samples to 400 ppm CO for 15 minutes, and then regenerate the samples in air for 8 to 16 hours. Fourth, expose the samples to 30 ppm CO for 8 hours.

Criterion 6: Sensitivity Test During 49° C. and 40% RH

The same samples from Criteria 5 are preconditioned for 3 hours in a controlled test chamber of about 49° C. and about 40% RH. Then, first expose the samples to 70 ppm CO for 240 minutes, then regenerate the samples in air for 2 to 4 hours. Second, expose the samples to 150 ppm CO for 50 minutes, and then regenerate the samples in air for 4 to 6 hours. Third, expose the samples to 400 ppm CO for 15 minutes, and then regenerate the samples in air for 8 to 16 hours. Fourth, expose the samples to 30 ppm CO for 8 hours.

Criterion 7: Sensitivity Test During 0° C. and 15% RH

The same samples from Criteria 6 are preconditioned for 3 hours in a controlled test chamber of about 0° C. and about 15% RH. Then, first expose the samples to 70 ppm CO for 240 minutes, then regenerate the samples in air for 2 to 4 hours. Second, expose the samples to 150 ppm CO for 50 minutes, and then regenerate the samples in air for 4 to 6 hours. Third, expose the samples to 400 ppm CO for 15 minutes, and then regenerate the samples in air for 8 to 16 hours. Fourth, expose the samples to 30 ppm CO for 8 hours.

Criteria 8: Shipping and Storage Test

The exact same samples from criterion 7 are placed inside an environmental chamber, which is programmed to ramp temperature and percent relative humidity cycling from 23° C. and 55% to 70° C. and 40% RH in 3 hours and hold at 70° C. and 40% RH for 24 hours, then ramp down to minus (−) 40° C. and 15% RH in 3 hours and hold at minus (−) 40° C. and 15% RH for 3 hours. The samples must resist false alarming throughout the test duration.

Criterion 9: Sensitivity Test Post Shipping & Storage Test

The same samples from Criteria 8 are preconditioned for 16-24 hours in a controlled test chamber of about 20-26° C. and about 30-70% RH. Then, first expose the samples to 70 ppm CO for 240 minutes, then regenerate the samples in air for 2 to 4 hours. Second, expose the samples to 150 ppm CO for 50 minutes, and then regenerate the samples in air for 4 to 6 hours. Third, expose the samples to 400 ppm CO for 15 minutes, and then regenerate the samples in air for 8 to 16 hours. Fourth, expose the samples to 30 ppm CO for 8 hours.

Criteria 10: Sensitivity Test During 52° C. and 95% RH

The same samples from Criteria 9 are preconditioned for 168 hours at 52° C. and 95% RH in an environmental chamber. After samples resist false alarming for 168 hours, they are to be exposed to the following CO concentrations. First expose the samples to 70 ppm CO for 240 minutes, and then regenerate the samples in air for 16 to 24 hours. Second, expose the samples to 150 ppm CO for 50 minutes, and then regenerate the samples in air for 16 to 24 hours. Third, expose the samples to 400 ppm CO for 15 minutes, and then regenerate the samples in air for 24 to 48 hours. Fourth, expose the samples to 30 ppm CO for 8 hours.

Criteria 11: Sensitivity Test During 23° C. and 15% RH

The same samples from Criteria 10 are preconditioned for 168 hours at 23° C. and 15% RH in an environmental chamber. After samples resist false alarming for 168 hours, they are to be exposed to the following CO concentrations. First expose the samples to 70 ppm CO for 240 minutes, and then regenerate the samples in air for 16 to 24 hours. Second, expose the samples to 150 ppm CO for 50 minutes, and then regenerate the samples in air for 16 to 24 hours. Third, expose the samples to 400 ppm CO for 15 minutes, and then regenerate the samples in air for 16 to 24 hours. Fourth, expose the samples to 30 ppm CO for 8 hours.

Criteria 12A: Sensitivity Test During 22±3° C. and 10±3% RH

This new UL 2034 requirement went into effect on Mar. 8, 2007. It will replace the current criterion 11 above. Like the current criteria 11, the same samples from Criteria 10 are preconditioned for 168 hours at 23° C. and 10±3% RH in an environmental chamber. After samples resist false alarming for 168 hours, they are to be exposed to the following CO concentrations. First expose the samples to 70 ppm CO for 240 minutes, and then regenerate the samples in air for 16 to 24 hours. Second, expose the samples to 150 ppm CO for 50 minutes, and then regenerate the samples in air for 16 to 24 hours. Third, expose the samples to 400 ppm CO for 15 minutes, and then regenerate the samples in air for 16 to 24 hours. Fourth, expose the samples to 30 ppm CO for 8 hours.

The present invention is useful for the detection of carbon monoxide from fires, automobiles, appliances, motors, and other sources. Unlike the DUAL CO sensing system disclosed in U.S. Pat. No. 5,618,493, only a SINGLE sensing element is needed to meet UL 2034 and UL 2075 requirements for residential and commercial applications, respectively. The single sensing element also has long functional life of at least 10 years, when the SPS substrate is first coated with boron oxide before they are coated with the S6 or S66 formulation series. It costs less than the dual sensing system; and is also very CO specific. In addition, it is also self-calibrated. The comparative data, which verify these statements, are shown in Tables 8 and 9 as well as FIGS. 29, 30, 31, and 32.

Criteria 12B: Sensitivity Test During 22±3° C. and 7.5±5% RH

Similar to Criterion 12A for UL 2034, UL 2075 requires for low humidity to 7.5±0.5% RH at 22±3° C. It replaced the current criteria 11 above, effective Mar. 8, 2007. UL 2075 applies to CO alarms used in "system detection" application. Like the current criteria 11, the same samples from Criteria 10 are preconditioned for 168 hours at 22° C. and 7.5±0.5% RH in an environmental chamber. After samples resist false alarming for 168 hours, they are to be exposed to the following CO concentrations. First expose the samples to 70 ppm CO for 240 minutes, and then regenerate the samples in air for no more than 16 hours. Second, expose the samples to 150 ppm CO for 50 minutes, and then regenerate the samples in air for not more than 16 hours. Third, expose the samples to 400 ppm CO for 15 minutes, and then regenerate the samples in air for not more than 16 hours. Fourth, expose the samples to 30 ppm CO for 8 hours.

Table 8

Various NEW mini-sized "Single CO Sensing Elements", manufactured according to examples 1B, 2B, 3B, and 4B, were compared against the current regular-sized "Dual CO Sensing Elements." All samples are assembled with reservoirs containing $MnCl_2$ and or $MnBr_2$. All samples were on 9SIR-MICROSIR PCB boards. Comparison was based on Criteria 1, 6, and 7. "+" indicate "great than or equal to 90% passing rate" for all of the CO concentrations and time limits shown in Table 1. "−" Indicates "below 90% passing rate."

| SENSOR TYPE | DISK Size OD × Thickness Inches | APPLICABLE EXAMPLE | CRITERION 1 55% RH/23° C. | CRITERION 6 40%/RH/49° C. | CRITERION 7 7%/RH/23° C. |
|---|---|---|---|---|---|
| S6e one small disk | 0.100 × 0.05 | 1B | + | + | + |
| S66e one disk | 0.100 × 0.05 | 2B | + | + | + |
| S66e one disk | 0.100 × 0.05 | 3B | + | + | + |
| S66L one disk | 0.230 × 0.105 | 4B | + | + | + |
| S34 Two disks | 0.230 × 0.100 | Current S34 | + | + | − |

Table 9

Various NEW mini-sized "Single CO Sensing Elements", manufactured according to examples 1B, 2B, 3B, and 4B, were compared against the current regular-sized "Dual CO Sensing Elements." All samples are assembled with reservoirs containing $MnCl_2$. All samples were on 9SIR-MICRO-SIR PCB boards. Comparison was based on Criteria 10, 11, and 12. "+" Indicates "great than or equal to 90% passing rate" for all of the CO concentrations and time limits shown in Table 1. "−" Indicates "below 90% passing rate."

TABLE 9

| SENSOR TYPE | DISK QTY | APPLICABLE EXAMPLE | CRITERION 10 95% RH/52° C. | CRITERION 11 15% RH/23° C. | CRITERION 12 7% RH/23° C. |
|---|---|---|---|---|---|
| S6e | 1 | 1B | + | + | + |
| S66e | 1 | 2B | + | + | + |
| S66e | 1 | 3B | + | + | + |
| S66Lb | 1 | 4B | + | + | + |
| S34 | 2 | Current S34 | + | + | − |

Preferred Embodiments Versus Applications

Example 2B is highly preferred in MICROSIR application for meeting UL 2034 or CSA 6.19-01 and UL2075 residential application. This is single sensing element formulation S66e.

Example 4A is best for SIR application for meeting UL 2034 or CSA 6.19-01 residential and UL 2075 commercial applications (all conditioned space). This is the single sensing element formulation S66L.

Example 4A+Example 5A combined, are highly preferred for SIR application for meeting UL 2034 for "Recreational Boating," application.

Example 4B is preferred for MICROSIR application to meet UL 2034 or CSA 6.19-01 for "Recreational Vehicle" application.

Examples 1A, 2A, or 4A, is best for CO Visual Indicator application. Below is the confirmed, comparative performances of Quantum Eye's 34t and S6e performance. The sensitivity of S66e and S66L are greater than that of S6e.

The SECOND application for the NEW "Single CO Sensing Element," is LOW COST VISUAL INDICATOR for CO. It is preferred that the regular-sized disks are used for this applicable for better visual effect. As stated above, the new Single CO Sensing Element functions as a VISUAL COLOR indicator for WARNING the end users the presence of CO. It provides the LOW-COST alternative for protecting human life against the danger of CO poisoning.

Currently, there are three (3) different visual color indicators for CO commercially available. First is the "QUANTUM EYE", a visual Co detector that changes color to indicate a CO hazard, which is manufactured according to U.S. Pat. No. 5,063,164, by QUANTUM GROUP INC., located in San Diego, Calif. Second is the "DEAD STOP," which manufactured in Denmark for J L SIMS COMPANY, INC. located in St. Louis, Mo. Third is "AIR ZONE," which is supplied by ENZONE Inc. located in Davie, Fla.

Currently, "Quantum Eyes" are made with sol-gel substrates, which are manufactured by GEL-TECH in Orlando, Fla. These substrates are very costly due to low manufacturing yields, which result from poor mechanical strength. The present invention provides low cost visual CO detectors called the "S6e" sensor series, which are mechanically strong. Initially, S6e appears tan-orange and turns dark blue upon exposure to danger levels of CO, i.e. 70 ppm and above. S6e Quantum Eye® returns to its initial color after CO is removed. S6e Quantum Eyes fail-safe as they will become more and more sensitivity towards CO after have repeatedly re-exposed to CO 50 to 100 times.

While there are no regulatory standards that govern visual CO indicators, the new S6e Quantum-Eye out-performed DEAD STOP and AIR ZONE under a wider range of temperature and relative humidity such as −40° C. to +70° C. and 25 to 95% RH as well as meeting the OSHA limits by NOT changing colors at 50 ppm CO for 8 hours. Changing COLOR in response to 50-ppm CO is considered to be "false-alarming". The new "S6e Quantum-Eye" has long functional life and is self-regenerated. It is cost effective and is very CO specific.

The comparative data, which verifies these statements, are shown in Tables 10-13 below.

According to the Coburn's equation for determining the effect of CO poisoning in human at different levels of percentage carboxyhemoglobin (% COHb) in the blood, the exposure to 200 ppm CO at various exposure times yields the following symptoms: 1) 35 minutes equals 10% COHb (no effect), 2) 60 minutes equals 15% COHb (slight headache), and 90 minutes equals 20% COHb (Headache).

For CO Sensitivity Test, a visual CO indicator must indicate CAUTION within 60 minutes and DANGER within 90 minutes when exposed to 200 ppm CO to be considered "pass" or "+". Any visual CO indicator that cannot meet these criteria would be considered "fail" or "−".

For Resistance to Low CO Concentration Test, a visual CO indicator must NOT change color to indicator neither CAUTION nor DANGER when exposed to 50 ppm CO for 8 hours.

Table 10

CO Sensitivity Test Comparison at Variable Ambient Relative Humidity and Room Temperature Test Two visual CO indicators each were randomly chosen from the groups of the new S6e Quantum Eyes, 34t Quantum Eyes, Dead-Stop, and Air-Zone. They were placed inside a test chamber and allowed to equilibrate for 24 to 48 hours at each test condition before they were exposed to 200 ppm CO for 90 minutes. Each unit must indicate "CAUTION" within 60 minutes to be considered pass (+) and a "DANGER" within 90 minutes to be considered pass (+) at each test conditions. Unit that failed to meet these criteria were considered to be failing (−). S6e Quantum Eyes and 34t Quantum Eyes are the only two groups that could pass all three-test conditions.

TABLE 10

| Samples | 20° C. & 7% RH 24 Hr. | | 20° C. & 53% RH 24 Hr. | | 20° C. & 90% RH 48 Hr. | |
|---|---|---|---|---|---|---|
| | CAUTION | DANGER | CAUTION | DANGER | CAUTION | DANGER |
| S6e Quantum Eyes | + | + | + | + | + | + |
| 34t Quantum Eyes | + | − | + | + | + | + |
| Dead-Stop | − | − | + | + | + | + |
| Air-Zone | − | − | + | + | + | + |

Table 11

Comparison of Low CO Level Resistance—Variable Ambient Relative Humidity/Room Temperature Test Two visual CO indicators each of the Model types S6e Quantum Eyes, 34t Quantum Eyes, Dead-Stop, and Air-Zone were placed inside a test chamber and allowed to equilibrate for 15 to 20 minutes at each test condition. Then, they were exposed to 50-ppm CO for 8 hours. (+)=unit that PASSED by NOT indicating the 50 ppm-CO for the entire 8 hours.

TABLE 11

| TEST CONDITION | 20° C. & 33% RH | 20° C. & 53% RH | 20° C. & 67% RH |
|---|---|---|---|
| S6e Quantum Eyes | + | + | + |
| 34t Quantum Eyes | − | − | − |
| Dead-Stop | − | − | − |
| Air-Zone | + | + | + |

Table 12

Comparative of Sensitivities—Variable Ambient Relative Humidity/High Temperature Test Two visual CO indicators each were randomly chosen from the groups of S6e Quantum Eyes, 34t Quantum Eyes, Dead-Stop, and Air-Zone. They were placed inside a Thermotron environmental test chamber and allowed to equilibrate for 1 to 48 hours as specified in the Table below. While at each test condition, they were exposed to 200 ppm CO was for 90 minutes. "+"=unit that indicated the "CAUTION" within 60 minutes and/or "DANGER" within 90 minutes. "−"=unit that failed to indicate "CAUTION" within 60 minutes and/or "DANGER" within 90 minutes. S6e Quantum Eyes and 34t Quantum Eyes are the only two groups that met these requirements.

TABLE 12

| Samples | 40° C. & 40% RH 3 Hr. Conditioning | | 70° C. & 40% RH 1 Hr. Conditioning. | | 50° C. & 95% RH 48 Hr. Conditioning | |
|---|---|---|---|---|---|---|
| | CAUTION | DANGER | CAUTION | DANGER | CAUTION | DANGER |
| S6e Quantum Eyes | + | + | + | + | + | + |
| 34t Quantum Eyes | + | + | + | + | + | + |
| Dead-Stop | − | − | − | − | + | + |
| Air-Zone | − | − | − | − | + | + |

(−)=unit that failed because they indicate the presence of 50-ppm CO when they were not supposed to. Only S6e Quantum Eyes and Air-Zone pass this test. However, Air-Zone had already failed the sensitivity comparison test as described in Table 10.

Table 13

Comparison of CO Sensitivity-Low Relative Humidity/Low Temperature Test

Two visual CO indicators each were randomly chosen from the groups of S6e Quantum Eyes, 34t Quantum Eyes, Dead- Stop, and Air-Zone. They were placed inside a Thermotron environmental test chamber and allowed to equilibrate to each test condition for 3 hours to reach thermal equilibrium. While at each test condition, they were exposed to 200 ppm CO was for 90 minutes. "+"=unit that indicated "CAUTION" within 60 minutes and/or "DANGER" within 90 minutes. "−"=unit that failed to indicate "CAUTION" within 60 minutes and/or "DANGER" within 90 minutes. S6e Quantum Eyes and 34t Quantum Eyes are the only two groups that met these requirements.

TABLE 13

| Sample Descriptions | 0° C. & 7% RH 3 Hr. | | Minus (−) 40° C. 3 Hr. | |
|---|---|---|---|---|
| | CAUTION | DANGER | CAUTION | DANGER |
| S6e Quantum Eyes | + | + | + | + |
| 34t Quantum Eyes | + | − | + | + |
| Dead-Stop | − | − | − | − |
| Air-Zone | − | − | − | − |

The THIRD application for the NEW "Single CO Sensing Element," is DIGITAL CO ALARMS. When the NEW mini-sized S6e and S66e series were enclosed in the MICROSIR reservoirs assembly and then tested on yet another newly invented printed circuit board, which is a subject of another co-pending patent application titled, "Digital Gas Detector and Noise Reduction Techniques", U.S. patent application Ser. No. 12/254,799 (Publication No. 2009/0043515, Published Feb. 12, 2009, now abandoned), which Gonzales describes a set of equations that convert and correlate the NEW sensor responses to CO ppm on LCD display. The results from the first prototype digital CO alarm using a single CO sensing element were encouraging and are shown in Tables 14 and 15.

Table 14
Comparison of LCD Display in Terms of PPM CO at Ambient Relative Humidity/Ambient Temperature Test Quantum's prototype MICROSIR digital CO alarm versus display the actual CO concentration as indicated by a Dräger Pac-III (electrochemical based sensor, manufactured by Dräger Inc., can be purchased for about $3,000 US dollars). Quantum's prototype MICROSIR digital CO alarm comprised Quantum's new "single CO sensing element" type S66L on the new electronic board and software. According to UL 2034, the limits for 70-ppm CO are from 60 to 240 minutes. It is highly preferred that an LCD display does NOT show any CO concentration for the first 59 minutes at this concentration to prevent premature WARNING to the end users; hence, reducing false alarm. Therefore, the fact that MICROSIR CO alarm did not display CO concentration for first 6 minutes is actually a good thing. The accuracy of the prototype MICROSIR digital CO alarm was within ±13% in 70 ppm CO, after 9 minutes without any calibration.

Table 14 Continued
Comparison of LCD Display in Terms of PPM CO at Ambient Relative Humidity and Ambient Temperature Test

TABLE 14

| Elapsed Time (Min.) | Reference CO Conc. (ppm) | Prototype MICROSIR Digital CO Alarm With S66L Single Sensing Element |
|---|---|---|
| 0 | 0 | 0 |
| 1 | 69 | 0 |
| 2 | 71 | 0 |
| 3 | 71 | 0 |
| 4 | 71 | 0 |
| 5 | 71 | 0 |
| 6 | 71 | 0 |
| 7 | 71 | 0 |
| 8 | 70 | 70 |
| 9 | 70 | 70 |
| 10 | 71 | 75 |
| 11 | 70 | 75 |
| 12 | 70 | 77 |
| 13 | 70 | 77 |
| 14 | 70 | 79 |
| 15 | 70 | 79 |
| 16 | 70 | 79 |
| 17 | 70 | 79 |
| 18 | 70 | 78 |
| 19 | 70 | 78 |
| 20 | 70 | 74 |
| 21 | 70 | 74 |
| 22 | 69 | 74 |
| 23 | 69 | 74 |
| 24 | 71 | 71 |
| 25 | 70 | 71 |
| 26 | 70 | 70 |
| 27 | 70 | 70 |

Table 15
Comparison of LCD Display in Terms of PPM CO at Ambient Relative Humidity and Ambient Temperature Test Quantum's prototype MICROSIR digital CO alarm versus display the actual CO concentration as indicated by a Dräger Pac-III (electrochemical based sensor, manufactured Dräger Inc., can be purchased for about $3,000 US dollars). Quantum's prototype MICROSIR digital CO alarm comprised Quantum's new "single CO sensing element" type S66L on the new electronic board and software. According to UL 2034, the limits for 150-ppm CO are from 10 to 50 minutes. It is highly preferred that an LCD display does NOT show any CO concentration for the first 9 minutes at this concentration to prevent premature WARNING to the end users; hence, reducing false alarm. Therefore, the fact that MICROSIR CO alarm did not display CO concentration for first 4 minutes is actually a good thing. The accuracy of the prototype MICROSIR digital CO alarm was within ±10% in 150-ppm CO after the first 9 minutes.

TABLE 15

| Elapsed Time (Min.) | Reference CO Conc. (ppm) | Prototype MICROSIR Digital CO Alarm With S66L Single Sensing Element |
|---|---|---|
| 0 | 0 | 0 |
| 1 | 120 | 0 |
| 2 | 145 | 0 |
| 3 | 150 | 0 |
| 4 | 150 | 0 |
| 5 | 150 | 101 |
| 6 | 149 | 101 |
| 7 | 150 | 126 |
| 8 | 151 | 163 |
| 9 | 151 | 163 |
| 10 | 151 | 143 |
| 11 | 151 | 145 |
| 12 | 151 | 146 |
| 13 | 150 | 143 |
| 14 | 150 | 137 |
| 15 | 151 | 137 |
| 16 | 150 | 153 |
| 17 | 150 | 153 |

Table 16A & 16B

Electrical Rating or Response Outputs in volt per hour (Table 16A) or in [(Percent Light Obscuration per Hour (% Obs/hr), TABLE 16B] of mini-sized sensing elements type S66 (single sensing element: Models M1-01 & M3-02) and S34 (two sensing elements: Models M1-02 and M3-02) to 0, 15, 70, 150, and 400 ppm CO at Ambient Relative Humidity and Ambient Temperature of 50±20% RH and 23±3° C. These MICROSIR CO Sensor Models were approved by UL on Jan. 17, 2007 as UL Recognized Components: FTAM2 "GAS AND VAPOR DETECTORS AND SENSORS," File E186246 Vol. 3, Sec. 1. All 4 Models undertook a 1-year—stability study with a constant exposure to 15±3 ppm CO in air at 50±20% RH and 23±3° C. The response output to 70, 150, and 400 ppm CO were measured at 50±20% RH and 23±3° C. before and after the 1-year exposure to 15 ppm CO.

TABLE 16A

MICROSIR Response Output in Voltage Change in Volt per Hour
TABLE 16A. MICROSIR Response Output in Voltage Change in Volt per Hour

| Model | 0 PPM Volt/hr | 15 PPM volt/hr. | 70 PPM volt/hr. | 150 PPM volt/hr. | 400 volt/hr. |
|---|---|---|---|---|---|
| M1-01 | (0.004)-0.007 | (0.002)-0.0083 | 0.11-2.54 | 0.70-10.45 | 1.75-29.09 |
| M1-02 | (0.004)-0.007 | (0.002)-0.0083 | 0.01-0.78 | 0.25-8.40 | 0.91-31.48 |
| M3-01 | (0.004)-0.007 | (0.002)-0.0083 | 0.07-3.10 | 0.61-10.43 | 0.99-36.10 |
| M3-02 | (0.004)-0.007 | (0.002)-0.0083 | 0.004-0.99 | 0.44-7.55 | 1.57-28.80 |

TABLE 16B

MICROSIR Response Output in Percent Light Obscuration per Hour (% Obs/hr)

| Model | 0 PPM % Obs/hr | 15 PPM % Obs/hr | 70 PPM % Obs/hr | 150 PPM % Obs/hr | 400 % Obs/hr |
|---|---|---|---|---|---|
| M1-01 | (0.18)-0.45 | (0.065)-0.28 | 3.7-84.83 | 23.50-348.39 | 52.37-969.74 |
| M1-02 | (0.14)-0.45 | (0.065)-0.28 | 0.24-26.02 | 8.24-279.85 | 30.46-1049.30 |
| M3-01 | (0.14)-0.45 | (0.65)-0.28 | 2.25-103.17 | 20.28-347.63 | 32.96-1203.30 |
| M3-02 | (0.14)-0.45 | (0.65)-0.28 | 0.13-33.06 | 14.75-251.81 | 52.25-959.94 |

FIGS. 1A and 1B illustrate an embodiment of a sensor system 100 for sensing a target gas, including carbon monoxide (CO). The system comprises a housing 106, for example, of molded plastic, configured with a controlled sensor chamber 111 and a treatment chamber 110, wherein the housing defines a gas path that routes air from outside the housing through the treatment chamber before it reaches the sensor chamber 111. The sensor chamber 111 stores a gas sensor 105 reactive to the target gas for detecting the presence of at least a threshold level of the target gas in the air, wherein the treatment chamber 110 advantageously treats the air with at least one treatment component before the air reaches the sensor 105. The treatment component thus effectively controls the environment and atmosphere inside the treatment chamber 110 and the sensor chamber 111 so as to maintain effectiveness of the sensor 105 under normal and extreme operating conditions thereby prolonging the life of the sensor 105. In one embodiment, a total volume or "micro-environment" provided by the treatment chamber 110 and the sensor chamber 111 ranges between about 1.8 cubic cm and 2.0 cubic cm. Advantageously, the controlled sensor chamber 111 increases sensor performance under extreme conditions such as to meet selected Standards set forth by Underwriters Laboratories, Inc. (UL), including UL 2034 (The Standard of Safety for Single and Multiple Station Carbon Monoxide Alarms) and UL 2075 (The Standard of Safety for Gas and Vapor Detectors and Sensors).

In accordance with a feature of the present invention, the treatment components of the system 100 include a reservoir assembly 101 and a getter 103. The reservoir assembly 101 contains a chemical humidity control substance (or mixture of chemical substances) 115 that serves to increase or decrease moisture levels (or donate or draw moisture) so as to maintain relative humidity between about 15% and 90% in the controlled sensor chamber 111. The getter 103 serves to remove or absorb basic gases (such as ammonia and amines) and harmful volatile organic compounds (VOCs) (such as terpenes, and unsaturated chlorinated compounds, including PERC and 1-1-1Trichloroethylene).

The system 100 also includes a sensor detection assembly 117 to enable optical sensing of the presence of at least a threshold level or concentration of the target gas such as the levels required by UL 2034, for example, about 30 ppm for 30 days no response, at 70 ppm respond between 60 minute and 240 minutes, at 150 ppm respond between 10 and 50 minutes, and at 400 ppm respond between 4 and 15 minutes. With the application of circuitry and software provided on a circuit board 136 on which the housing 101 is mounted, an alarm (not shown) is triggered upon detection of a threshold exposure of the target gas, such as CO.

Figure 2:
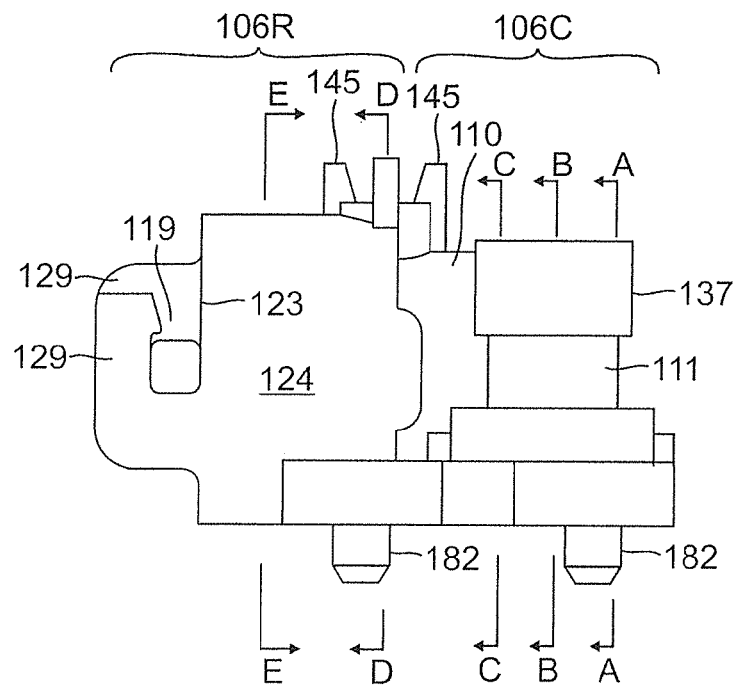
FIG. 2 is a side elevational view of the system 100 as assembled, in accordance with another embodiment of the present invention, including crown formations.
Figure 3:
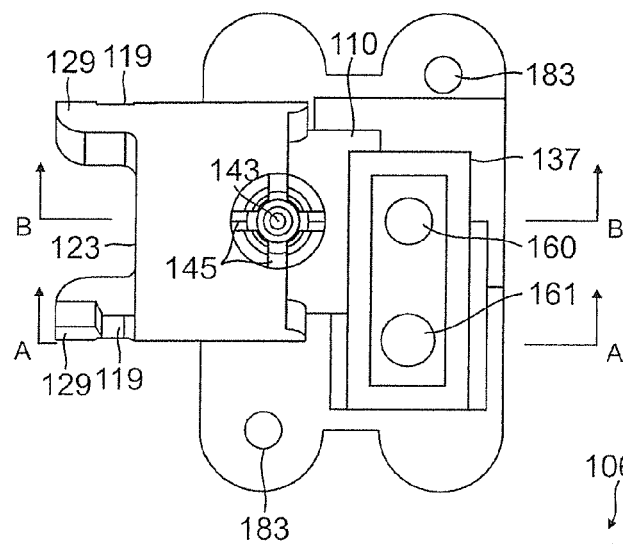
FIG. 3 is a top plan view of the system of FIG. 2.
Figure 3A:
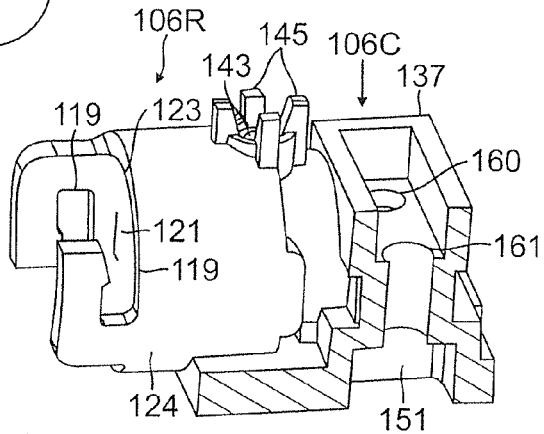
FIG. 3A is a side cross-sectional view of the system of FIG. 3, taken along line A-A.
Figure 3B:
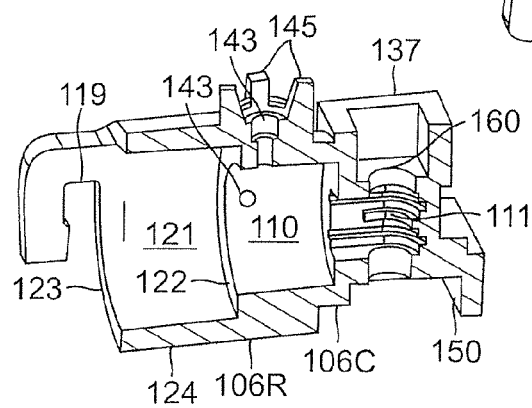
FIG. 3B is a side cross-sectional view of the system of FIG. 3, taken along line B-B.

With reference to FIGS. 2 and 3B, the housing 106 includes a receiving portion 106R at one end, a chamber portion 106C at another end and a base member or plate 106B extending primarily from the chamber portion 106C. The chamber portion includes the treatment chamber 110, the sensor chamber 111, and the sensor detection assembly 117. The treatment chamber 110 is situated between the receiving portion 106R and the sensor chamber 111 such that the treatment chamber 110 connects the receiving portion 106R and the chamber portion 106C and allows fluid or gaseous communication therebetween. As best seen in FIGS. 1B and 1C, the sensor detection assembly 117 is situated around the sensing chamber 111 and the sensor 105.

The receiving portion 106R includes the reservoir assembly 101 and a gasket 102. The receiving portion is configured with a cavity 121 and an opening 123 leading into the cavity 121 in which the reservoir assembly 101 is inserted. The cavity 121 of the receiving portion 106R has a configuration that is closely matched in size and shape by the reservoir assembly 101 so that the cavity 121 and the opening 123 are fully occupied by the reservoir assembly 101 when the reservoir assembly is locked in the receiving portion. In the illustrated embodiment herein, both the receiving portion 106R and the reservoir assembly 101 have a cylindrical form. The receiving portion 106R has a tubular side wall 124 defining the cavity 121. The reservoir assembly 101 has a cylindrical container or drum with an interior volume defined by a tubular side wall 125 that is enclosed at an inner end by a circular end wall 126 and at an outer end by a welded circular lid 113. Sealed inside the reservoir assembly 101 are the chemical substance(s) 115 including humidity-controlling substances, for example, a salt water solution, where the solution is saturated or supersaturated with solid particles.

With reference to FIG. 1A, the end wall 126 has a grid portion with apertures 127 which are covered by a hydrophobic membrane 128 that is welded or otherwise affixed to an inside surface of the end wall 126. The hydrophobic membrane 128 prevents penetration of liquids and solids and thus serves to contain the liquid mixture and solution 115 inside the reservoir assembly 101 while allowing free exchange of gases and vapors between reservoir assembly 101, the treatment chamber 110 and especially the sensor chamber 111 where the sensor 105 is located. In one embodiment, the chemical substance(s) include UV and visible (e.g., dark blue) chemical dyes so that leakage of water or the chemical substance(s) from the reservoir assembly can be readily detected in a quality control test.

The reservoir assembly 101 is configured for releasable engagement with the receiving portion 106R. In the disclosed embodiment, an outer surface of the tubular side wall 125 of the reservoir assembly 101 has locking projection pins or ears 120 that upon rotation of the reservoir assembly engage with radial locking arms 129 and grooves 119 formed at the opening 123 of the receiving portion 106R of the housing 106. As such, the reservoir assembly 101 can be released from the housing 106 so that any of the reservoir assembly 101, the gasket 102, the getter 103, a shock absorber 104 and the sensor 105 can be replaced as needed.

Figure 2A:
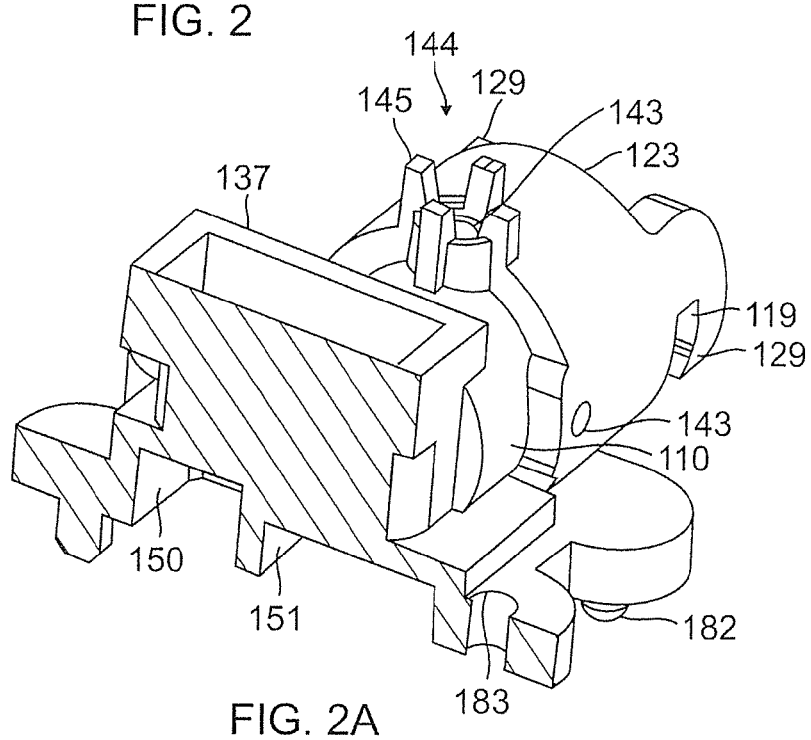
FIG. 2A is an end cross-sectional view of the system of FIG. 2, taken along line A-A.
Figure 2B:
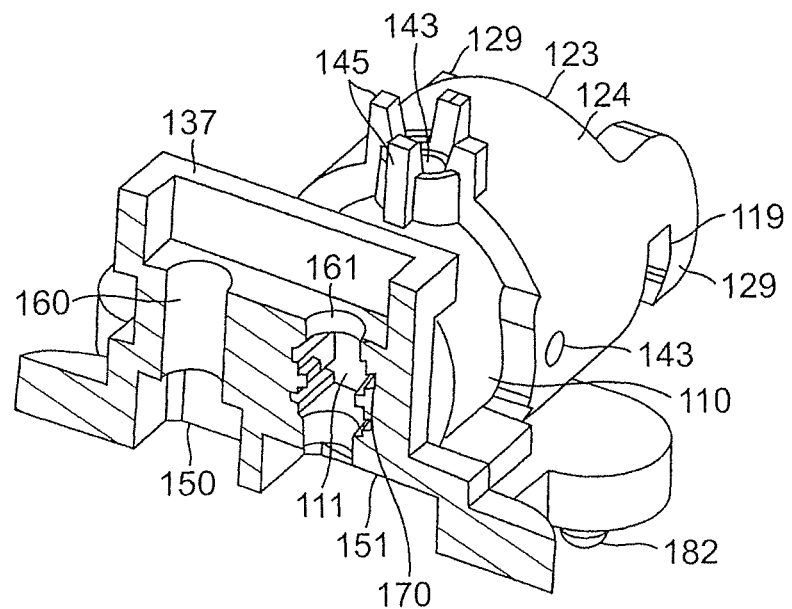
FIG. 2B is an end cross-sectional view of the system of FIG. 2, taken along line B-B.
Figure 2C:
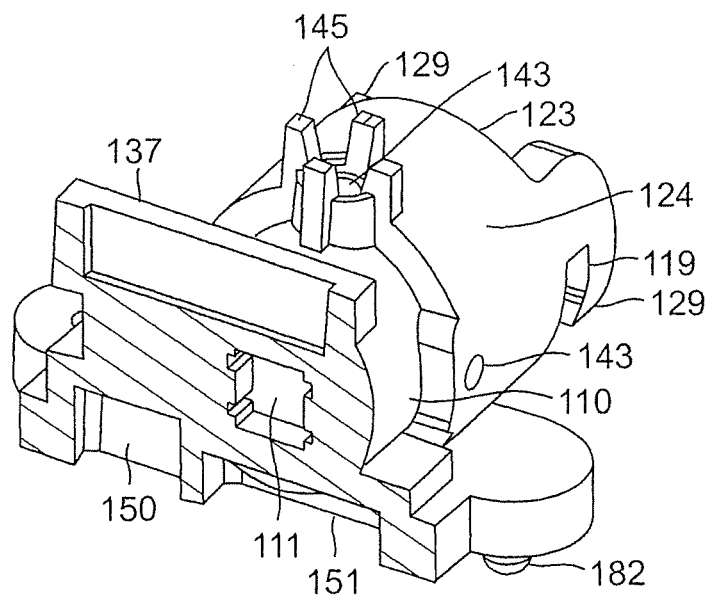
FIG. 2C is an end cross-sectional view of the system of FIG. 2, taken along line C-C.
Figure 2D:
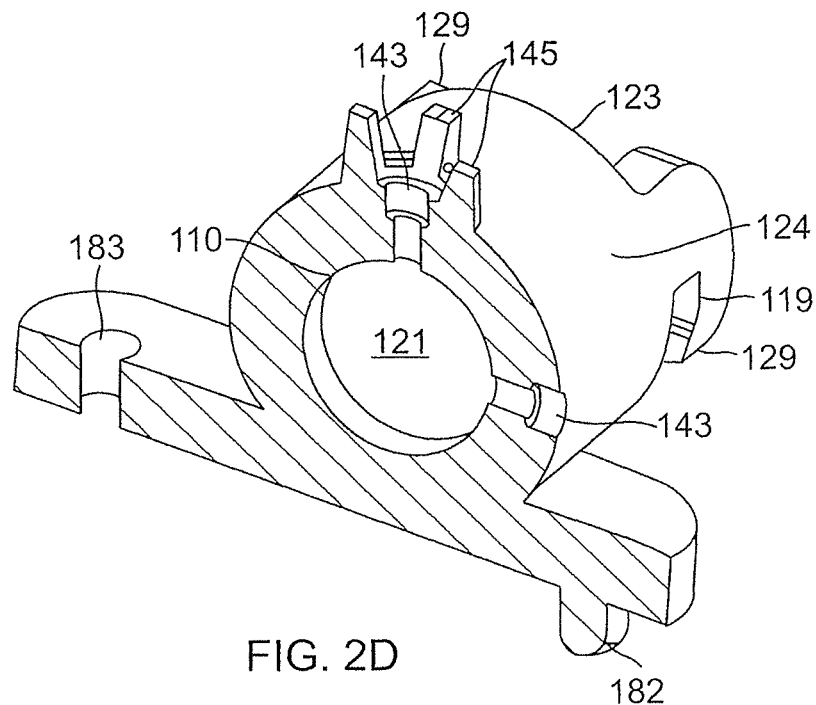
FIG. 2D is an end cross-sectional view of the system of FIG. 2, taken along line D-D.
Figure 2E:
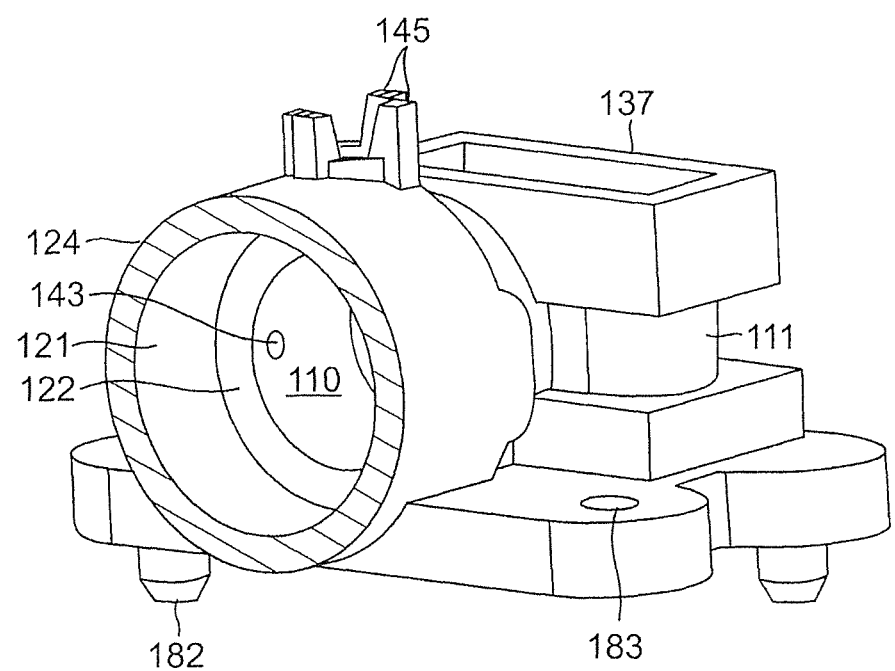
FIG. 2E is an end cross-sectional view of the system of FIG. 2, taken along line E-E.

With reference to FIG. 2E, the treatment chamber 110 connecting the receiving portion 106R and the chamber portion 106C extends linearly in alignment with the reservoir assembly 101 along a longitudinal axis 114 defined by a length of the housing 106. The receiving portion, the treatment chamber 110 and the sensor chamber 111 are generally on-axis (or centered) with each other along the axis 114, although the treatment chamber 110 has a lesser cross-section (or diameter) than the cavity 121 such that an annular flange or seal 122 is advantageously formed therebetween against which the gasket 102 abuts to seal the treatment chamber 110 when the reservoir assembly 101 is received in the cavity 121 and locks when properly engaged with the receiving portion 106R.

The sensor chamber 111 has a significantly lesser cross-section than the treatment chamber 110. In this illustrated embodiment of FIG. 3B, the cross-section or diameter of the sensor chamber 111 is generally closely conforming in size and shape to the sensor 105. As such, the system operates with improved efficiency, for example, by requiring fewer chemicals, including the chemical(s) 115 of the reservoir assembly 101, and the chemicals of the sensor which are reduced by about 25 times in the case of the single sensor as an example of the quantity, which is an improvement in the economics. Consequently, the size of the housing 106 is also minimized for a more aesthetic and smaller profile which is desirable especially for ceiling-mounted alarms, for personal alarm, RV alarms and others. The size of the sensor chamber 111 relative to the sensor 105 is predetermined so as to balance the aforementioned advantages with the need to provide sufficient air circulation in the chamber 111, for example, for the target gas (e.g, CO) to diffuse in and gas products (e.g., CO2) to diffuse out.

In the disclosed embodiment, the sensor chamber 111 is a molded cavity, and the cavity and the sensor 105 are both disk-shaped, having a circular cross-section with a closely conforming predetermined depth or thickness. In that regard, a sensor disk has two circular faces and a circumferential edge, and may be oriented in "face view" (with a face exposed) or "edge view" (with the edge exposed) in relation to a structure. It is understood that the terms "sensor" and "sensor disk" are used interchangeably herein. It is also understood that one or more sensor disks may be used in a system. The treatment chamber 110 is immediately adjacent and directly leads to the sensor chamber 111 which is configured to support the sensor 105 in a predetermined orientation. Where more than one sensor disk is used, a predetermined gap is provided between the disks to allow for air circulation.

In the illustrated embodiment, the sensor detector assembly 117 includes a light-pipe member 116 (better seen in FIGS. 1B and 1C) that is housed in a rectangular optics chamber 137 immediately adjacent the sensor chamber 111. The optics chamber 137 is sealed by the light-pipe member 115, a lid 107 and an O ring 109 which is mounted on the light-pipe. The light-pipe member 116 defines a U-shaped (including, e.g., trapezoidal) optical path with a longer first linear section 116L for receiving light (used interchangeably with "photons" or "beam of photons") from one direction 138, a shorter second linear section 116S for passing light in an opposite direction 139, and a linear mid-section 116M with angled reflective surfaces 198 and 199 connecting the first and second sections 116L, 116S for completing the U-shaped path. The light pipe has an entry end 130, an exit end 131. The reflective surface 198 redirects photons entering at the entry end 130 and traveling through the section 116L along direction 138 toward the mid-section 116M along a direction generally orthogonal to the direction 138. The reflective surface 199 then redirects the photons toward the section 116S along the direction 139 where they exit the exit end 131 and strike the sensor 105. The light-pipe member is arranged in the assembly 117 so that the entry end 130 faces a light source 134 and the exit end 131 faces a light detector 135. With the sensor 105 positioned between the light source 134 and the photodetector 135 (for example, between the exit end 131 and the photodetector 135) to receive and transmit photons, the photodetector is enabled to sense changes in optical properties of the sensor 105. The surfaces 198 and 199 are arranged at predetermined angles so as to reflect most of the photons from the light source 134 toward the sensor 105. Moreover, the light source 134 is selected to have a light emission angle that enables the sensor system 100 to operate over a wide range of humidity and temperature conditions. Where the light source includes an LED with a photon beam emission half angle of less than about 20 degrees, or preferably as small a half angle as possible, such as about 12 degrees, the system 100 can operate between about −40 C to about +70 C. The photodetector may be a photodiode or phototransistor.

The chamber portion 106C of the housing 106 is foil led with ports 160 and 161 extending from the optics chamber 137 to support the light pipe member 116 in relation to the light source 134 and the light detector 135. In the illustrated embodiment of FIG. 2B, a port 160 receives the longer section 116L and a port 161 receives the shorter section 116S. The port 161 is immediately adjacent and leads directly into the sensor chamber 111 which is configured with slots 170 to support the sensor 105 in the predetermined orientation which may include a face view where the photon beam strikes one of the faces of the disk(s)) or an edge view where the photon beam strikes the circumferential edge. In FIGS. 2B and 2C, the slots 170 are oriented as such to support the sensor in face view relative to the photon beam. The U-shaped or trapezoidal optical path provided by the light-pipe assembly 117 advantageously allows both the light source 134 and the light detector 135 to be surface mounted on the circuit board 136 as a space-saving and convenience measure. The light pipe section 116L passes photons from the light source 134 toward the reflective surface 198 which redirects the photons along mid-light pipe section 116M toward the reflective surface 199 which redirects the photons along the light pipe section 116S. The photons exit the light pipe member 116 and strike the sensor 105. After interacting with the sensor, photons passing through the sensor are received and sensed by the light detector 135.

With reference to FIGS. 1B and 1C, positioned between the sensor 105 and the photodetector 135 is a longer window member 140 configured to seal the sensor chamber 111. The window member 140 sits in a recess 150 (FIG. 3B) formed in the base member 106B and may be welded in place. Positioned between the section 116L of the light pipe and the light source 134 is a shorter window member 141 which seals the port 161. The window member 141 sits in a recess 151 (FIG. 3A) formed in the base member 106B and may be welded in place. The O-ring 109 surrounding the section 116L of the light pipe also seals the chamber 111 to prevent leakage into the sensor chamber 111. The window members 140, 141 allow efficient transmission of light, respectively, into and out of the light pipe member 116. The recesses 150 and 151 connect with the ports 160 and 161, as best shown in FIG. 2B.

In accordance with a feature of the present invention, the sensor 105 is sensitive to a target gas and responsive to at least a threshold level or concentration of the target gas within the time require by the standard(s), including UL2034 for North American single station alarms and BSI EN 50291 for European domestic market, as shown below in detail. In the disclosed embodiment, the optical properties, including optical transparency, optical transmission, optical obscuration, and photon absorption and/or photon transmissivity, of the sensor are altered when the sensor is exposed to at least a threshold level or concentration of a target gas for a period of time, such as CO. For example, the sensor darkens or increases in opacity, thereby reducing the amount of light transmitted through the sensor and sensed by the photodetector 135. The change in the amount of light transmitted over a period of time (namely, the rate of change of sensor transmissivity I(1-2) over time t(1-2)) is proportional to the target gas or CO concentration over that period of time between readings. The sensor can be read or sampled at a predetermined rate ranging between about every few seconds to about every 30 to 45 seconds, depending on design type and objective of the application. These factors and parameters can be controlled by suitable circuitry and software executed by a microprocessor provided on the circuit board 136.

Figure 3C:
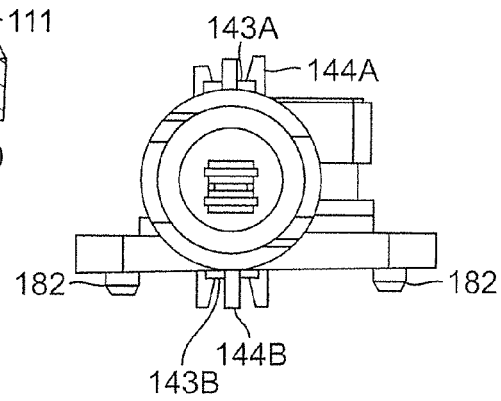
FIG. 3C is an end view of the system of FIG. 2.

In accordance with a feature of the present invention, the housing 106 of the system is sealed except for one or more through-holes or vents 143. In the illustrated embodiment of FIG. 2A, the holes 143 are formed in the receiving portion 106R. The holes permit air/gases to enter and diffuse in the housing 106 for sensing by the system 100. The holes also permit air/gases to exit the housing. The plurality of the holes can range between about one and five. Any hole 143 may also be covered by a membrane constructed of porous PTFE or PE, including TEFLON, GORETEX and UPE, to prevent water from entering the chamber, which is useful for certain applications, such as boating. In the illustrated embodiment, two through-holes 143 are formed in the tubular side wall 124 of the receiving portion 106R near a junction of the passage 110 and the cavity 121 of the receiving portion. As illustrated in FIG. 2D, the holes 143 lie along a circumference of the receiving portion, separated from each other along the circumference by a predetermined angle ranging between about 0 and 180 degrees. In the embodiment of FIG. 1B, two holes 143A and 143B are spaced apart by about 90 degrees. In the embodiment of FIG. 3C, the two holes 143A and 143B (and their respective crown formations 144A and 144B as explained below) are spaced apart by about 180 degrees.

Each hole may be configured with a crown formation 144 with a plurality of surrounding prong projections 145 for supporting and receiving a nozzle or tube (not shown) to funnel in target gas, e.g., CO, from an in-field testing spray can. The system 100 may be tested after installation and at selected time periods afterwards. In one embodiment, the system is configured to activate an alarm with two minutes or less after actuation of a "test" mode operation in the system, for example, by depression of a "test" button (not shown) or use of a magnetic read switch (now shown) after exposure to the target gas. For example, CO can be injected into a crowned hole 143 by means of a CO alarm test gas aerosol can containing test gas with a CO concentration ranging between about 1000 PPM to 2000 PPM, and preferably about 1850 PPM, which is dispensed for about 3 seconds (plus or minus one second) into a crowned hole 143.

To assemble the system 100 as shown in FIG. 1A, the sensor 105 is placed inside the controlled sensor chamber 111 that is accessed via the opening 123, the cavity 121, and treatment chamber 110 of the receiving portion 106R. The shock absorber 104 can be inserted into the controlled chamber 111 after the sensor 105 to occupy space remaining in the controlled chamber 111 so as to dampen any jarring motion that may be imparted to the sensor 105 in the event the housing 106 (or an alarm containing the system 100) is accidentally dropped. The shock absorber may be made of any material that is elastic and allows gas and vapor exchange, for example, a plastic open cell foam or felt. It is shaped and sized so that it fits generally in the controlled chamber 111 and does not extend significantly into the cavity 121. In the disclosed embodiment, the shock absorber has a rectangular configuration and is made of polyester felt.

Following the shock absorber 104, the getter 103 is placed in the treatment chamber 110. In a disclosed embodiment as shown in FIG. 1A, the getter 103 includes a porous bag that holds about 0.05-0.20 grams of porous activated carbon beads (about 0.65-0.85 mm diameters, coated with about 10-13% $H_3PO_4$ by weight). The getter when rolled up is shaped and sized to occupy most of the space in the treatment chamber 110 between the reservoir assembly 101 and the sensor chamber 111.

With further reference to FIG. 1A, the gasket 102 may be inserted into the cavity 121 after the getter 103 so that the gasket abuts the annular flange 107 at the junction of the cavity 121 and the treatment chamber 110. The reservoir assembly 101 is then inserted into the cavity 121 and axially rotated relative to the receiving portion 106R such that the locking pins 120 engage the locking grooves 119 to lock the reservoir assembly in the receiving portion 106R. The reservoir assembly 101 and the gasket 102 seal the treatment chamber 110 in the receiving portion 106R.

When the system 100 is assembled properly, the through-holes 143 are generally unobstructed by either the gasket 102 or the reservoir assembly 101. Moreover, gases entering and present inside the housing 106 can mix and interact with the moisture-controlling materials 115 in the reservoir assembly 101 such that the system and sensor can function for an extended period of time under extreme conditions, including at about 7.5% RH at about 23 C plus or minus about 3 C (a UL test) for at least about one week or at 95% RH at about 50 C plus or minus about 3 C (a UL test) for at least about one week.

The base plate 106B of the housing supporting the chamber portion 106C is fastened to the circuit board 136. In the disclosed embodiment, the base plate has edge projections or footings 180 with pins 182 and apertures 183. The pins 182 are received in recesses or holes (not shown) formed in the circuit board, and fastening screws (not shown) inserted through the circuit board are received in the apertures 183. The pins and screws hold the system 100 to the circuit board 136 as a safeguard against movement and dislodging when the system is mounted in RV, boats, marine vessels, vehicles or when accidentally dropped.

In operation, photons from the light source 134 are transmitted by the light pipe member 116 to shine on the sensor 105 whose optical property, for example, optical transparency, optical transmission, optical obscuration, photon absorption and/or photon transmissivity, changes when exposed to a target gas such as CO. As air enters the housing 106 via the through-holes 143, the air initially and immediately encounters the getter 103. The getter is situated in the treatment chamber 110 which leads directly to the controlled sensor chamber 111 so that the air is guaranteed to pass through the getter 103 before reaching the sensor 105 in the sensor chamber 111. As the air reaches the sensor 105, the sensor reacts to target gas in the air (e.g., by darkening) which results in a change in its transmission of the photons from the light source 134 as detected by the light detector 135.

Thus, the system 100 provides a defined gas path that includes entry into the housing 106 via the through-holes 143, and encounter with the getter 103 in an environment in the treatment chamber 110 where the relative humidity is maintained between about 15% and 90%, before the air reaches the sensor 105 held in the sealed controlled chamber 111.

FIG. 4 is an assembly drawing of MICROSIR MOD3-02 (M3-02) system 200, which comprises the reservoir 201, the sensor housing 206, the sensors 205, shock absorber 204, and getter systems 203 the cap 207, the lens 210, light pipe 208 and light pipe holder plate 209. Located in the interior of the sensor housing 206 are TWO sensing elements 205 for detecting wider range of CO concentrations. The gasket 202 connects and seals the reservoir assembly 201 to the sensor housing 206. The locking ears 220 are used to located and hold the reservoir 201 into the sensor housing 206 by means of a locking groove 222. This housing sits atop a surface mounted LED and Photodiode (not shown), which are mounted on a PC board. The sensor housing is located by two pins 214 and two screws located on the plate 211. Two screws to be located at two screw holes 212. The clear plate with lens 210 is welded in place and the light pipe 208 is held in place by the plate 207 (which may be welded) and the light pipe is sealed by an O-ring 209. The clear plate 210 may also be welded and mounted right above the surface mount LED (not Shown). The reservoir 201 comprises a membrane (not shown) sealed to the bottom grid (not shown), which has a number of holes and then the top 213 is welded on to the reservoir. Then the reservoir is inserted after small holes (not shown). The chemical content of salt solution and dyes are placed inside the reservoir cylinder 201 and the clear polyethylene top 215 is photon welded to the cylinder, the sensor 205 is placed in the interior chamber of 206. The reservoir is held by locking the ears 220 interfacing with the locking grooves 222. The getter system 203 is placed in the gas-path opening before the sensing element(s) 205. The getter system 203 may comprise materials that remove basic gases as well as other gases and vapors such as those of volatile organic compounds (VOCs). In addition, there is a small opening inside the getter that controls gas path (not Shown). The size of the air quality and humidity controlled chamber within the small hole defined by the small hole on one side and the reservoir on the opposite side, this chamber may also be defined by the O-ring 209 on the light pipe and the lens 210 at the bottom.

FIG. 5 is an assembly drawing of SIR-01 system 300 showing the reservoir 301 containing $MnCl_2$ chemical content (not shown), the controlled gas diffusion holes 302, acid impregnated getter felt 303 for removing ammonia/amine, sensor holder 307, ONE sensing element 308, getter+shock absorber sub-assembly 306 for additional protection against ammonia/amine and volatile organic compounds (VOCs), and retainer clip 305 for locking the sensor and the sub-assembly in place. The assembled sensor is installed inside a sensor holder 311, containing a photodiode 310 and a light emitting diode 309. Once the assembled sensor is installed, the getter felt 303 is located on top of the retainer 305; the reservoir 301 is snapped onto the sensor holder 311.

FIG. 6 is an assembly drawing of SIR-02 system 400 showing the reservoir 401 containing $MnCl_2$ chemical content (not shown), the controlled gas diffusion holes 402, an acid impregnated getter felt 403 for removing ammonia/amine, sensor holder 407, TWO sensing elements 408 for detecting wider concentrations of CO, getter+shock absorber sub-assembly 406 for additional protection against ammonia/amine and volatile organic compounds (VOCs), and retainer clip 405 for locking the sensor and the sub-assembly in place. The assembled sensor is installed inside a sensor holder 411, containing a photodiode 410 and a light emitting diode 409. Once the assembled sensor is installed, the getter felt 403 is located on top of the retainer 405; the reservoir 401 is snapped onto the sensor holder 311.

Figure 9:
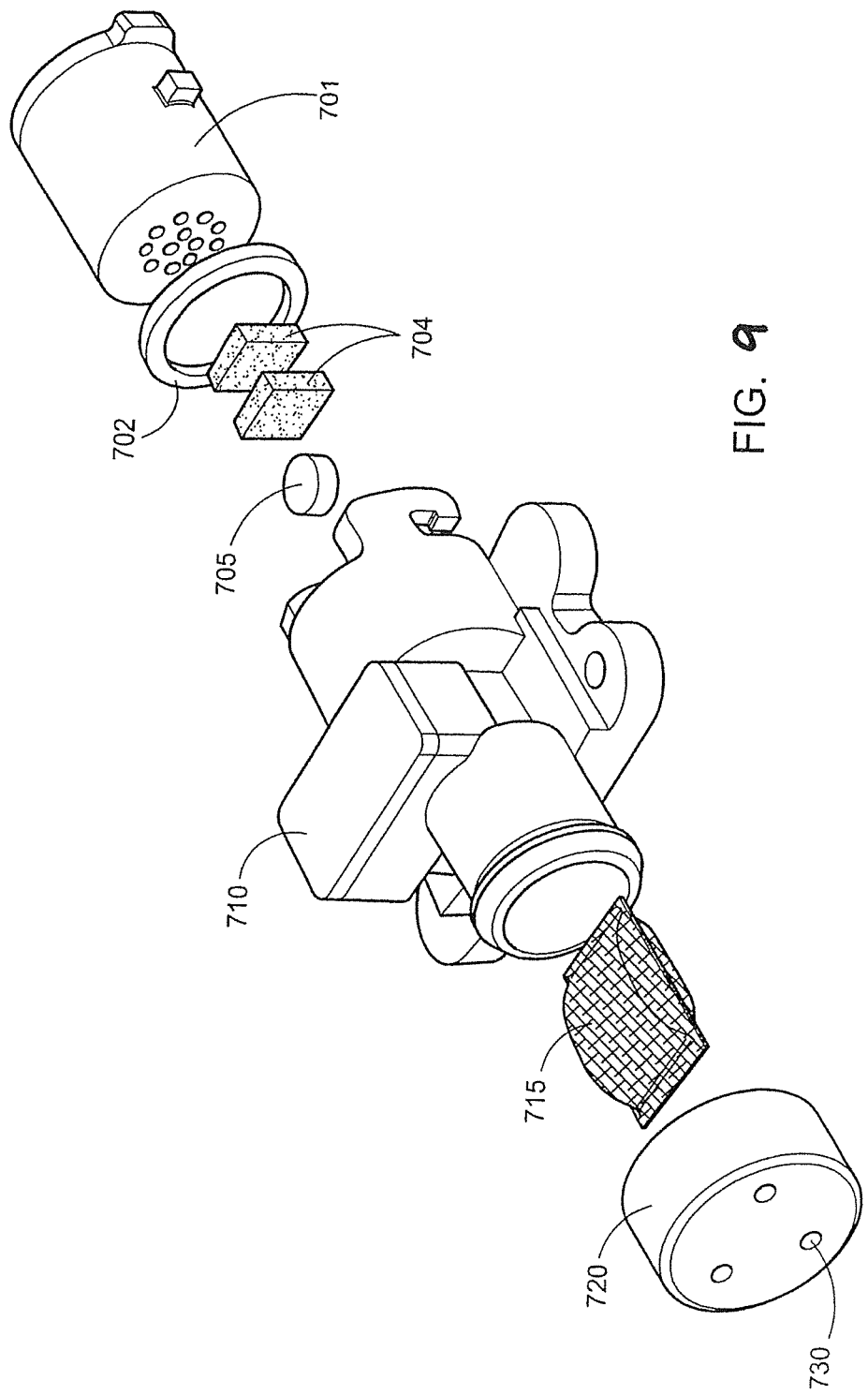
FIG. 9 is an assembly drawing of MICROSIR MOD1-01 system with only ONE, mini-sized CO sensing element located inside a controlled sensor chamber.

FIG. 7 is graphical representation of the results shown in Table 8. The result was based on a single sensing element type S66L assembled inside a MICROSIR MOD1 (M1) housing assembly as shown in FIG. 9, which is further assembled onto a PCB boards, which is operated according to a set of instructions as programmed in the software. The accuracy of the digital display of the MICROSIR CO sensing system is within ±13% in 70-ppm CO, when compared to the actual CO concentration.

FIG. 8 is graphical representation of the results shown in Table 9. The result was based on a single sensing element type S66L assembled inside a MICROSIR MOD1 (M1) housing assembly as shown in FIG. 9, which is further assembled onto a PCB boards, which is operated according to a set of instructions as programmed in the software. The accuracy of the digital display of the MICROSIR CO sensing system is within ±10% in 150-ppm CO, when compared to the actual CO concentration.

FIG. 9 is an assembly drawing of MICROSIR MOD1-01 (M1-01) system, which comprises the reservoir 701, the gasket 702, the shock absorbers 704, ONE mini CO sensing element 705, assembled housing 710, a getter systems 715, the cap 720, the diffusion controlled gas-path 730. Like the MICROSIR MOD3 (M3) (FIGS. 1A & 4), the MOD1 (M1) also contained within the assembled housing, the lens (not shown), light pipe (not shown), and light pipe holder plate (not shown). Located in the interior of the assembled housing 710 is ONE mini sensing element 705. The gasket 702 connects and seals the reservoir assembly 701 to the assembled sensor housing 710. Like the MOD3 (M3), the MOD1 (M1) also has locking ears to locate and hold the reservoir into the sensor housing by means of a locking groove. The assembled housing sits atop a surface mounted LED (not shown) and Photodiode (not shown), which are mounted on a PC board (not shown). The sensor housing is also located by two pins (not shown) and two screws (not shown) located on the plate. The clear plate with lens (not shown) is welded in place and the light pipe (not shown) is held in place by the plate (not shown) and the light pipe is sealed by an O-ring (not shown). The clear plate (not shown) may also be welded and mounted right above the surface mount LED (not Shown). The reservoir 701 comprises a membrane (not shown) sealed to the bottom grid (not shown), which has a number of holes and then the top is welded on to the reservoir. The chemical content of salt solution and dyes are placed inside the reservoir cylinder 701 and the clear polyethylene top is photon welded to the cylinder, the sensor 705 is placed in the interior chamber of assembled housing 705. The reservoir is held by locking the ears interfacing with the locking grooves. The getter system 715 is placed in the gas-path opening before the sensing element 705. The getter system 715 may comprise materials that remove basic gases as well as other gases and vapors such as those of volatile organic compounds (VOCs). In addition, there is a small opening inside the getter that controls gas path (not Shown). The size of the air quality and humidity controlled chamber within the small hole defined by the small hole on one side and the reservoir on the opposite side, this chamber may also be defined by the O-ring (not shown) on the light pipe and the lens (not shown) at the bottom.

Figure 10:
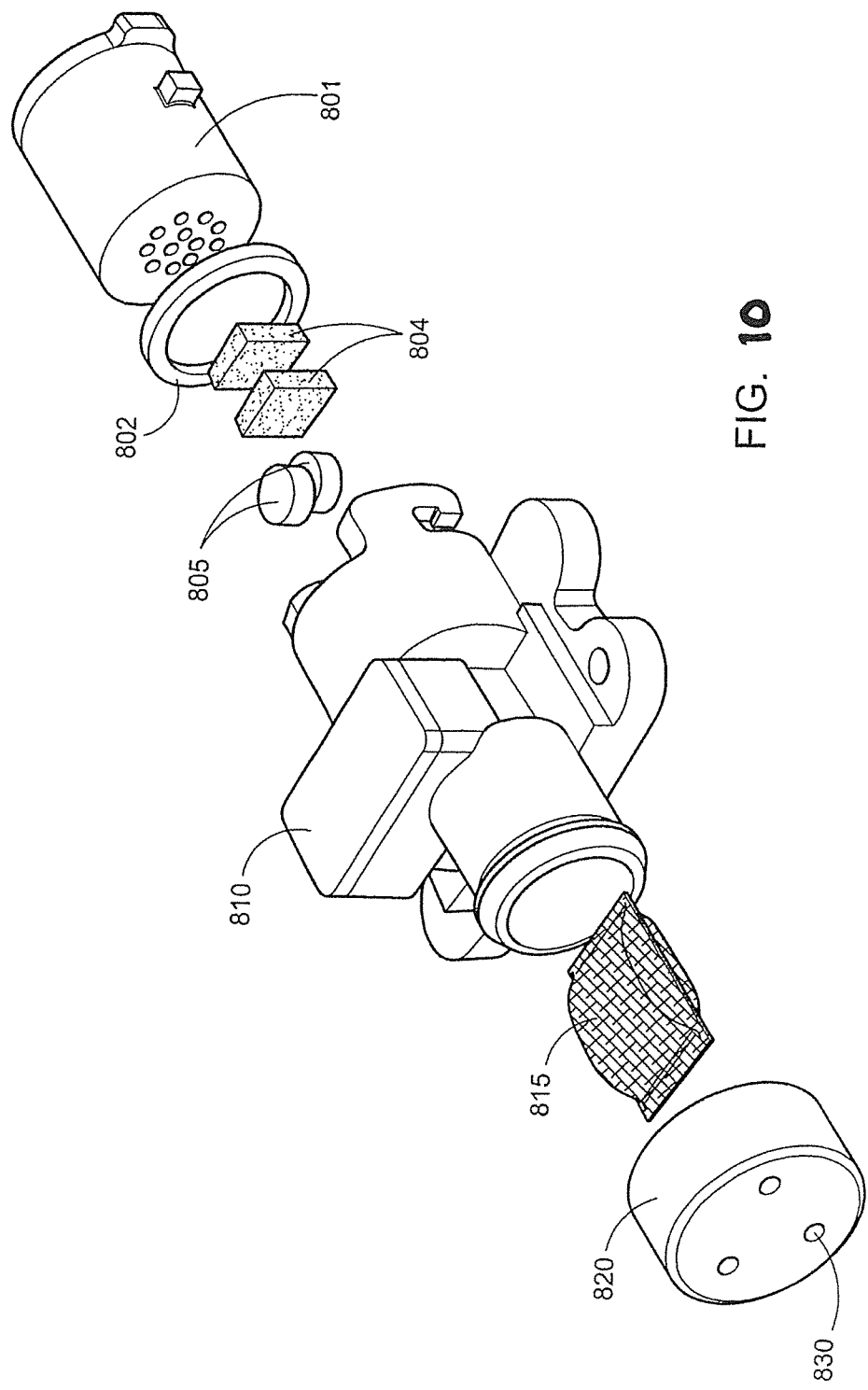
FIG. 10 is an assembly drawing of MICROSIR MOD1-02 system with TWO, mini-sized CO sensing elements located inside a controlled sensor chamber.

FIG. 10 is an assembly drawing of MICROSIR MOD1-02 (M1-02) system, which comprises the reservoir 801, the gasket 802, the shock absorbers 804, TWO mini CO sensing elements 805, assembled housing 810, a getter systems 815, the cap 820, the diffusion controlled gas-path 830. Like the MICROSIR MOD3 (FIGS. 1A & 4), the MOD1 also contained within the assembled housing, the lens (not shown), light pipe (not shown), and light pipe holder plate (not shown). Located in the interior of the assembled housing 810 are TWO mini sensing elements 805. The gasket 802 connects and seals the reservoir assembly 801 to the assembled sensor housing 810. Like the MOD3, the MOD1 also has locking ears to locate and hold the reservoir into the sensor housing by means of a locking groove. The assembled housing sits atop a surface mounted LED (not shown) and Photodiode (not shown), which are mounted on a PC board (not shown). The sensor housing is also located by two pins (not shown) and two screws (not shown) located on the plate. The clear plate with lens (not shown) is welded in place and the light pipe (not shown) is held in place by the plate (not shown) and the light pipe is sealed by an O-ring (not shown). The clear plate (not shown) may also be welded and mounted right above the surface mount LED (not Shown). The reservoir 801 comprises a membrane (not shown) sealed to the bottom grid (not shown), which has a number of holes and then the top is welded on to the reservoir. The chemical content of salt solution and dyes are placed inside the reservoir cylinder 801 and the clear polyethylene top is photon welded to the cylinder, the sensor 805 is placed in the interior chamber of assembled housing 805. The reservoir is held by locking the ears interfacing with the locking grooves. The getter system 815 is placed in the gas-path opening before the sensing element 805. The getter system 815 may comprise materials that remove basic gases as well as other gases and vapors such as those of volatile organic compounds (VOCs). In addition, there is a small opening inside the getter that controls gas path (not Shown). The size of the air quality and humidity controlled chamber within the small hole defined by the small hole on one side and the reservoir on the opposite side, this chamber may also be defined by the O-ring (not shown) on the light pipe and the lens (not shown) at the bottom.

Figure 11:
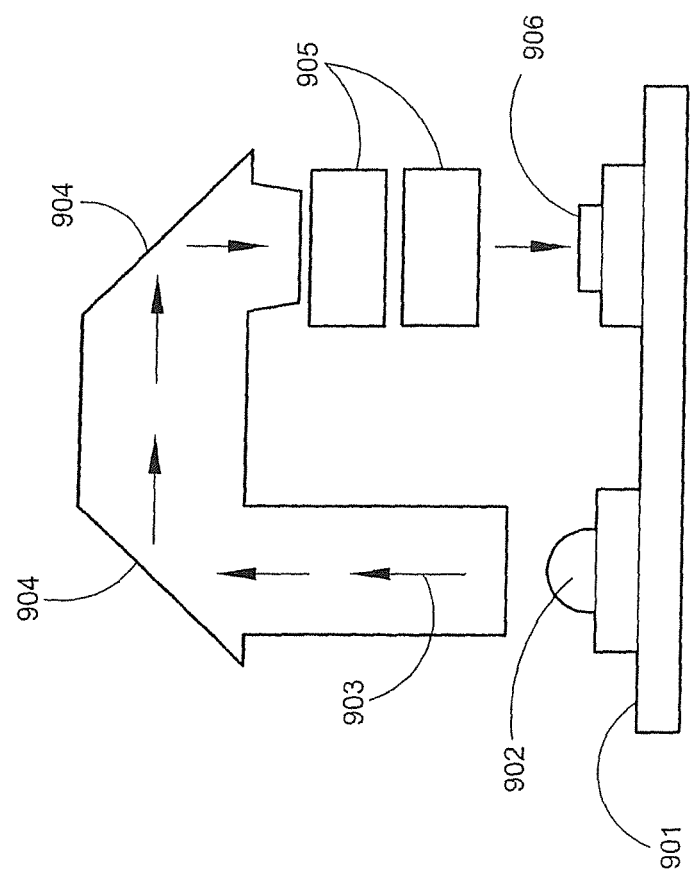
FIG. 11 is a side-view illustration of the theory of operation for the MICROSIR CO sensing system.

FIG. 11 is a side-view illustration of the photon path showing the theory of operation for the MICROSIR CO sensing system. Shown in the illustration is the PC board 901, the IRLED 902, the light pipe 903 and its defective turns 904, the sensing elements (ONE or TWO, shown are TWO), and the photo detector 905. The response characteristic (output) of the MICROSIR CO Sensor 905 is the measure of light obscuration 903 through the semi-transparent MICROSIR CO Sensing element(s) 905. Like Quantum's current, large-sized SIR CO sensors, the new MICROSIR CO sensors are also highly selective to CO. When the sensing element(s) 905 encounters CO (not shown), it darkens (not shown). When CO is removed, the sensor returns to its original state (recovery, not shown). The darkening rate of the sensor is proportional to CO gas concentration in the air surrounding the sensor. To monitor the sensing element's rate of darkening (sensor+CO reaction) and/or lightening (recovery), a light source such as an Infrared Light Emitting Diode (IRLED) 902 pulses or emits photons 903 every 30 to 45 seconds. The emitting photons 903 journey are guided by the light pipe and its turns 904 to the sensing element(s) 905. The existing protons are then detected by a photodiode 906. The higher the CO concentration reacting with the sensor, the darker the sensing element(s), the fewer the number of photons (amount of light) detected by the photodiode.

FIG. 12 is a graphical representation showing the response characteristics of ONE mini-sized S66e sensor series, in a MICROSIR MOD1-01 to, 70 ppm 1002, 150 ppm 1003, and 400 ppm CO 1004 at 23±3° C. and 55±5% RH, as specified in criteria 1. Sensing elements were singly installed in the MICROSIR MOD1-01 assembly configuration (FIG. 9) then mounted on the 8UP-MICROSIR-voltage output board, so the sensor output is converted to a voltage level corresponding to the obscuration of light passing through the MICROSIR CO sensing element. The signal conditioning is performed by a test circuit containing an operational amplifier (OpAmp). The amplification circuit is set to attain an initial value of 4 Volts output. As the sensor responds to CO, the voltage output decreases. This voltage-output board is a subject of a U.S. Patent application No. 60/711,748, filed on Aug. 25, 2005, and U.S. patent application Ser. No. 11/509,875, now abandoned. The complete assembled samples were then stored inside a Thermotron environmental chamber, which maintained at 23° C./55% RH. CO was injected into the chamber to create and maintain 30±3 ppm for 8 hours, 70±3 ppm for 4 hours, 150±5 ppm for 50 minutes, and 400±10 ppm for 15 minutes. At the end of each CO gas test, air injection was necessary to purge out the CO and to regenerate the sensing element for the next CO gas test. The responses are expressed as change in the voltage output (volt) versus time. The responses are as expected. That is, the high the CO concentration the bigger the responses. Following this test, the system is subjected "sequentially" to selected tests at extreme conditions as described in FIGS. 13 through 16 to verity the system performance to the UL 2034 standards for both the RESIDENTIAL and RECREATIONAL VEHICLE requirement.

Figure 13A:
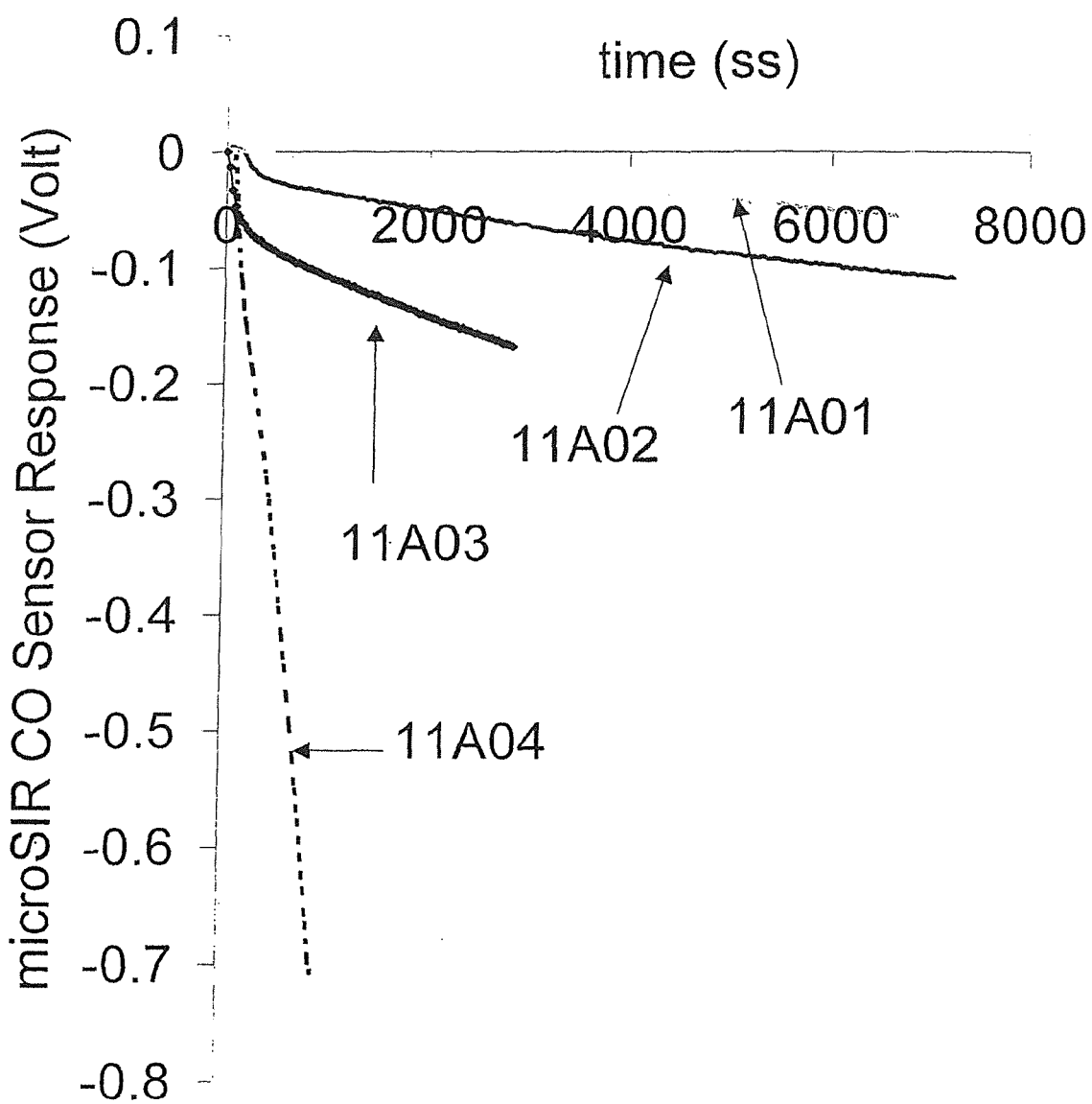
FIG. 13A is graphical representation showing response characteristics of the same MICROSIR CO sensor system from FIG. 12 to 30 ppm 11A01, 70 ppm 11A02, 150 ppm 11A03, and 400 ppm CO 11A04 at 49° C. and 40% RH, as specified in criteria 6.

FIG. 13A is a graphical representation showing the response characteristics of the same MICROSIR CO sensor system from FIG. 12 to 30 ppm 11A01, 70 ppm 11A02, 150 ppm 11A03, and 400 ppm CO 11A04 at 49° C. and 40% RH, as specified in criteria 6. The system was preconditioned at 49° C./40% RH for 3 hours prior to the CO exposures at the same conditions. There is a clear differentiation among the responses to four different CO concentrations ranging from 30 to 400 ppm. Following the 49° C./40% RH test, the system was subjected to a 66° C./40% RH as described in FIG. 13B.

Figure 13B:
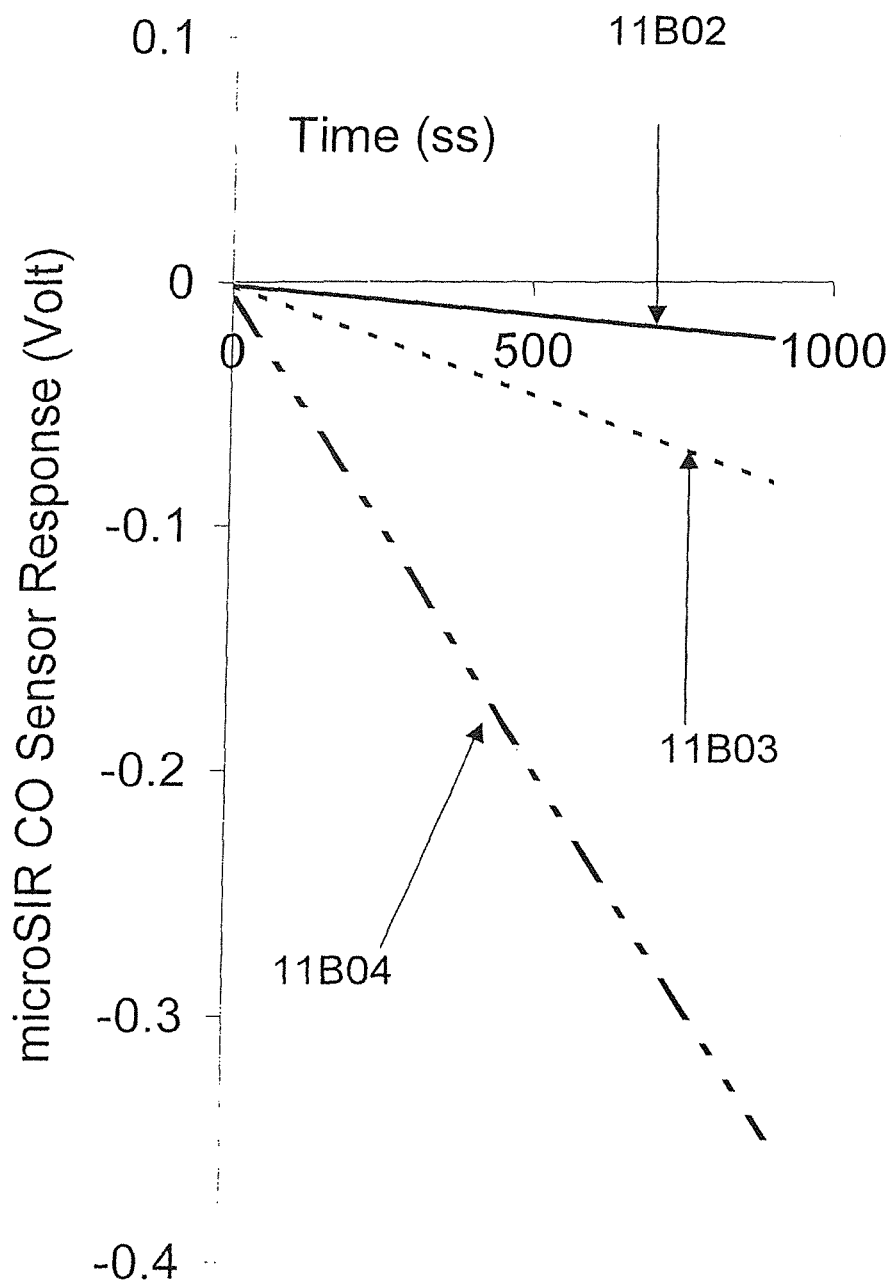

FIG. 13B is a graphical representation showing the response characteristics of the same MICROSIR CO sensor system from FIG. 13A to 70 ppm 11B02, 150 ppm 11B03, and 400 ppm CO 11B04 at 66° C. and 40% RH, as specified in UL 2034 Section 69.1a. The system was preconditioned at 66° C. and 40% relative humidity for 30 days prior to the CO exposures at the same conditions. There is a clear differentiation among the responses to three different CO concentrations ranging from 70 to 400 ppm. The response to 30 ppm (not shown) was not measured but is expected to have the least voltage change. Following the 66° C./40% RH test, the system was subjected to 0° C./15% RH as described in FIG. 14A.

Figure 14A:
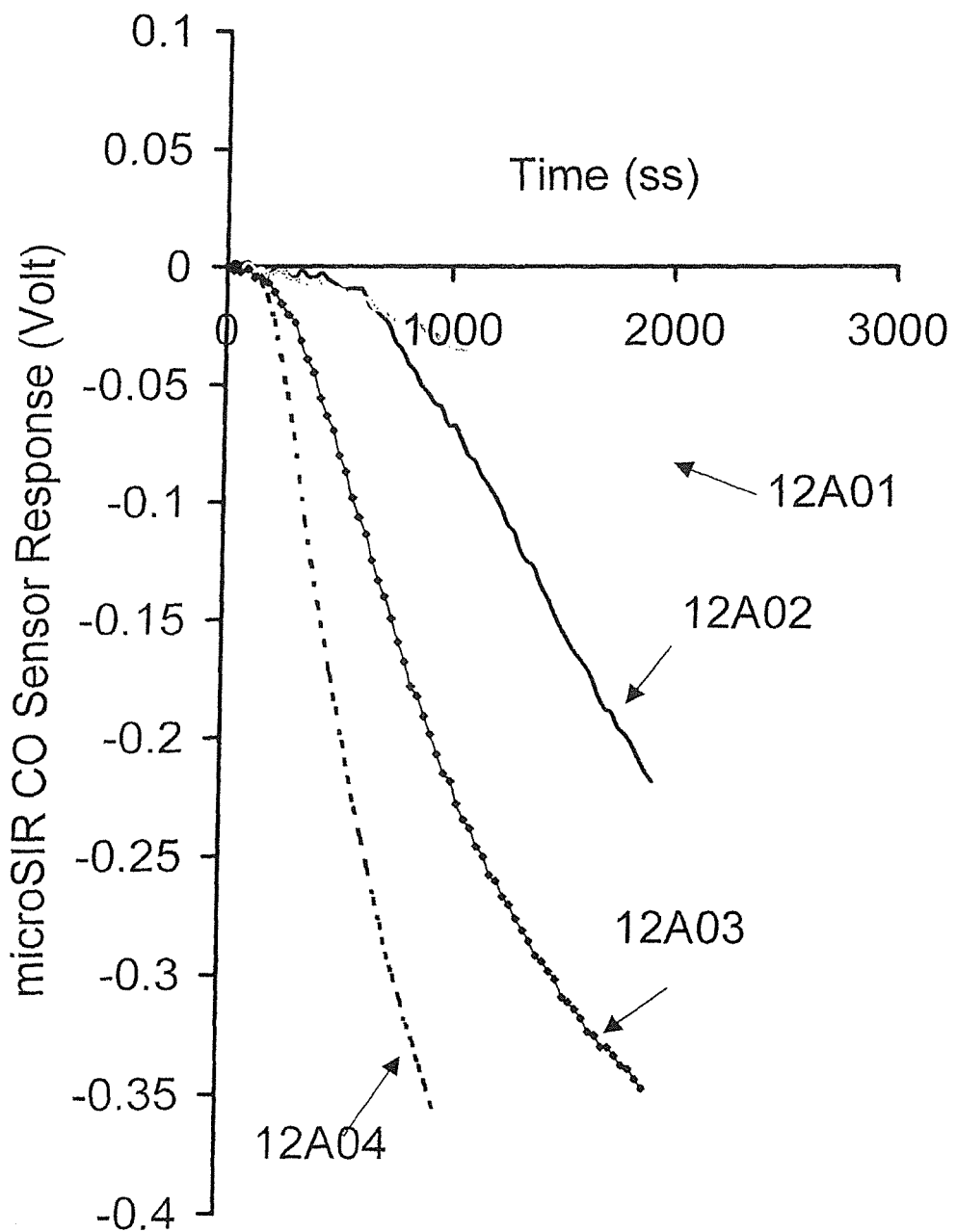
FIG. 14A is graphical representation showing response characteristics of the same MICROSIR CO sensor system from FIG. 13B to 30 ppm 12A01, 70 ppm 12A02, 150 ppm 12A03, and 400 ppm CO 12A04 at 0° C. and 15% RH, as specified in Criterion 7 or UL 2034 Section 45.1.

FIG. 14A is a graphical representation showing the response characteristics of the same MICROSIR CO sensor system from FIG. 13B to 30 ppm 12A01, 70 ppm 12A02, 150 ppm 12A03, and 400 ppm CO 12A04 at 0° C.° C. and 15% RH, as specified in Criterion 7 or UL 2034 Section 45. The system was preconditioned or stored at 0° C./15% RH for 3 hours prior to the CO exposures at the same conditions. There is a clear differentiation among the responses to all four different CO concentrations ranging from 30 to 400 ppm. Following the 0° C./15% RH test, the system was subjected to a minus (−) 40 C test as described in FIG. 14B.

Figure 14B:
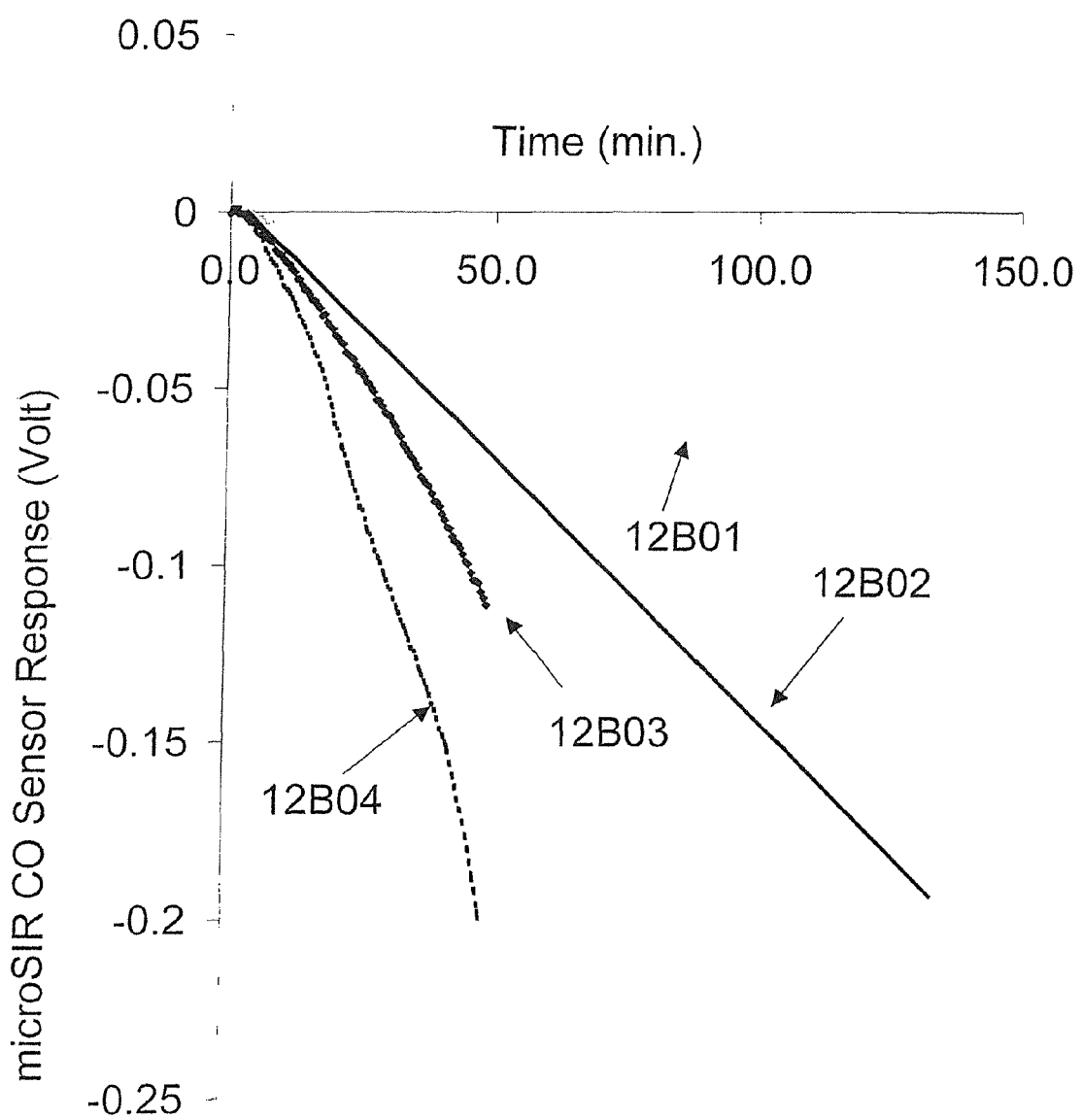
FIG. 14B is graphical representation showing response characteristics of the same MICROSIR CO sensor system from FIG. 14A to 30 ppm 12B01, 70 ppm 12B02, 150 ppm 12B03, and 400 ppm CO 12B04 at minus (−) 40° C., as specified in UL 2034 Section 69.1b. Clearly the slopes of these curves are different and therefore they may be distinguished by the software.

FIG. 14B is a graphical representation showing the response characteristics of the same MICROSIR CO sensor system from FIG. 14A to 30 ppm 12B01, 70 ppm 12B02, 150 ppm 12B03, and 400 ppm CO 12B04 at minus (−) 40 C.°, as specified in UL 2034 Section 69.1b. The system was preconditioned or stored at minus (−) 40° C. for 3 days prior to the CO exposures at the same conditions. There is a clear differentiation among the responses to four different CO concentrations ranging from 30 to 400 ppm. Following the minus (−) 40° C. test, the system was subjected to a minus 61° C./93% RH as described in FIG. 15.

Figure 15:
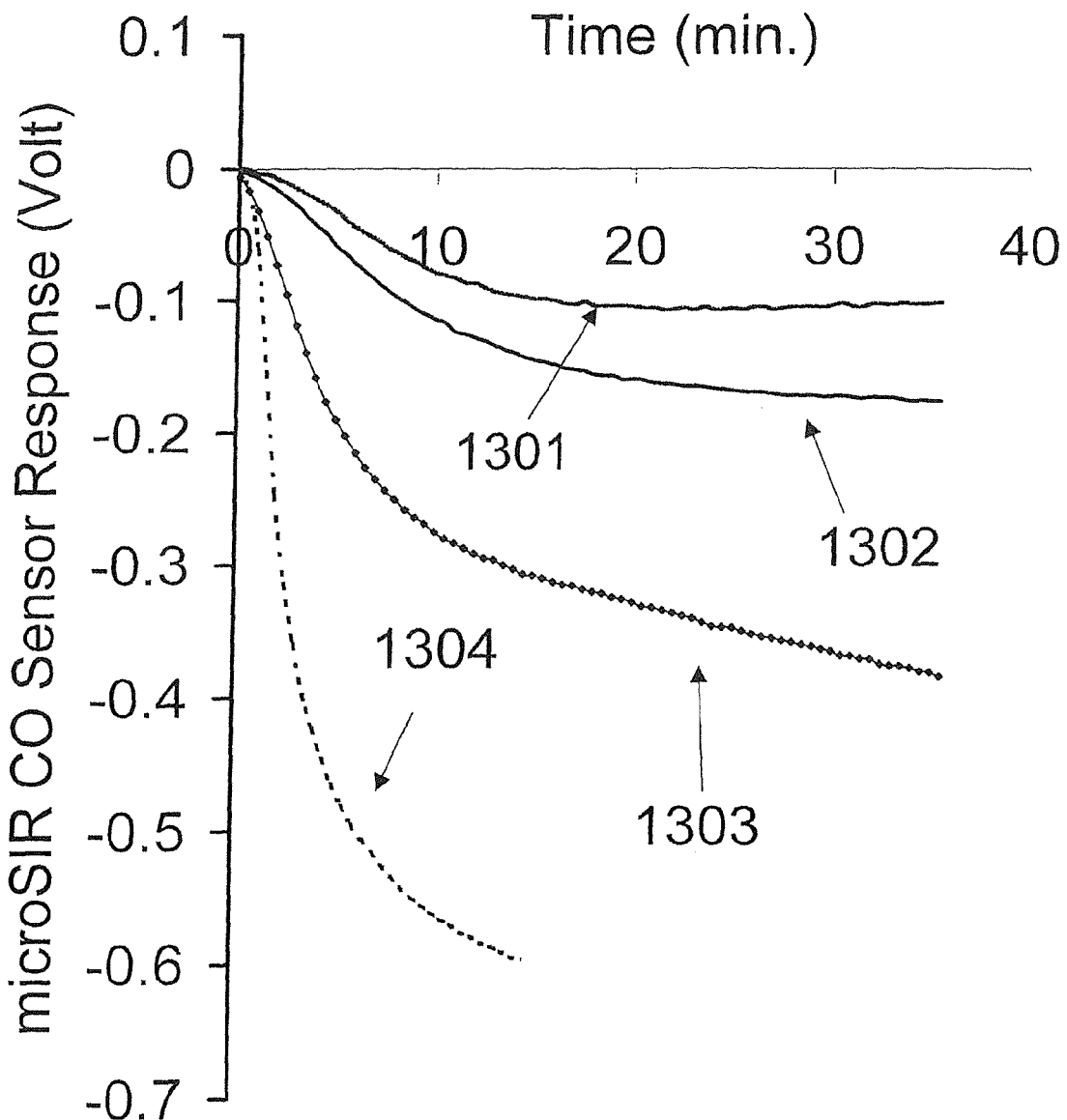
FIG. 15 is graphical representation showing response characteristics of the same MICROSIR CO sensor system from FIG. 14B to 30 ppm 1301, 70 ppm 1302, 150 ppm 1303, and 400 ppm CO 1304 at 61° C. and 93% RH, as specified in UL 2034 Section 69.1c.

FIG. 15 is a graphical representation showing the response characteristics of the same MICROSIR CO sensor system from FIG. 14B to 30 ppm 1301, 70 ppm, 150 ppm 1303, and 400 ppm CO 1304 at minus 61° C. and 93% RH, as specified in UL 2034 Section 69.1c. The system was preconditioned or stored at 61° C./93% RH for 10 days prior to the CO exposures at the same conditions. There is a clear differentiation among the responses to four different CO concentrations ranging from 30 to 400 ppm. Following the 61° C./93% RH test, the system was subjected to a minus 23° C./10% RH as described in FIG. 16.

Figure 16:
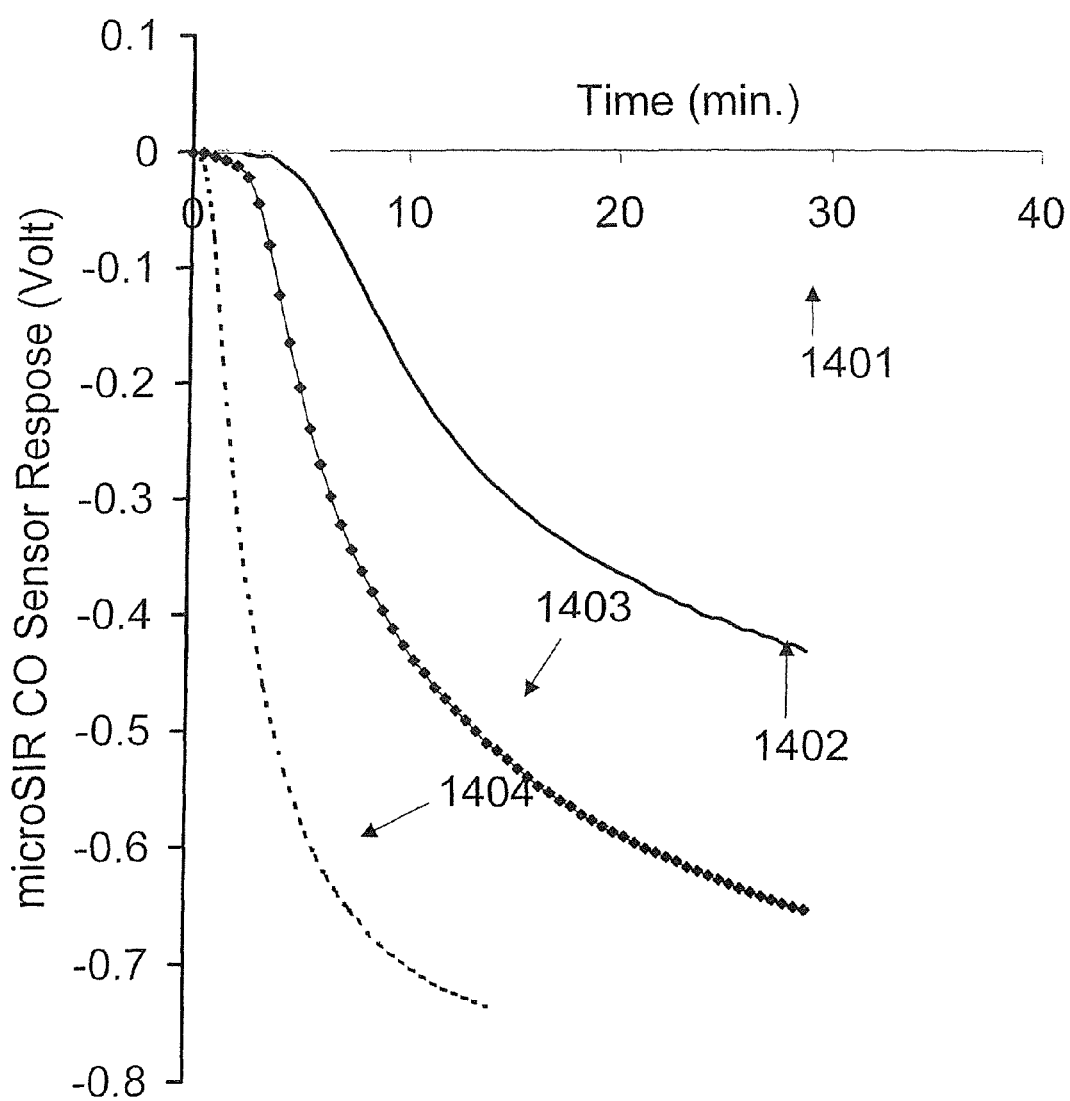
FIG. 16 is graphical representation showing response characteristics of the same MICROSIR CO sensor system from FIG. 15 to 30 ppm 1401, 70 ppm 1402, 150 ppm 1403, and 400 ppm CO 1404 at minus 23° C. and 10% RH, as specified in UL 2034 Section 46A.2.

FIG. 16 is a graphical representation showing the response characteristics of the same MICROSIR CO sensor system from FIG. 15 to 30 ppm, 70 ppm 1402, 150 ppm 1403, and 400 ppm CO 1404 at 23° C. and 10% RH, as specified in UL 2034 Section 46A.2. The system was preconditioned or stored at 23° C./10% RH for 7 days prior to the CO exposures at the same conditions. Again, there is a clear differentiation among the responses to four different CO concentrations ranging from 30 to 400 ppm. This test concluded the required "Sequential" CO performance required as specified in UL 2034, Section 41.3 for both the "conditioned and unconditioned areas" applications. FIGS. 12 through 16 clearly show that the ONE mini-sized CO sensor in the MICROSIR CO sensing system can meet all performance criteria necessary for obtaining the UL 2034 approval for both the Residential (conditioned) and Recreational Vehicle (unconditioned) approval.

Figure 17A:
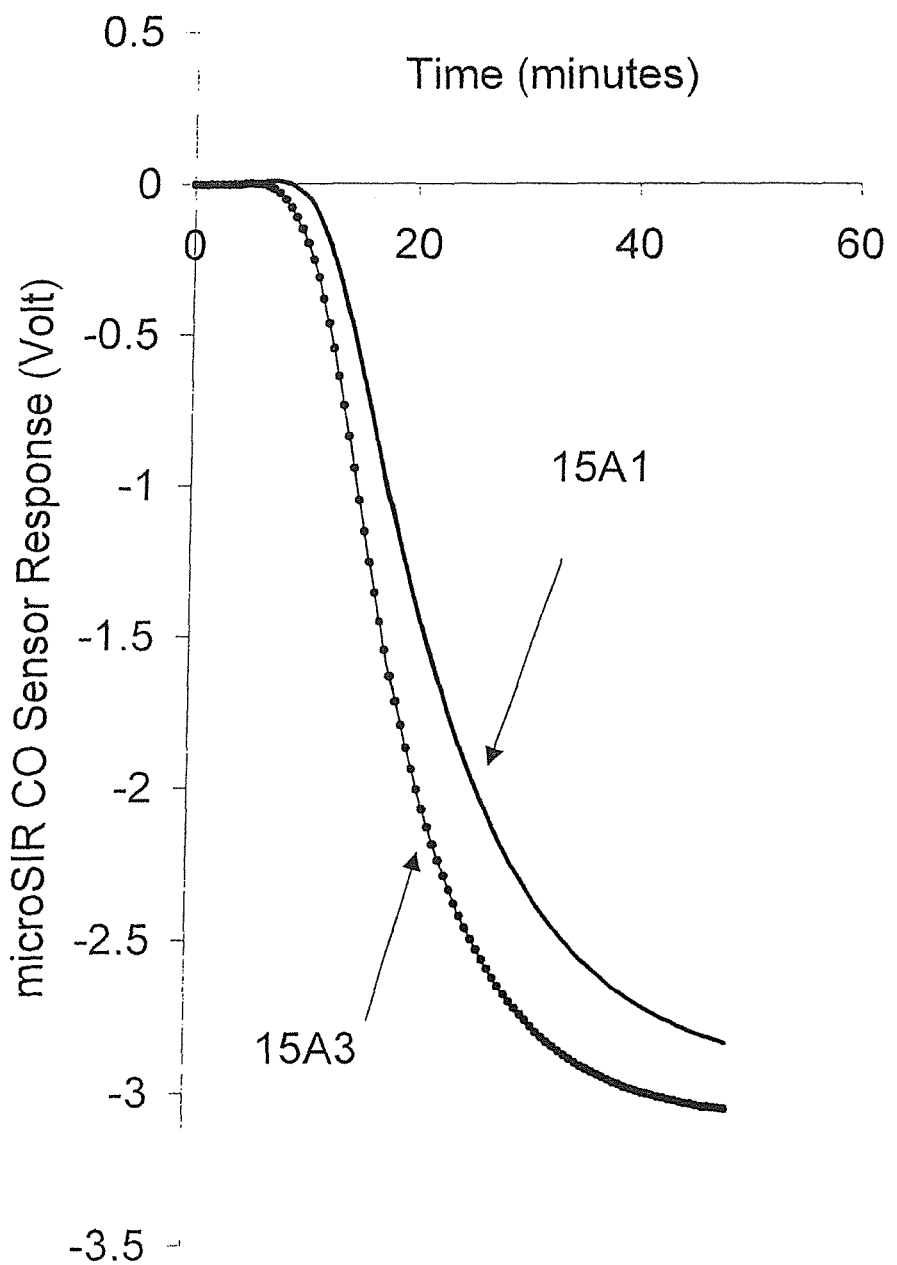
FIG. 17A is graphical representation showing comparative response characteristics of ONE mini-sized CO sensor from the S66e sensor series to 150 ppm CO in a MICROSIR MOD1-01 15A1 versus in a MICROSIR MOD3-01 15A3 at 23±3° C. and 55±5% RH.

FIG. 17A is a graphical representation showing the comparative response characteristics of ONE mini-sized S66 sensor series to 150 ppm CO in a MICROSIR MOD1-01 15A1 versus in a MICROSIR MOD3-01 15A3 at 23±3° C. and 55±5% RH. The dash 01 following a MOD identifies that there is ONLY ONE sensing element. Like those samples in FIGS. 12 to 16, these assembled samples were also mounted on the same type of 8UP-MICROSIR-voltage output board for this test. CO injection and air purge were done in the same manners as described in FIG. 12. The results were also analyzed and presented in the same manner. FIG. 17A indicates that given the same identical sensor formulation in the same CO test, the magnitude of response is greater when that sensor formulation is installed in the MOD3 15A3 than when it is installed in the MOD1 15A1.

Figure 17B:
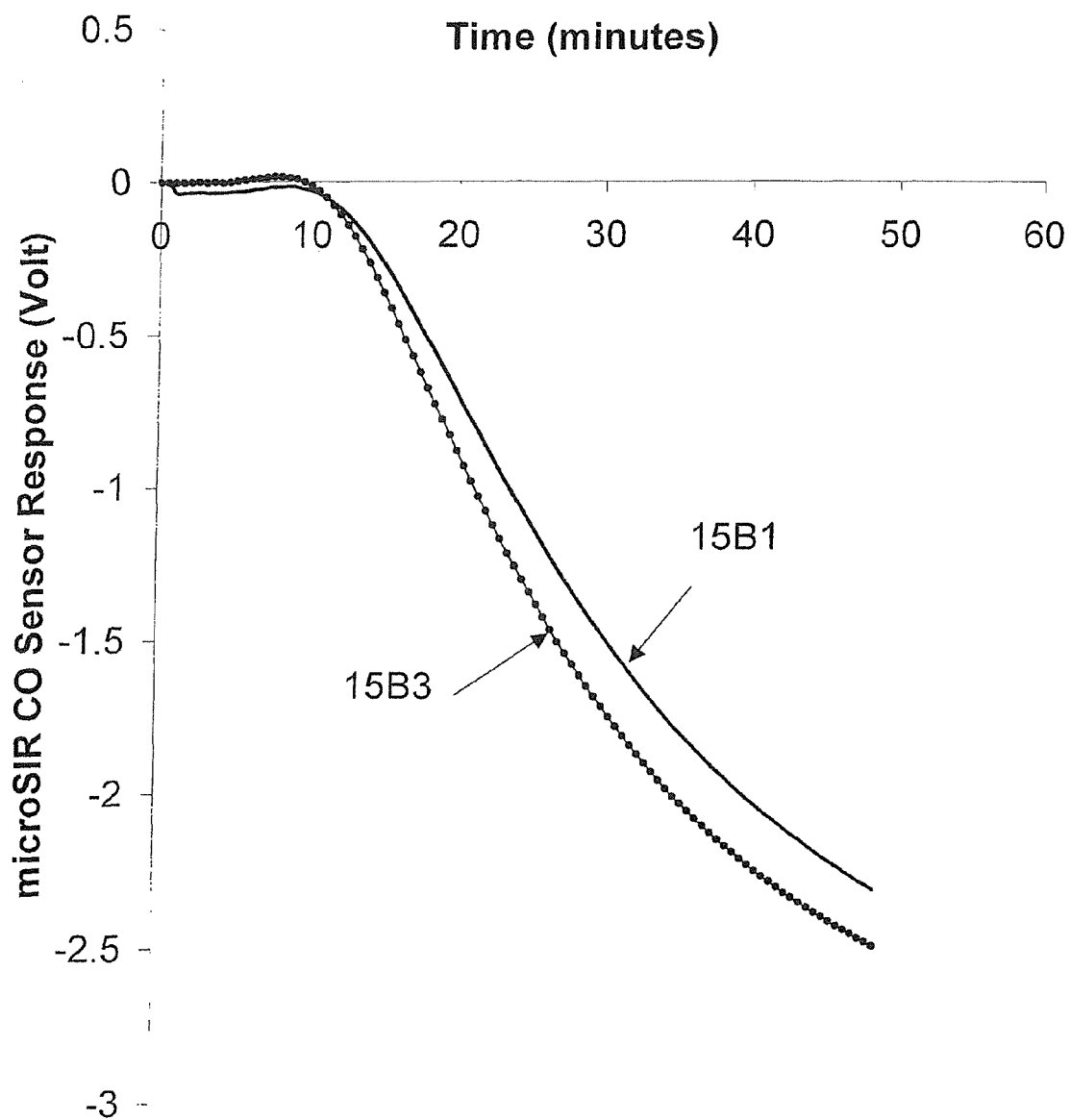
FIG. 17B is graphical representation showing comparative response characteristics of TWO mini-sized CO sensing elements from the S34 sensor series to 150 ppm CO in a MICROSIR MOD1-02 15B1 versus in a MICROSIR MOD3-02 15A3 at 23±3° C. and 55±5% RH.

FIG. 17B is a graphical representation showing the comparative response characteristics of TWO mini-sized S34 sensor series to 150 ppm CO in a MICROSIR MOD1-02 15B1 versus in a MICROSIR MOD3-02 15A3 at 23±3° C. and 55±5% RH. The dash 02 following a MOD identifies that there are TWO sensing elements. Like those samples in FIGS. 12 to 16, these assembled samples were also mounted on the same type of 8UP-MICROSIR-voltage output board for this test. CO injection and air purge were done in the same manners as described in FIG. 12. The results were also analyzed and presented in the same manner. FIG. 17B indicates that given the same identical sensor formulation in the same CO test, the magnitude of response is greater when that sensor formulation is installed in the MOD3 15B3 than when it is installed in the MOD1 15B1. FIG. 17B is in agreement with FIG. 17A.

Figure 18:
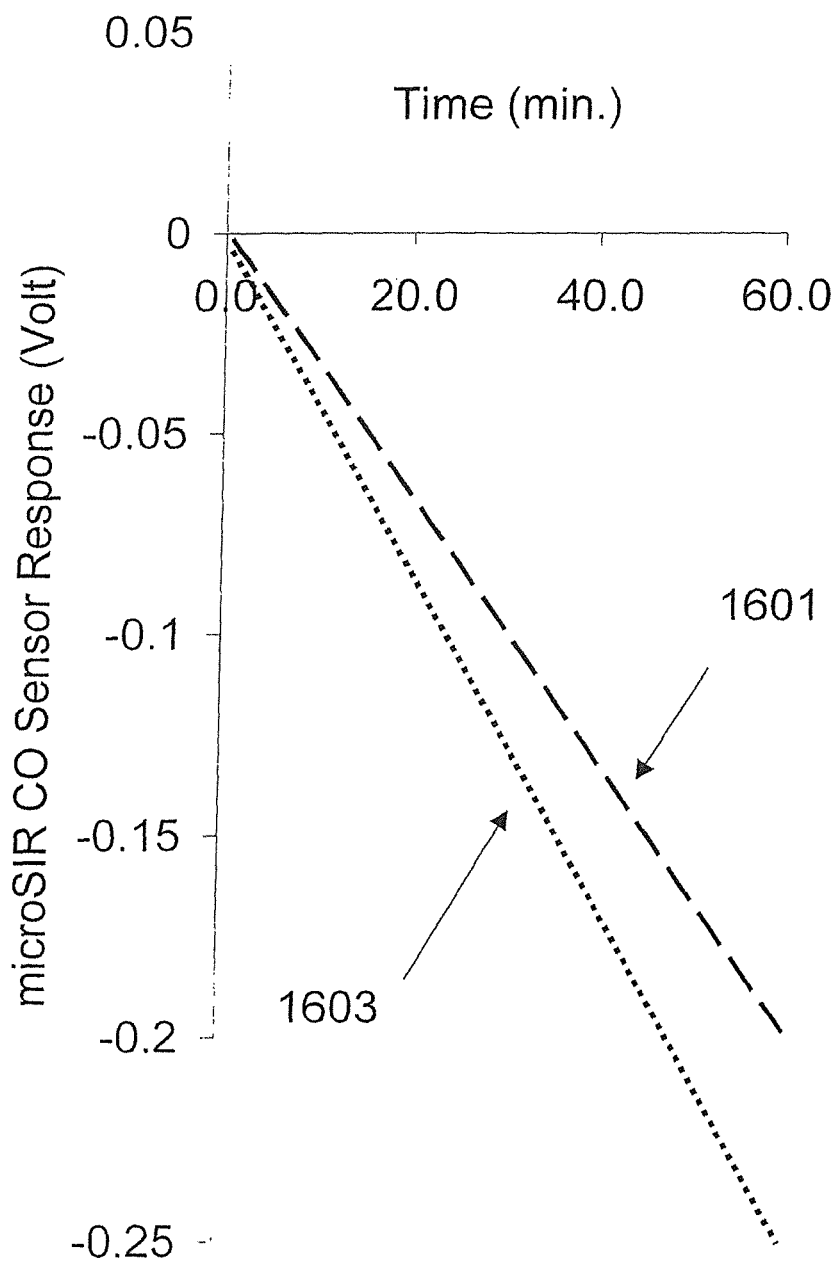
FIG. 18 is graphical representation showing comparative response characteristics of ONE mini-sized CO sensor from the S66e sensor series to 150 ppm CO in a MICROSIR MOD1-01 1601 versus in a MICROSIR MOD3-01 1603 at 66° C. and 40% RH.

FIG. 18 is a graphical representation showing the comparative response characteristics of ONE mini-sized S66 sensor series to 150 ppm CO in a MICROSIR MOD1-01 1601 versus in a MICROSIR MOD3-01 1603 at 66° C./40% RH following a 30 days of preconditioning at 66° C./40% RH. Like those samples in FIGS. 12 to 16, these assembled samples were also mounted on the same type of 8UP-MICROSIR-voltage output board for this test. CO injection and air purge were done in the same manners as described in FIG. 12. The results were also analyzed and presented in the same manner. FIG. 18 indicates that given the same identical sensor formulation in the same CO test, the magnitude of response is greater when that sensor formulation is installed in the MOD3 1603 than when it is installed in the MOD1 1601. FIG. 18 is in agreement with FIGS. 17A and 17B

Figure 19:
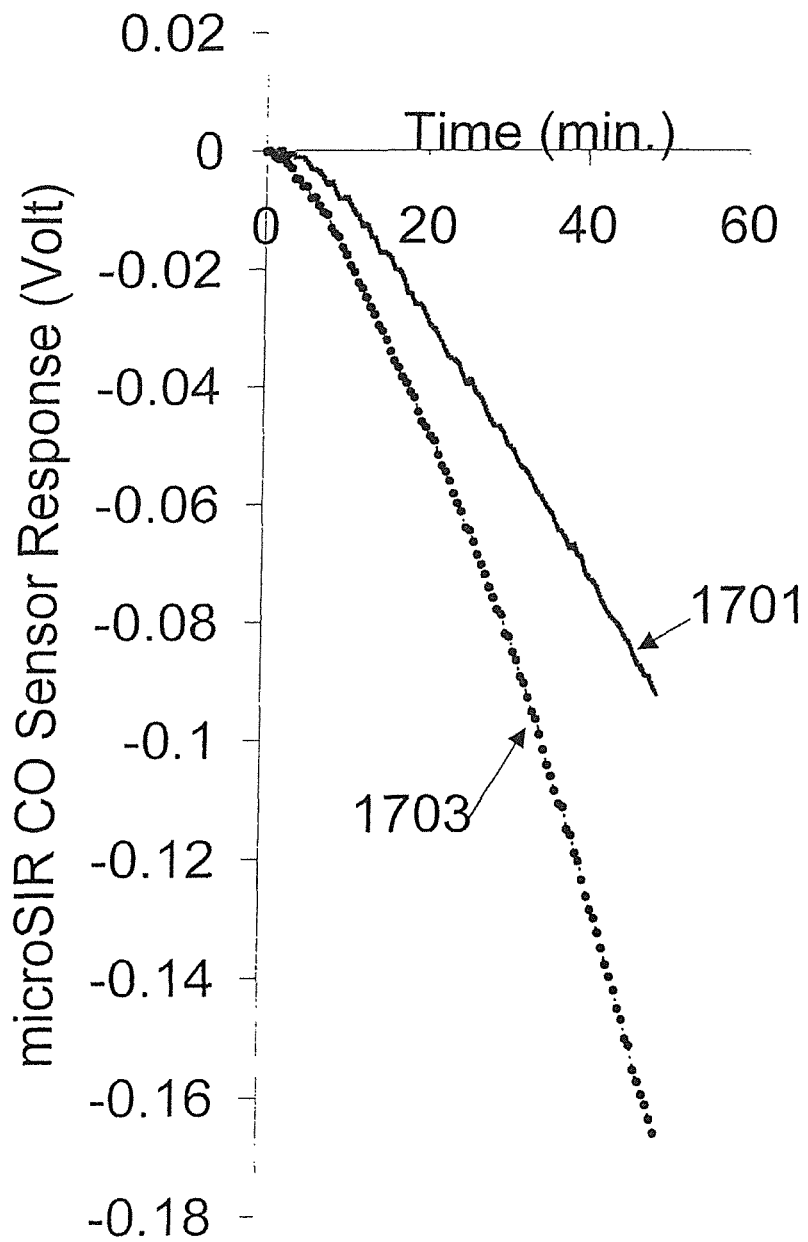
FIG. 19 is graphical representation showing comparative response characteristics of ONE mini-sized CO sensor from the S66e sensor series to 150 ppm CO in a MICROSIR MOD1-01 1701 versus in a MICROSIR MOD3-01 1703 at minus (−) 40° C.

FIG. 19 is a graphical representation showing the comparative response characteristics of ONE mini-sized CO sensor from the S66 sensor series to 150 ppm CO in a MICROSIR MOD1-01 1701 versus in a MICROSIR MOD3-01 1703 at minus (−) 40° C. following a 3 days of preconditioning at (−) 40° C. Like those samples in FIGS. 12 to 16, these assembled samples were also mounted on the same type of 8UP-MICROSIR-voltage output board for this test. CO injection and air purge were done in the same manners as described in FIG. 12. The results were also analyzed and presented in the same manner. FIG. 18 indicates that given the same identical sensor formulation in the same CO test, the magnitude of response is greater when that sensor formulation is installed in the MOD3 1703 than when it is installed in the MOD1 1701. FIG. 19 is in agreement with FIGS. 17A and 17B and 18. That is according to FIGS. 17 through 19, the same identical sensor formulation is always faster in responding to same CO concentration within the same test, from −40° C. to +66° C., when it is installed in a MOD3 than when it is installed in a MOD1. These figures also show that both MOD1 and MOD3 are capable of meeting the UL 2034 requirement for both residential and recreational vehicle approval.

Figure 20:
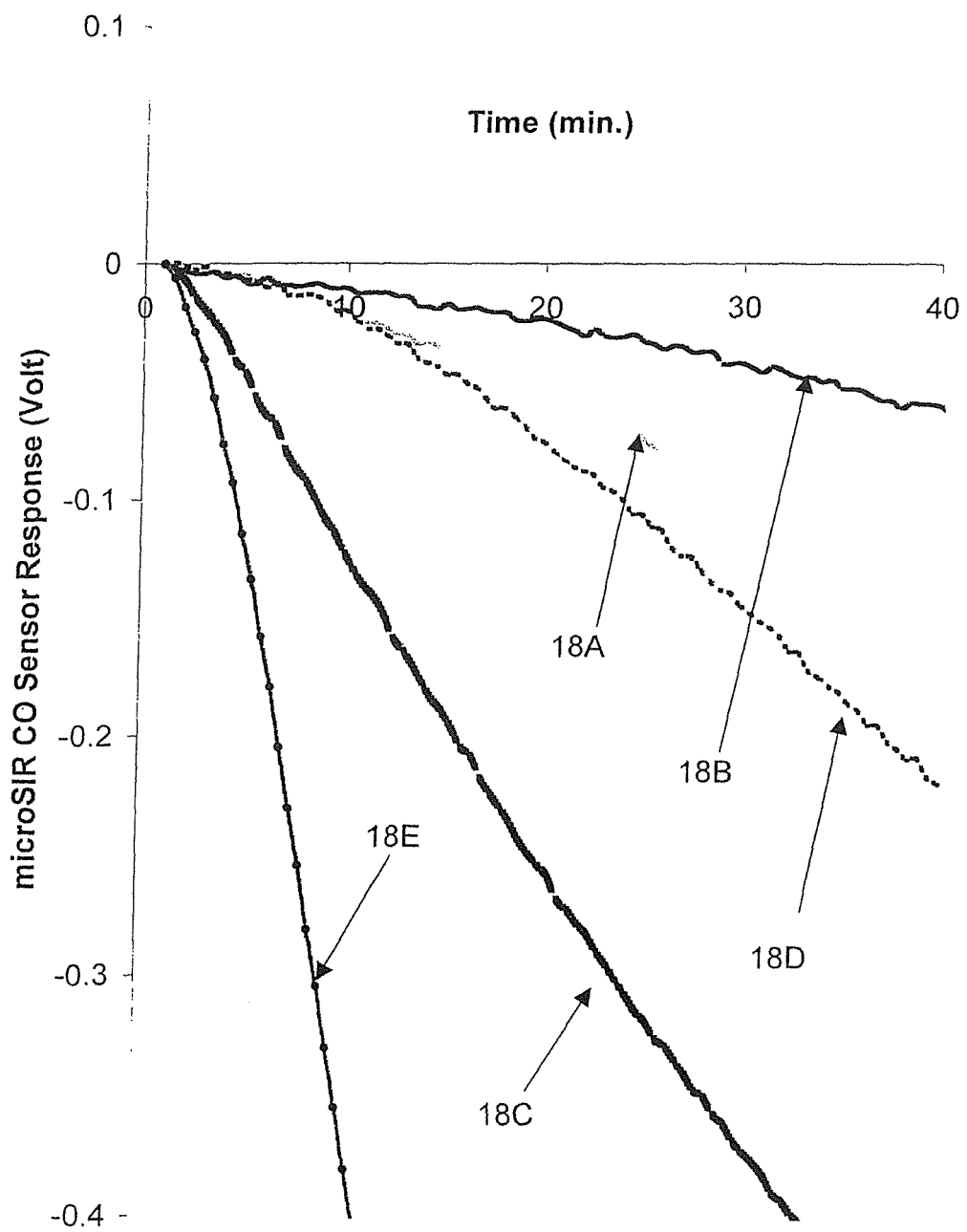
FIG. 20 is graphical representation showing IMPROVED response characteristics of the ONE mini-sized S6e formulation with $CaCl_2 + ZnCl_2/ZnBr_2$ additives to 150 ppm CO in a MICROSIR MOD1-01 1801 at 66° C. and 40% RH following 30 days of preconditioning at same conditions of 66° C. and 40% RH. This test indicates that zinc chloride and zinc bromide increase the thermal life of the sensor. In order to increase sensor life, both major failure mechanisms must be addressed. The two major failure mechanisms are basic gases and thermal stability. The thermal stability can be measured using Arrhenius type aging but Quantum has another form of accelerated aging test as well. Quantum's accelerated aging test relies on the regeneration rate or the loss in regeneration rate after heating, which is a more sensitive parameter and is easier to measure and conduct than the Arrhenius tests.

FIG. 20 is a graphical representation showing the IMPROVED response characteristics of the ONE mini-sized S6 sensor formulations with $CaCl_2$ partially to completely replaced by various proportions of $ZnCl_2$ and $ZnBr_2$ as follows: 100% $CaCl_2$ 18A (control), 100% $ZnCl_2$ 18B, 50% $ZnCl_2$+50% $ZnBr_2$ 18C, 50% $CaCl_2$+50% $ZnCl_2$ 18D, and 50% $CaCl_2$+50% $ZnBr_2$ 18E. The samples were singly installed in a MICROSIR MOD1-01. Like those samples in FIGS. 12 to 16, these assembled samples were also mounted on the same type of 8UP-MICROSIR-voltage output board for this test. The samples were preconditioned at 66° C./40% RH for 30 days. At the end of the 30$^{th}$ day, CO injection to create and maintain 150±5 ppm for 50 minutes while at the 66° C./40% RH before air was introduced to purge CO out. The results were also analyzed and presented in the same manner as described in FIG. 12. FIG. 20 shows that when $CaCl_2$ is replaced 100% by $ZnCl_2$ 18B, the response is actually lesser than the control with 100% $CaCl_2$ 18A. The proportion with 50% $CaCl_2$ and 50% $ZnBr_2$ 18E is the most sensitive one among all 5. Following this test, the sampled was tested at −40 C (not shown), but due to significant electronic noise, no valid results were obtained. Following the −40 C test, the samples were subjected to a 61° C./93% RH (not shown), where corrosion on some test sites prohibited the measurement of most sensor formulations, except those of the control (100% $ZnCl_2$) and the 50% $ZnCl_2$+50% $ZnBr_2$ formulation. That result showed that the 50% $ZnCl_2$+50% $ZnBr_2$ formulation is six times more sensitive than the control (not shown).

Figure 21:
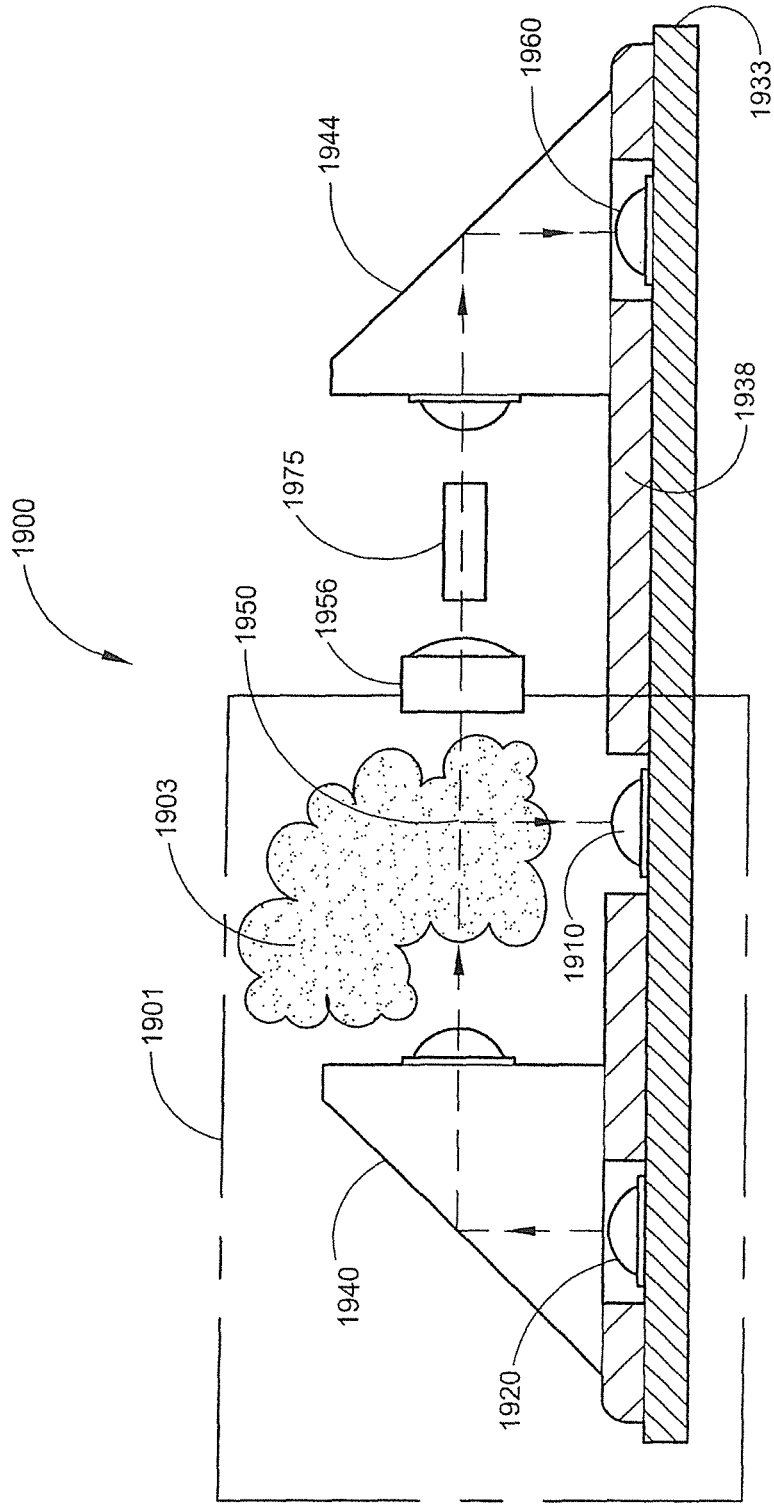
FIG. 21 is an illustration showing ONE MICROSIR CO sensing element (1975) positioned in edge-view orientation for increased sensitivity to low CO concentration for aiding in early fire and/or smoke (1903) detection application

FIG. 21 is an illustration showing ONE MICROSIR CO sensing element (1975) positioned in edge-view orientation for increased sensitivity to low CO concentration for aiding in early fire and/or smoke (1903) detection application. The smoke 1903 enters the chamber and some of the particles scatter photons from the LED 1920, which passes through the prism 1940 before hit the smoke particles. Some of the photons 1950 are scattered at 90 degrees and hit the photodiode 1910, which can be used to trigger an alarm if the threshold of smoke is reached such as 5% smoke. Other photons 1950 continue straight though a lens or window 1956 and then pass through the sensor 1975. Some of the photons 1950 are absorbed proportional to the CO hazard and these remaining photon 1950 pass through a second prism 1944 and are monitored by a second photodiode 1960. The signals of CO and smoke may be combined such that the CO sensing of 20 ppm can make the smoke sensor threshold change to a more sensitive reading such as 4%. In addition, if the CO rises rapidly to some level for example 40 PPM then the smoke may be made even more sensitive to some lower levels such as 2% smoke obscuration. The smoke chamber is open to smoke but not light. Vents (no shown) are used to block the light from entering and let the smoke go in to the smoke chamber 1901. The CO chamber will be sealed from the air and smoke entry using a diffusion type getter (not shown). The getter system is the subject of other patents such as U.S. Pat. No. 6,251,344 B1.

The LED 1920 and the photodiodes 1910 and 1960 are surface mount type and are fixed to the printed circuit board 1933.

Figure 22:
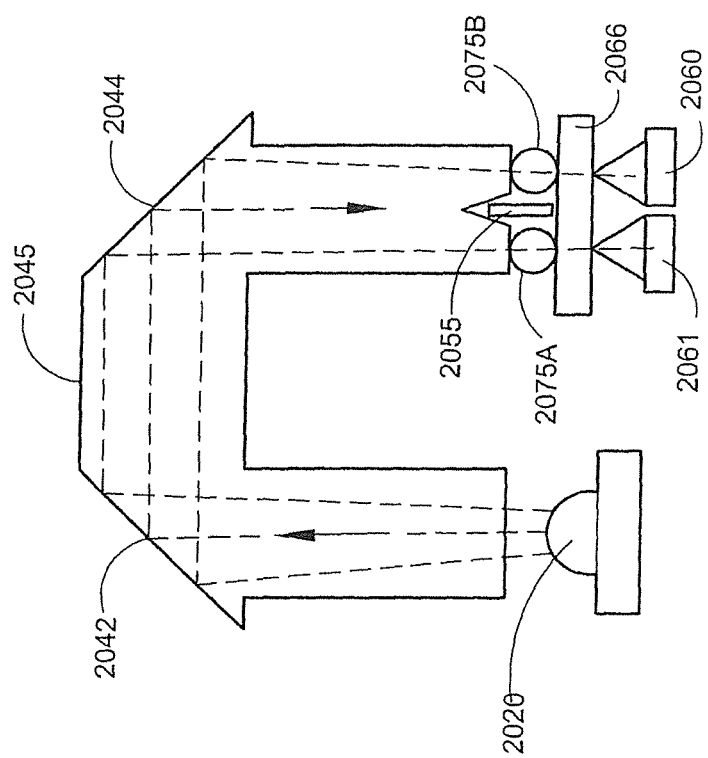
FIG. 22 is an illustration for explaining the "Theory of Operation of MICROSIR involving TWO sensing elements positioned in edge-view orientation" for increased sensitivity within a wider range of humidity and temperature.

FIG. 22 is an illustration for explaining the "Theory of Operation of MICROSIR involving TWO sensing elements positioned in edge-view orientation" for increased sensitivity within a wider range of humidity and temperature for unconditioned space. The LED 2020 is surface mount type and fixed to the PC board not shown. The photons 2030 are emitted from the LED 2020 and travel through the lightpipe 2045 as shown reflecting off of surface 2042 and 2044. The photons 2030 travel either side of the window 2055 and pass through sensing element 2075A and 2075B. Some of the photons are absorbed and other photons continue through the window 2066 and strike either photodiode 2061 or 2060. The photodiode measure the CO hazard and the signal is given to a microprocessor not shown. The circuit and the micro provide an alarm not shown.

Figure 23:
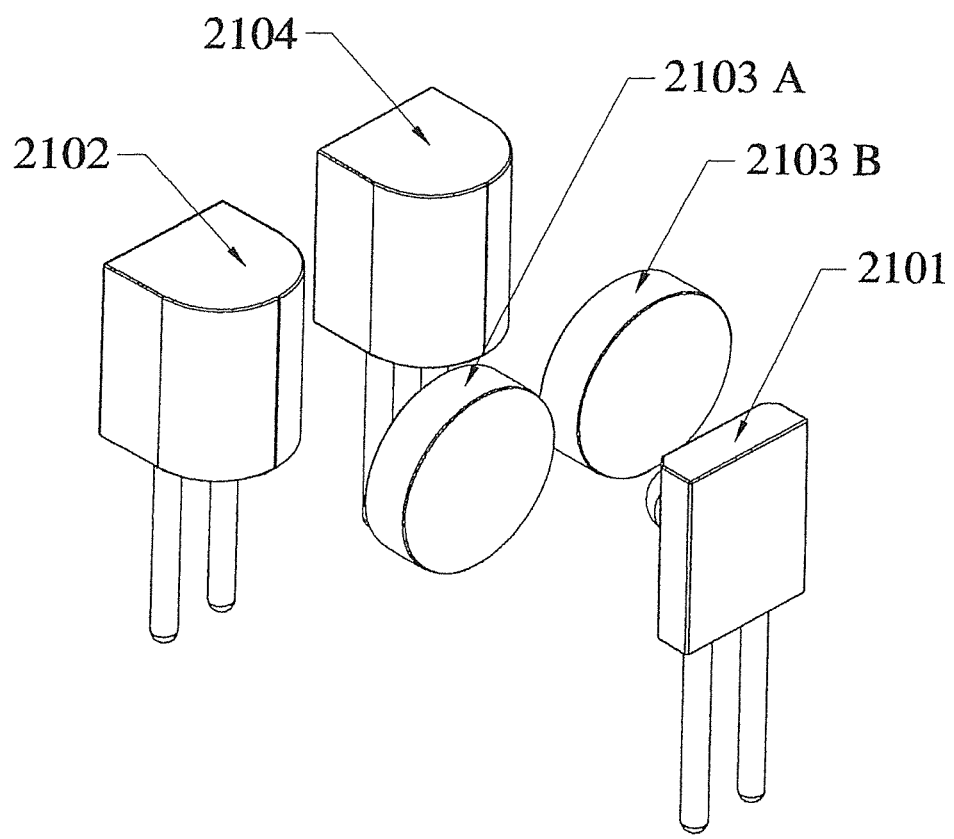
FIG. 23 is an illustration showing two CO sensing elements (2103 A and B) in face-view orientation between one LED 2101 and two photodiodes 2104 and 2102.

FIG. 23 is an illustration showing two CO sensing elements (2103 A and B) in center-view orientation between one LED 2101 and two photodiodes 2104 and 2102. One advantage of this system as shown in FIG. 23 is that one sensor may have a high threshold and one a lower level response to provide both fast response and fast regeneration not shown. The sensors 2103 A and 2103 B will regenerate at different speeds. The LED 2101 emits photons (not shown) that pass through both sensing elements 2103A and B and Strike the photodiode 2102 or 2104 where sensor 2103 A is more sensitive to CO it will respond first. As some of the photons are absorbed by 2103A the photodiode measure the CO hazard with the aid of the circuit and microprocessor not shown. The alarm can be sounded by reaction from one or both sensors 2103 A and B. When it is cold the sensor 2103 A regenerates slowly; however, 2103 B regenerates much faster. Therefore the logic circuit uses the fats regenerating sensor not shown. In this way the sensor arrangement can pass the new European standard.

Figure 24A:
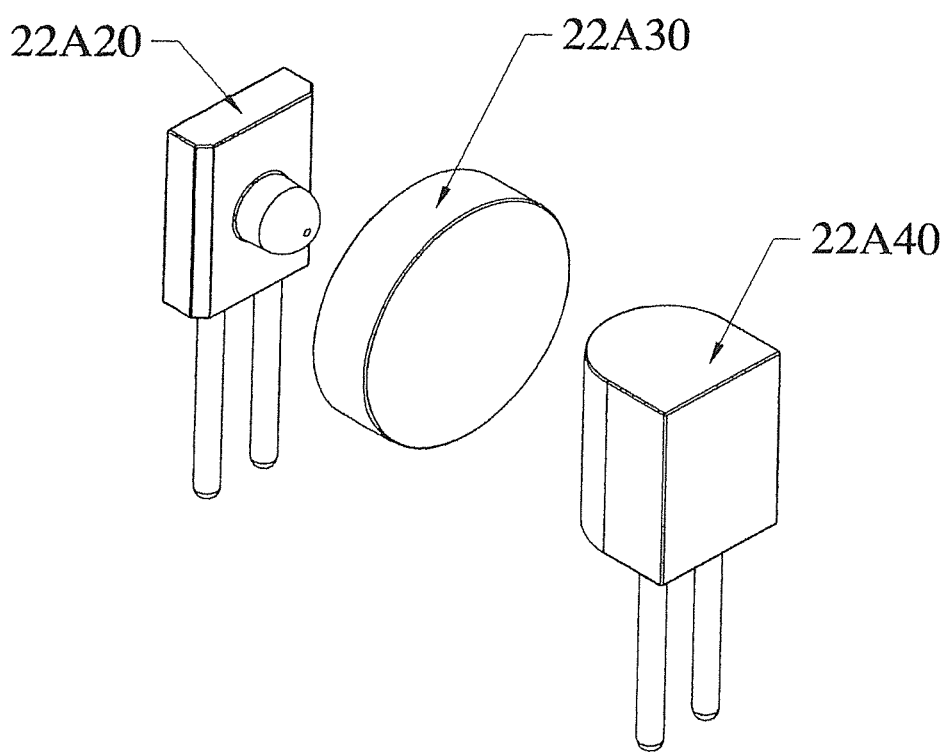
FIG. 24A is an illustration for explaining the "Theory of Operation of SIR-01," one sensing element 22A30 positioned in face-view orientation between an LED 22A20 and a Photodiode 22A40.

FIG. 24A is an illustration for explaining the "Theory of Operation of SIR-01," one sensing element 22A30 positioned in center-view orientation" between an LED 22A20 and a Photodiode 22A40. The LED 22A20 emits photons not shown. The photons pass through the center of the sensing elements 22A30 where if CO is present (not Shown) causes the photon to be absorbed. Some photons continue to the photodiode 22A40. The circuit not shown then measure the amount of infrar4ed photons and with the help of the software in the microprocessor (not shown) calculates if there is a need for alarm and then if so actuate the alarm beeper not shown.

Figure 24B:
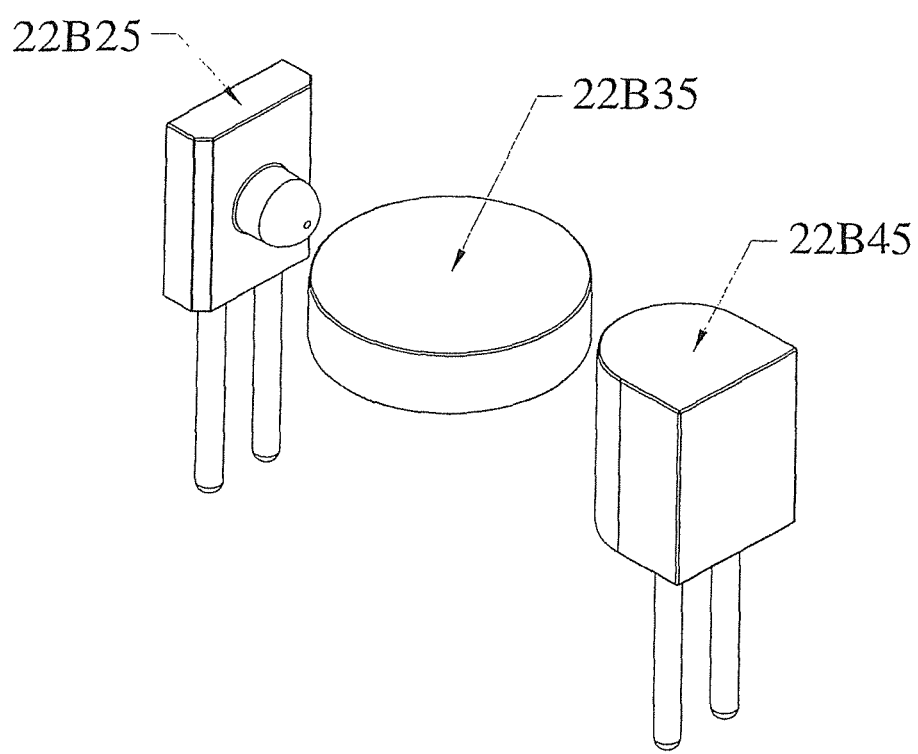
FIG. 24B is an illustration for explaining the "Theory of Operation of SIR-01," one sensing element 22B35 is positioned in edge-view orientation between the LED 22B25 and the Photodiode 22B45.

FIG. 24B is an illustration for explaining the "Theory of Operation of SIR-01," one sensing element 22B35 is positioned in edge-view orientation" between the LED 22B25 and the Photodiode 22B45. This arranges is very useful for passing the Japanese standard and for sensing fires in combination with smoke to produce an enhanced fire detection device or alarm. The sensor changes more rapidly such that a sensor can respond to 550 PPM in 30 seconds. In addition test were conduct in various fires and it was found that each fire test being a standard European fire test produce CO such that the sensor could detect it.

Figure 25:
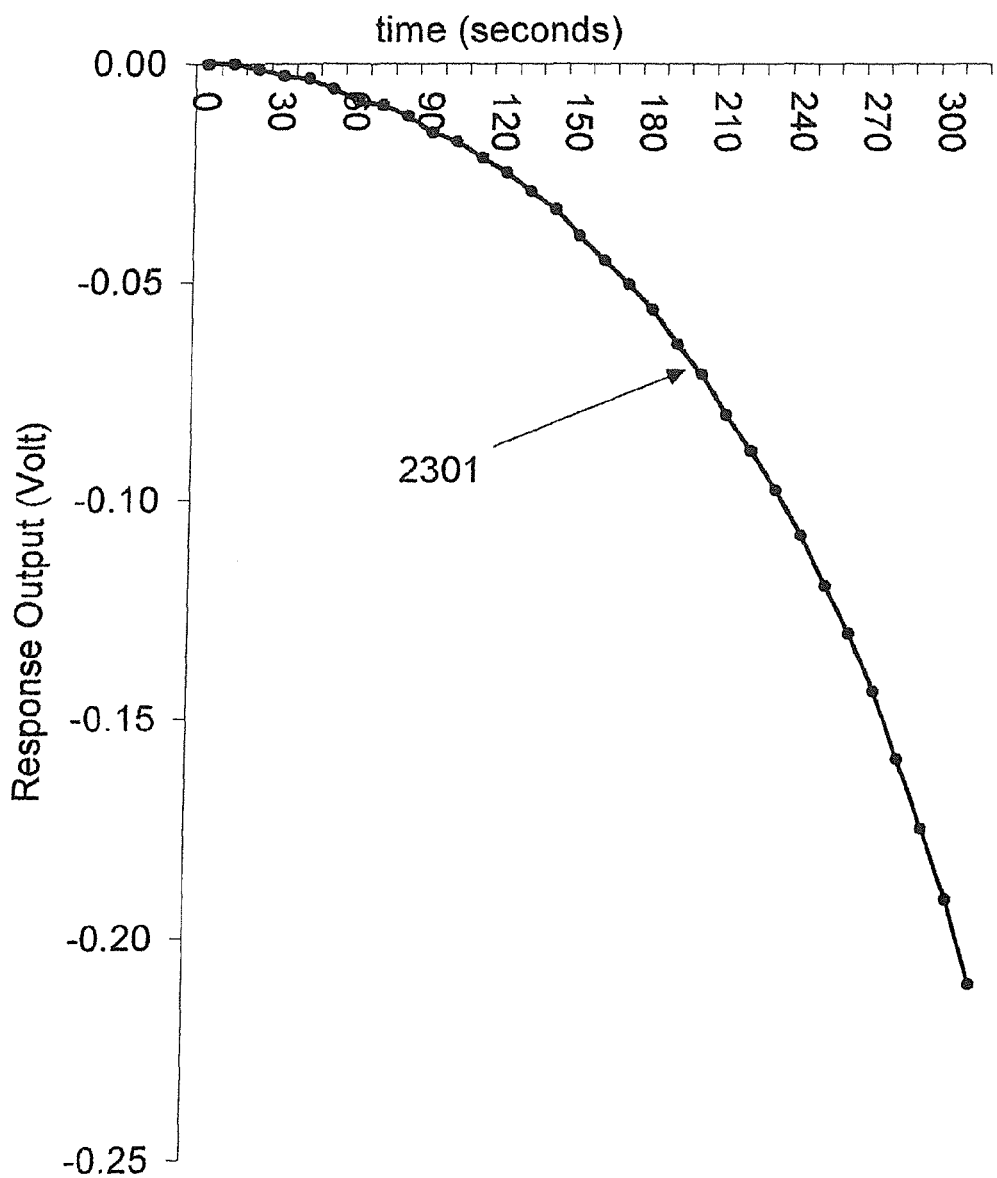
FIG. 25 is graphical representation showing IMPROVED response characteristics of M1-01e with one S50 single sensing element positioned in an edge-view orientation, in response to CO ramp of 5 ppm CO every 30 seconds, from 0 to 40 ppm CO. It is a proof-of-concept result demonstrating the viability of FIG. 19.

FIG. 25 is a graphical representation showing a response characteristic of ONE mini-sized CO sensor from the S50 sensor series (2301) to a rise in CO ramping of 5-ppm every 30 seconds from 0 to 40 ppm CO ppm. The mini-sized sensing element was prepared according to example 11 (preferred embodiment 10) and was positioned in an edge-view orientation similar to that, which is depicted in FIG. 24B (22B35), or exactly as depicted in FIG. 1A but with the sensing element 105 (FIG. 1A) rotated 90°. This assembly construction is referred to as M1-01e (e=edge-view orientation) at 50±20% RH and 23±3° C. Like those samples in FIGS. 12 to 16, the assembled samples were also mounted on the same type of 8UP-MICROSIR-voltage output board for this test. CO was injected at a rate of 5 ppm per 30 seconds to 40 ppm. Clearly, the S50 sensor M1-01e Model can detect CO rising at rate of 5 ppm per every 30 seconds. This is good for early fire detection and elimination of false alarm. The elimination of false alarm comes about by using the input from both CO and particulate and even optionally heat. The percent obscuration of say 6% is detected as a fire with a CO ramp to 15 to 20 PPM in 2 minutes. If the CO is 30 PPM then one can go off earlier by make the logic point of obscuration 5%. In addition if CO is rising rapidly to 40 PPM then the software logic allow alarm at 4% obscuration and so on.

Figure 26:
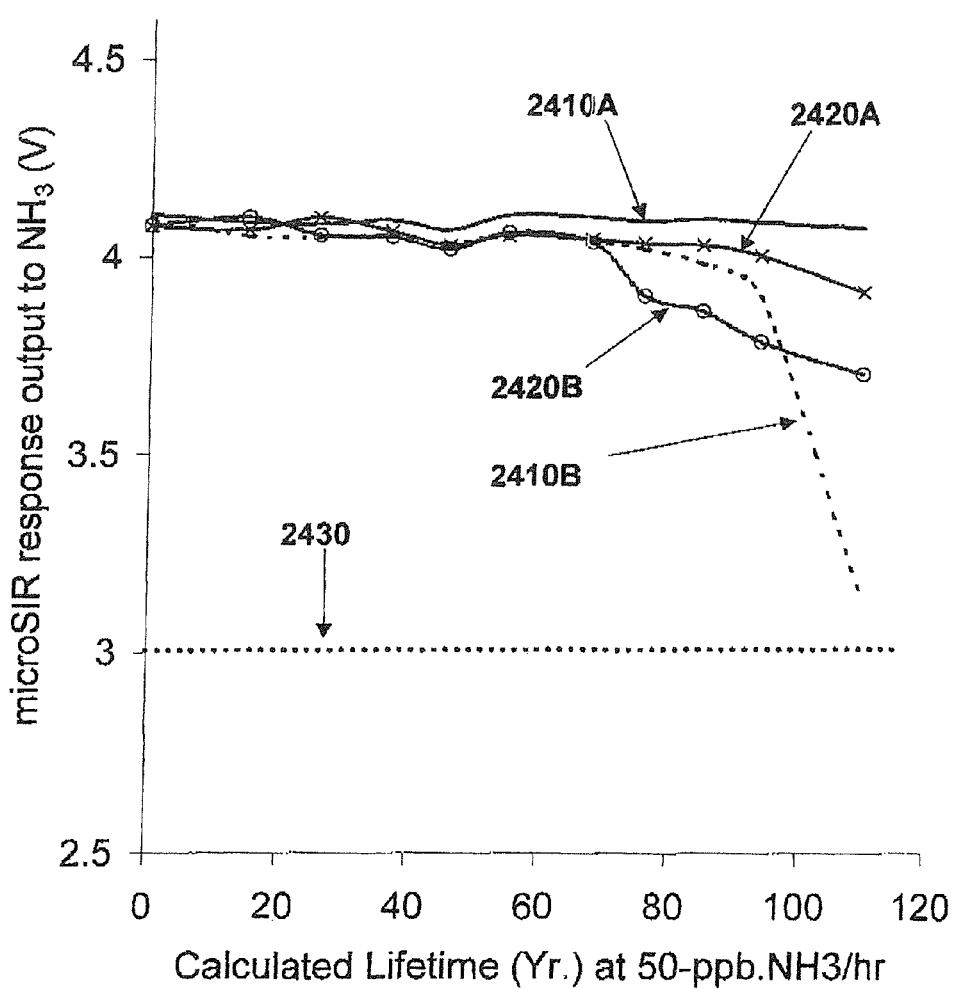
FIG. 26 is graphical representation showing response characteristics of M1-01 and M3-01 with varying amount of acid-coated activated charcoal for removing ammonia from air and/or air containing CO before reaching the sensor. Without the ammonia remover, both SIR and MICROSIR CO sensor are expected to have shorter lifetime.

FIG. 26 is graphical representation showing IMPROVED resistance to ammonia damage in M1-01 and M3-01 MICROSIR systems with respect to varying amount of acid-coated activated charcoal sensor used. Ammonia is a known killer of both MICROSIR and SIR CO sensors. Therefore, both the SIR and MICROSIR systems are equipped with getter systems to remove ammonia and/or amine from the incoming air sample (730 of FIG. 9) before it reaches the sensor. For M1-01 MICROSIR system, this improved getter system is 715 of FIG. 9, which is placed in the gas-path opening before the sensing element 705. The getter system 715 may comprise materials that remove basic gases such an ammonia/amine as well as other gases and vapors such as those of volatile organic compounds (VOCs). In the case of M3-01 MICROSIR system, the getter system is 103 of FIG. 1A. Like those samples reported in FIGS. 12 to 16, the assembled samples were also mounted on the same type of 8UP-MICROSIR-voltage output board for this test. However, NH3 gas exposed to the samples instead of CO. Since ammonia is the sensor killer, the reverse response is desirable. That is, better getter systems are ones that lead to longer time for sensor-ammonia response output to reach a predetermined sensor end-of-life 2430 of FIG. 26. Give the same type and amount of ammonia getter material, M1-01 MICROSIR systems (2410A, 2410B) are better than M3-01 (2420A, 2410B) systems. 2410A and 2420A contain the same amount and type of getter material. Likewise, 2410B and 2420B also the same amount and same type of getter material. 2410A and 2420A (0.08 g each) contained almost twice the mount that of 2410B and 2420B (0.15 g each). The getter better used was 10% porous activated charcoal beads (0.65-0.85 mm diameters, coated with 10-13% $H_3PO_4$ by weight) However, it appears that the design of the M1 housing utilizes the getter material more efficiently than does that of M3. In the SIR-1 (not shown) and SIR-02 (not shown) systems, 0.08 g acid-coated have been shown to last ~60 to 80 years at same 50-ppb.NH3.$Hr^{-1}$ ammonia background.

The present invention also includes a combined-sensing system adapted for sensing at least one target gas and smoke. It is understood that "smoke" as used herein includes visible vapor, gases, and particulates emitted by a burning or smoldering substance, including gray, brown or blackish mixture of vapor, gases, and particulates (including carbon particles) resulting from combustion or pyrolysis (e.g., resulting from the combustion of wood, peat, coal, or other organic matter). In the embodiment of FIGS. 27A-27G, a combined-sensing system 1300 includes many if not most of the features and structures of the aforementioned system 100 along with adaptations and modifications, as described below, for detection of smoke, or at least suspended particles resulting from combustion. In that regard, the above description of the system 100 and its components and structures provided in the foregoing paragraphs are incorporated herein, whereby similar features and structures are identified by similar reference numbers.

The system 1300 includes a housing 1306, for example, of molded plastic, configured with a controlled gas sensor chamber 1311 storing one or more gas sensors 1305 (e.g., in a disk shape having a first and second circular faces and a circumferential edge), and a treatment chamber 1310, wherein air outside the housing is received in the gas sensor chamber 1311 via a defined gas path that routes the air through the treatment chamber 1310 where the air is exposed to at least one treatment component of the system before the air reaches the sensor 1305 in the gas sensor chamber 1311. Treatment components of the system 1300 include a getter 1303 and a combined sensor detection assembly 317 to enable optical sensing of the presence of both a threshold concentration of a target gas and a threshold concentration of suspended particles.

Figure 27A:
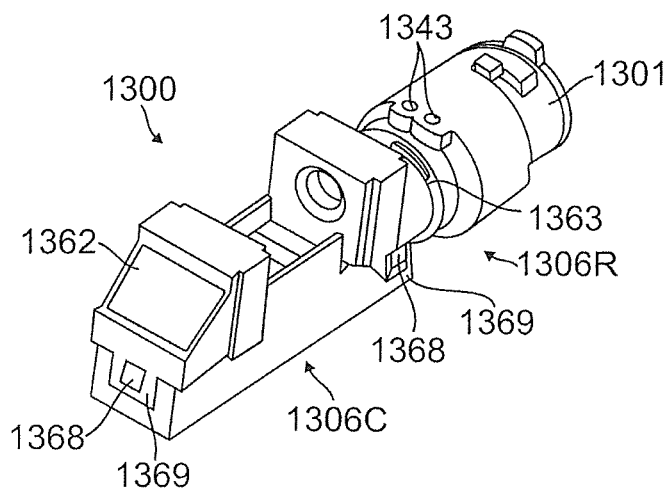
FIG. 27A is a perspective view of a gas and smoke sensor system, as assembled, in accordance with an embodiment of the present invention.
Figure 27B:
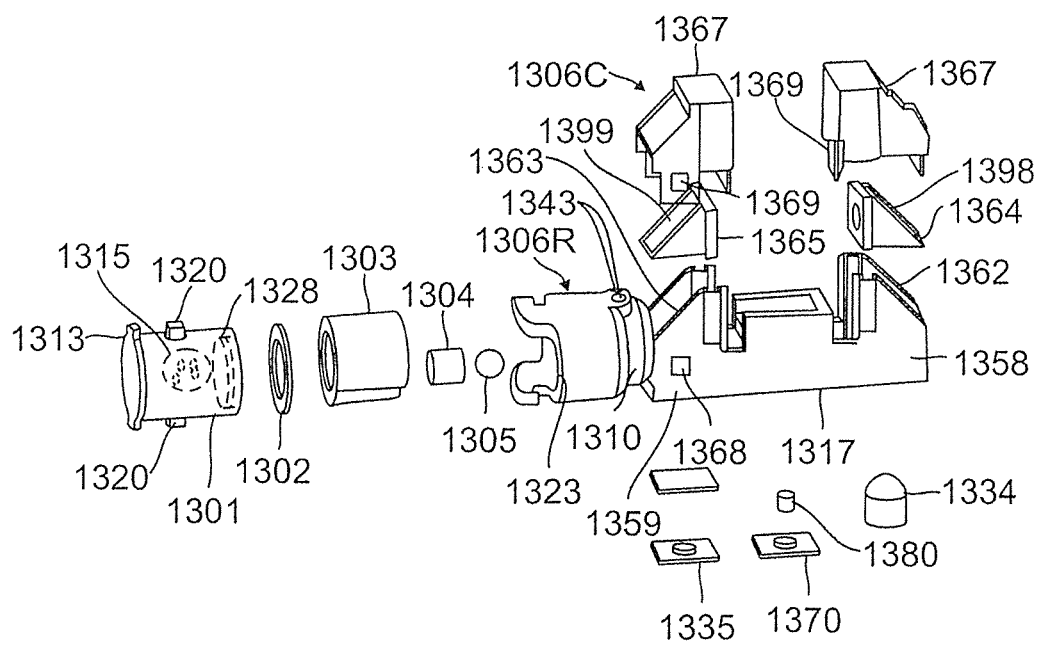
FIG. 27B is an exploded perspective view of the system of FIG. 27A.
Figure 27C:
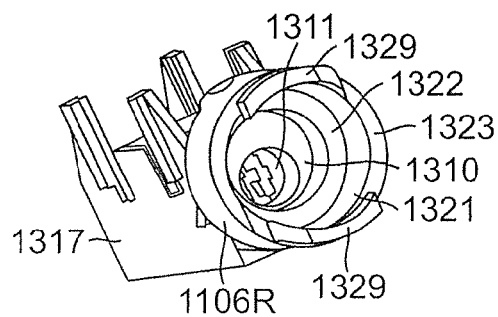
FIG. 27C is a perspective view of the system of FIG. 27A without a reservoir assembly.

With reference to FIGS. 27B and 27C, the housing 1306 includes a receiving portion 1306R at one end and a chamber portion 1306C at another end. The housing 1300 also has pins 1382 and apertures 1383 (FIG. 27G) for mounting on a circuit board (now shown). The receiving portion 1306R is configured with a cavity 1321 and an opening 1323 leading to the cavity 1321 in which the reservoir assembly 1301 is inserted. In relation to the system 100 as described above, the reservoir assembly 1301 is similarly received in the cavity 1321 and releasably locked with the receiving portion 1306R. The reservoir assembly 1301 contains chemical substances(s) 1315 including the humidity-controlling substances, as described above. An end wall of the reservoir assembly 1301 is covered by a hydrophobic membrane 1328 that is welded or otherwise affixed to an inside surface of the end wall. The hydrophobic membrane 1328 prevents penetration of liquids and solids and thus serves to contain the liquid mixture and solution 1315 inside the reservoir assembly 1301 while allowing free exchange of gases and vapors between reservoir assembly 1301, the treatment chamber 1310 and the sensor chamber 1311.

The chamber portion 1306C includes the treatment chamber 1310, the gas sensor chamber 1311 and the dual sensor detection assembly 1317. The treatment chamber 1310 is situated between the receiving portion 1306R and the gas sensor chamber 1311 such that the treatment chamber 1310 connects the receiving portion 1306R and the chamber portion 1306C and allows fluid or gaseous communication therebetween.

With reference to FIG. 27C, the treatment chamber 1310 is structurally similar to the treatment chamber 110 as described above. And because the treatment chamber 1310 has a lesser cross-section (or diameter) than the cavity 1321, an annular flange 1322 is formed at the junction between the cavity 1321 and the treatment chamber 1310 against which a gasket 1302 abuts to seal the treatment chamber 1310 when the reservoir assembly 1301 is received in the cavity 1321 and locked in the receiving portion 1306R via locking pins 1320 in engagement with grooves 1319.

The gas sensor chamber 1311 is structurally similar to the gas sensor chamber 111 as described above but the dual sensor detection assembly 1317 while featuring many structures similar to the sensor detection assembly 117 provides structures and components that enable detection of smoke, as described below.

With reference to FIGS. 27D-27G, the assembly 1317 is elongated having a distal or entry end 1358, a proximal or exit end 1359 and a mid-portion 1360 extending therebetween forming distal corner 1362 and proximal corner 1363. The assembly 1317 extends off the treatment chamber 1310 such that the gas sensor chamber 1311 (FIG. 27C) resides at or in the proximal end 1359. The assembly 1317 defines an optical path that is U-shaped (e.g., trapezoidal) with a first linear section through the distal end 1358 along direction 1338 generally perpendicular to the longitudinal axis 1314, a second linear section through the mid-portion 1360 in the direction of the longitudinal axis 1314, and a third linear section through the proximal end 1359 along direction 1339 generally opposite to direction 1338. The assembly 1317 also defines a smoke chamber 1361 in the mid-portion 1360 between the ends 1358 and 1359 through which the second linear section of the optical path extends. The smoke chamber 1361 defines a space that can be occupied by air that may contain suspended particles as an indicator of smoke or fire. Advantageously, the smoke chamber is configured so that the space is intersected by the photon pathway such that photons traveling along the pathway are employed for sensing both target gas and smoke.

As shown in FIG. 27B, a light source 1334 is positioned to provide light or a beam of photons (used interchangeably herein) into the entry end 1358. In one embodiment, the light source is an LED configured to emit pulses of photons in the near IR in the range of about 700 nm to 980 nm. Lens 1364 with an angled reflective surface 1398 is provided at the corner 1362 to generally redirect the photons traveling through the distal end 1358 toward the mid-section 1360. Lens 1365 with an angled reflective surface 1399 is provided at the corner 1363 to generally redirect the photons traveling through the mid-section toward the exit end 1359 where the photons strike and pass through gas sensor 1305 in the gas sensor chamber 1311 before reaching a light detector 1335, for example, a photodiode. To secure and protect each lens, a respective lens housing 367 is provided which covers each lens and is engaged with the respective end, for example, by holes 1369 that are engaged by tabs 1368 extending from the ends 1358, 1359.

At least one gas sensor 1305 is situated in the sensor chamber 1311. The sensor may have a disk shape with a diameter of about 0.100 inch and a thickness of about 0.050 inch, although it is understood that the thickness may range between about 0.025 inch to about 0.10 inch. In the illustrated embodiment, the sensor is positioned in edge-view to the optical path such that the photon beam strikes the circumferential edge of the sensor and passes through the greatest dimension or diameter of the sensor. To that end, the exit end 1359 provides a slit or opening 1366 (best seen in FIGS. 27D and 27E) leading into the gas sensor chamber 1311 that is shaped and sized in close conformity to the abutting sensor 1305 so as to limit photons entering the sensor chamber 1311 to only those that strike and pass through the sensor disk. By so shrouding the photon entrance to the gas sensor chamber 1311, the photons detected by the gas photodetector 1335 are more accurately representative of the sensor's reaction to the presence of the target gas.

As discussed above, the sensor 1305 reacts to the presence of at least a threshold level of a target gas, for example UL 2034, CO below or at 30 ppm is no reaction and the other are according to UL or whatever standard. In one embodiment, the software is adapted to detect different levels over different periods of time such as the European standard:
 at 30 ppm for 120 minutes no alarm allowed;
 at 50 ppm must alarm between 60 and 90 minutes;
 at 100 ppm must alarm between 10 and 40 minutes; and
 at 300 ppm must alarm before 3 minutes,
which is very different from the US standard, and the change in optical absorption or transmissivity of the sensor 105, for example, darkening or increase in opacity, over a period of time (namely, the rate of change) is proportional to the target gas or CO concentration over that period of time between readings. Likewise, the sensor can be read or sampled at a predetermined rate ranging between about every few seconds to about every 30 to 45 seconds, depending on design type and objective of the application. These factors and parameters can be controlled by suitable software executed by a microprocessor provided on the circuit board 1336.

In accordance with another feature of the present invention, the photon beam provided by the light source also passes through the smoke chamber 1361 defined in the mid-section 1360 of the assembly 1317 between ends 1358 and 1359. Without smoke or suspended particles thereof, the photons merely pass through the smoke chamber 1361 from the reflective surface 1398 toward the reflective surface 1399 of the corner lenses 1367. However, with smoke or suspended particles present in the smoke chamber 1361, a portion of the photons in the beam is scattered away from the optical path, some of which are scattered in a generally perpendicular direction toward a smoke photodetector 1370 (FIGS. 27B and 27H), for example, a second photodiode, positioned offset from the optical path in an opening 1371 formed in the mid-portion 1360. In the illustrated embodiment, the second photodiode is positioned generally between the gas photodetector 1335 and the light source 1334. Thus, a change in intensity of light or amount of photons detected by the second photodiode 370 indicates the presence of suspended particles and the likelihood of smoke and/or fire.

Figure 27D:
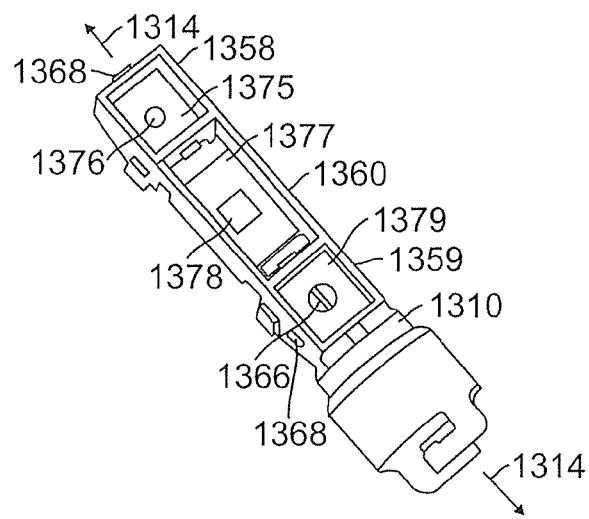
FIG. 27D is a bottom plan view of the system of FIG. 27A without a reservoir assembly, a light source, a gas photodetector or a smoke photodetector.
Figure 27E:
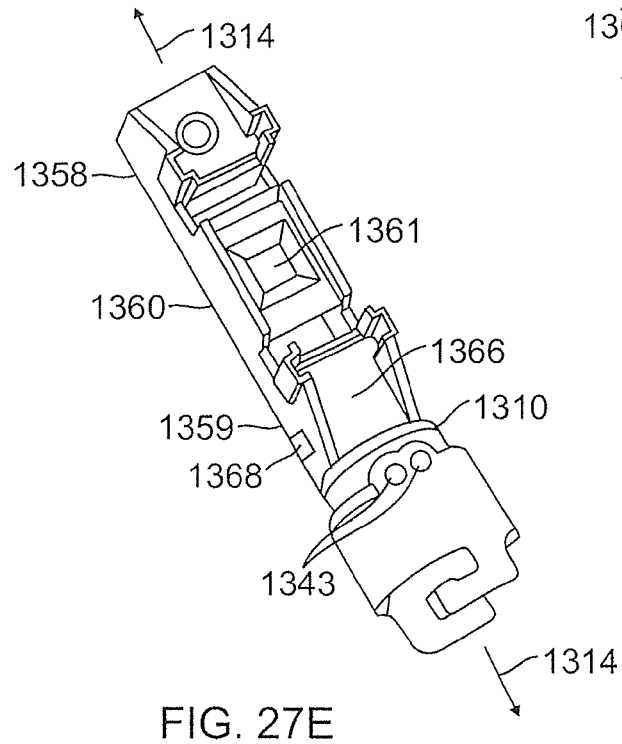
FIG. 27E is a top view of the system of FIG. 27D.
Figure 27F:
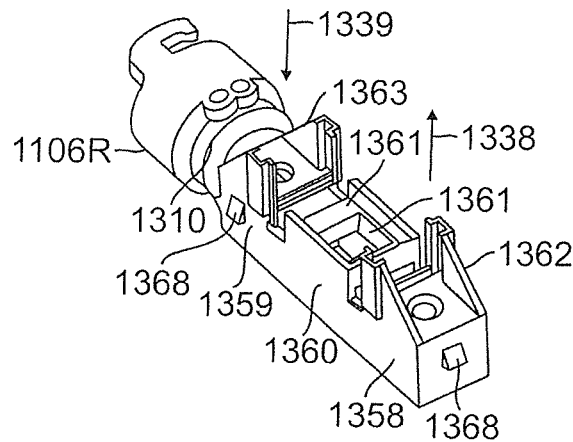
FIG. 27F is a perspective view of the system of FIG. 27D.
Figure 27G:
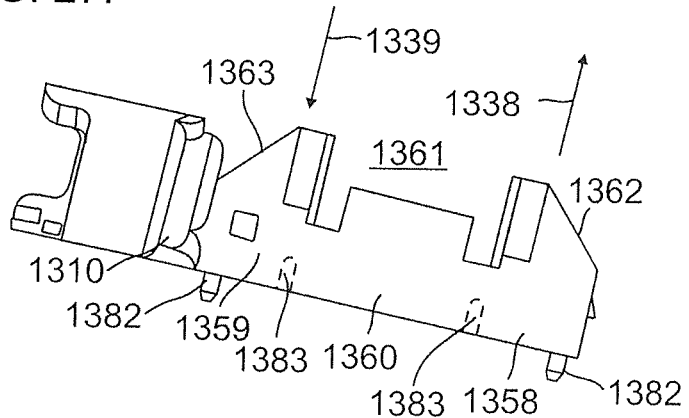
FIG. 27G is a side elevational view of the system of FIG. 27D.
Figure 27H:
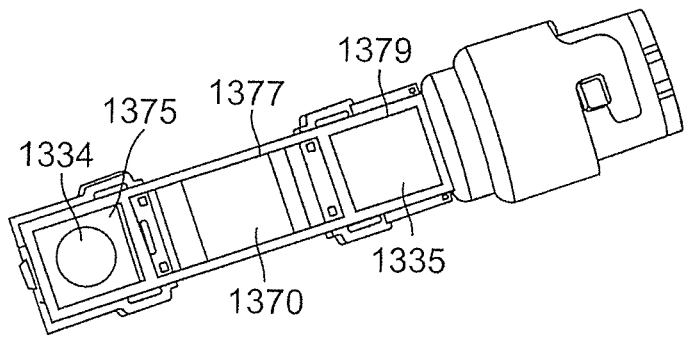
FIG. 27H is a bottom plan view of the system of FIG. 27A.

With reference to FIGS. 27D and 27H, the light source 1334 is nested in a recess 1375 formed at the entry end 1358 of the assembly 1317. The recess 1375 communicates an opening 1376 through which photons pass from the light source 1334. The smoke photodetector 1370 is nested in a recess 1377 formed in the mid-portion 1360. The recess 1377 communicates with an opening 1378 formed in the mid-portion 1360 through which the photons scattered by smoke pass. A light pipe lens 1380 (FIG. 27B) may be provided between the opening 1378 and the smoke photodetector 1370. The gas photodetector 1335 is nested in a recess 1379 formed in the exit end 1358 of the assembly 1317. The recess 1379 communicates with the slit opening 1366 which shrouds the sensor 105 for photons exiting the corner lens 1365. The light source and photodetectors may be surface mounted on the circuit board or they may be mounted in through-holes formed in the circuit board.

It is understood that the sensor 305 may also be oriented face view or edge view toward the photon beam. The edge view orientation as shown in FIG. 27B is used for early fire detection as described in European standards, including Loss Prevention Standard 1265 (Standard for Requirements and Testing Procedures for the LPCB Approval and Listing of Carbon Monoxide Fire Detectors Using Electrochemical Cells). For that application, a suitable sensor provides early detection of several types of fires by detecting the rapid rate of CO rise generally in the zero to 60 PPM range.

Figure 28A:
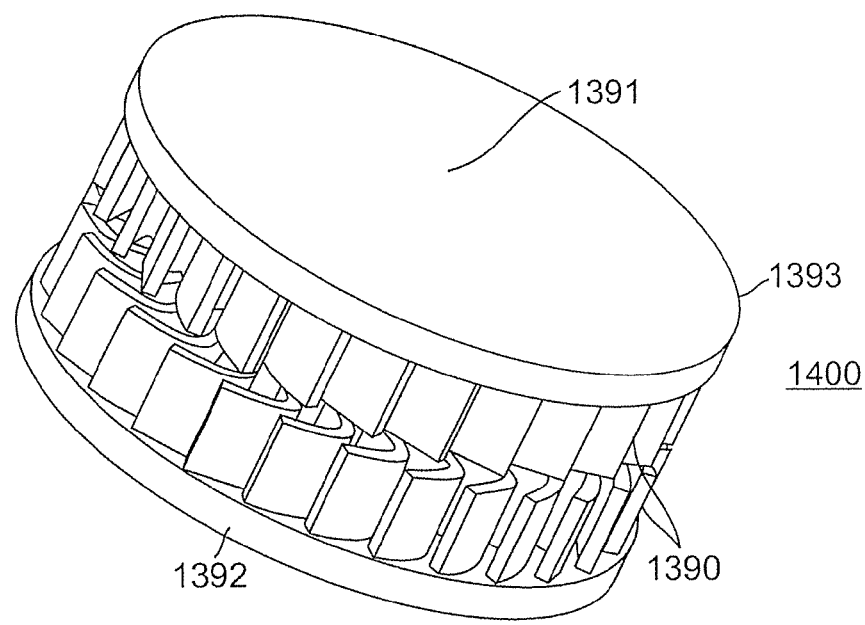
FIG. 28A is a perspective view of the alarm housing in accordance with one embodiment of the present invention.
Figure 28B:
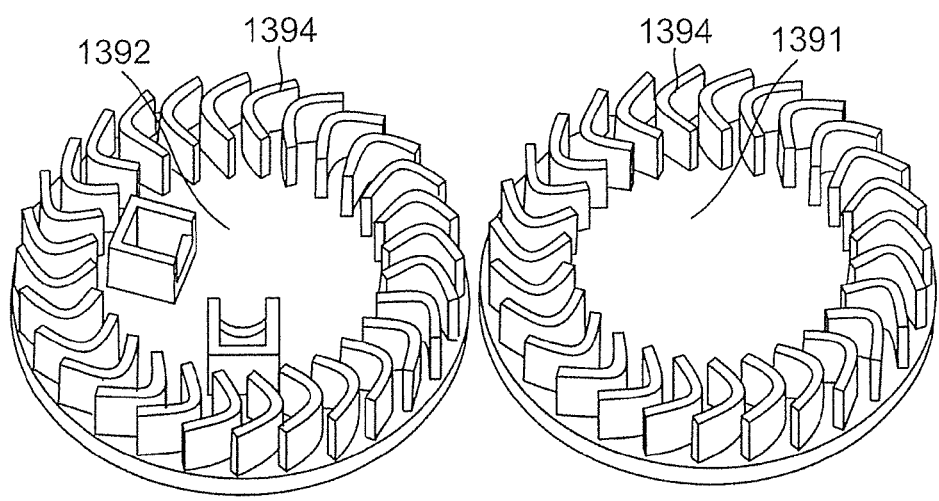
FIG. 28B is a perspective view of a top lid and a bottom lid of the alarm housing of FIG. 28A.
Figure 28C:
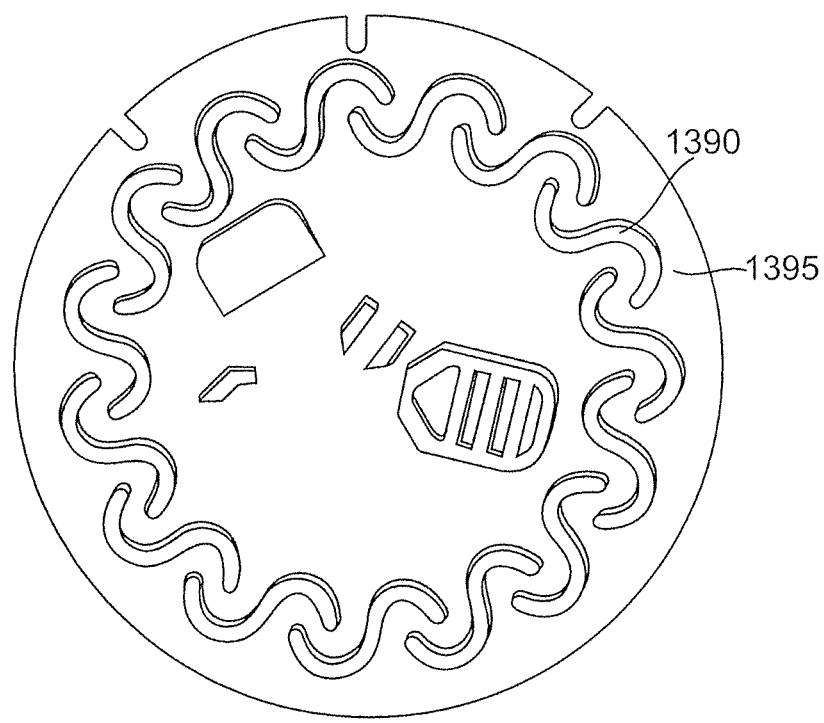
FIG. 28C is a perspective view of a lid of alarm housing, in accordance with another embodiment of the present invention.

It is noted that the smoke chamber 1361 is open, exposed and not covered or sealed by the housing 1300. Where the system 1300 and housing 1301 are enclosed in an alarm housing 1400, as shown in FIG. 28, air travels to the smoke chamber 1361 from outside the alarm housing 1400 via a plurality of dividing fins 1390 extending between a first lid 1391 and a second lid 1392 as shown in FIG. 28A. The fins 1390 are radially distributed 360 degrees along a circumferential edge 1393 of the housing. Advantageously, the fins are configured for free air exchange without significant transmission of light. Each fin has a cross-section with at least one nonlinear portion to prevent significant transmission of light and is spaced apart from adjacent fins to allow free air exchange between inside and outside of the alarm housing. The cross-section of each fin may be identical or different from the other fins. In the embodiment of FIG. 28B, all of the fins have an identical cross-section, namely a V-shaped cross section 1394, and are uniformly spaced apart. In the embodiment of FIG. 28C, all of the fins have an identical cross-section, namely, an S-shaped cross-section 1395, and are uniformly spaced apart. There may be more than one level of fins (for example, two levels) along the circumferential edge of the alarm housing as illustrated, where each level of fins may be oriented oppositely of each other. In the embodiment shown in FIG. 28A; the fins of one level open clockwise whereas the fins of another level open counterclockwise.

FIG. 29 is a graphical representation showing comparative response characteristics of the S66e CO sensing chemistry on SPS disks with different concentrations of boron oxide coating and without (control). The sensors were made according to Example 12A. These were responses to 70 ppm CO for 4 hours at minus (−) 40° C. as specified in UL 2034 Section 69.1b, except there was no prior 30 days preconditioning at 66° C. Both the software and hardware used were the 2011 UL approved "9SG1bb_36" for SIR CO detection system. According to FIG. 29, the response to CO is directly proportional to the concentrations of boron oxide coating ranging from zero 2901A (control), to 0.1N 2901B, to 0.5N 2901C, and to 1.0N boron oxide coating 2901D.

FIG. 30 is a graphical representation showing comparative response characteristics of the S66e CO sensing chemistry on SPS disks with different concentrations of boron oxide coating and without (control). The sensors were manufactured according to Example 12A. Shown are responses to 70 ppm CO for 4 hours at 66° C. and 40% RH following 4 days (instead of 30 days) of preconditioning at the same conditions, as specified in UL 2034 Section 69.1a. Both the software and hardware used were the 2011 UL approved "9SG1bb_36" for SIR. According to FIG. 30, the response to CO is proportional to the concentrations of boron oxide coating from zero 3001A (control), to 0.1N 3001B, and to 0.5N boron oxide coating 3001C.

Figure 31:
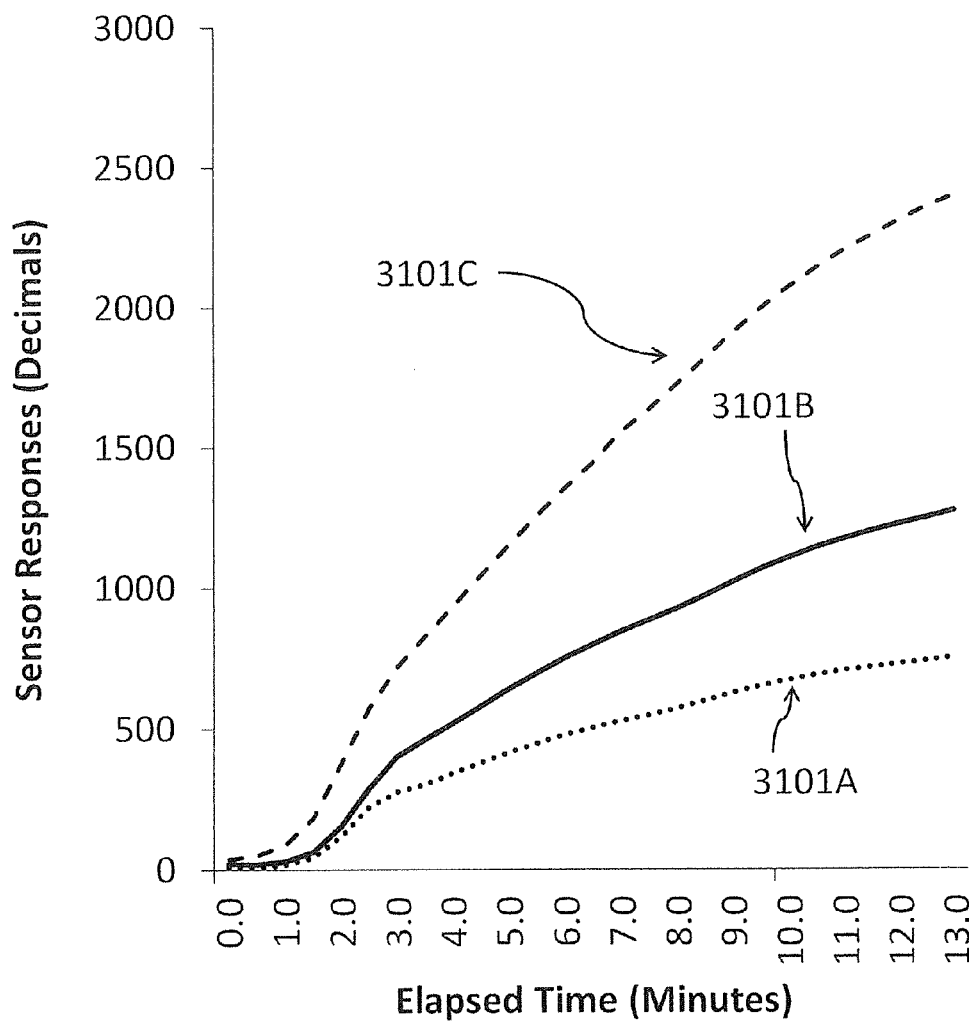
FIG. 31 is a graphical representation showing comparative response characteristics of the S66e CO sensing chemistry on SPS disks with different concentrations of boron oxide coating and without (control). The sensors were fabricated according to Example 12A. Shown are responses to 400 ppm CO for 15 minutes at 66° C. and 40% RH as specified in UL 2034 Section 69.1a, but with the preconditioning period of 4 days instead of 30. Both the software and hardware used were the 2011 UL approved "9SG1bb__36" for SIR. The response to CO is proportional to the concentrations of boron oxide coating ranging from zero 3101A (control), to 0.1N 3101B, and to 0.5N boron oxide coating 3101C.

FIG. 31 is a graphical representation showing comparative response characteristics of the S66e CO sensing chemistry on SPS disks with different concentrations of boron oxide coating and without (control). The sensors were fabricated according to Example 12A. Shown are responses to 400 ppm CO for 15 minutes at 66° C. and 40% RH as specified in UL 2034 Section 69.1a, but with the preconditioning period of 4 days instead of 30. Both the software and hardware used were the 2011 UL approved "9SG1bb_36" for SIR. The response to CO is proportional to the concentrations of boron oxide coating ranging from zero 3101A (control), to 0.1N 3101B, and to 0.5N boron oxide coating 3101C.

Figure 32:
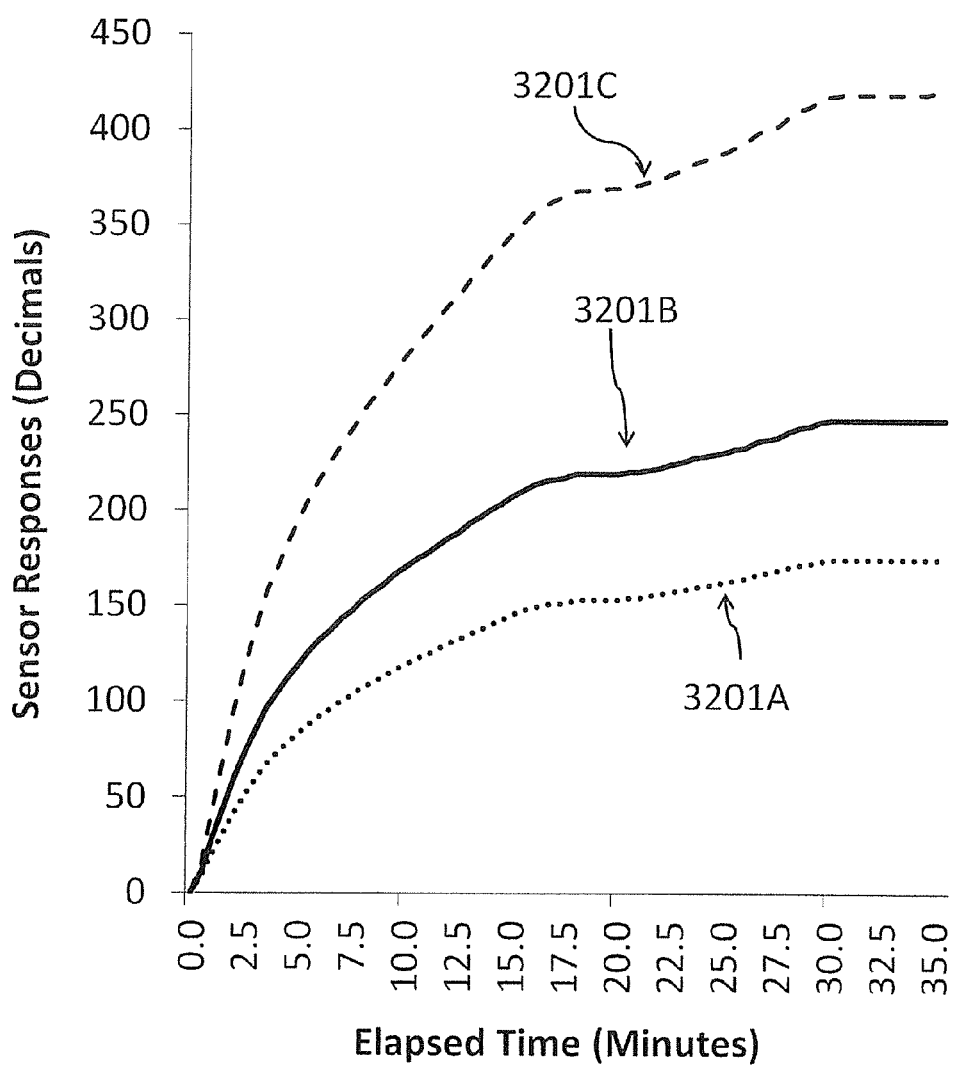
FIG. 32 is a graphical representation showing comparative response characteristics of the S66e CO sensing chemistry on SPS disks with different concentrations of boron oxide coating and without (control). These sensors were made according to Example 12A. Shown are responses to 150 ppm CO for 50 minutes at 66° C. and 40% RH as specified in UL 2034 Section 69.1a, but with the preconditioning period of four days instead of thirty. Both the software and hardware used were the 2011 UL approved "9SG1bb__36" for SIR system. The response to CO increases as the concentrations of boron oxide coating increase from zero 3201A (control), to 0.1N 3201B, and to 0.5N boron oxide coating 3201C.

FIG. 32 is a graphical representation showing comparative response characteristics of the S66e CO sensing chemistry on SPS disks with different concentrations of boron oxide coating and without (control). These sensors were made according to Example 12A. Shown are responses to 150 ppm CO for 50 minutes at 66° C. and 40% RH as specified in UL 2034 Section 69.1a, but with the preconditioning period of four days instead of thirty. Both the software and hardware used were the 2011 UL approved "9SG1bb_36" for SIR system. The response to CO increases as the concentrations of boron oxide coating increase from zero 3201A (control), to 0.1N 3201B, and to 0.5N boron oxide coating 3201C.

In summary, a miniature, lower cost optical sensing apparatus and method are provided for determining the concentration and/or hazard from a target gas by means of IR or visible photon monitoring one or more sensors that responds to carbon monoxide. The apparatus comprises a photon source optically coupled to the sensor and at least a portion of the photon intensity passing through the sensor is quantified by one or more photodiode(s) in a system, so that the photon flux is a function of at least one sensor's response to the target gas, e.g., transmits light through the sensor to the photodiode. The photo current from the photodiode is converted to a sensor reading value proportional to the optical characteristics of the sensors and is loaded into a microprocessor or other logic circuit. In the microprocessor, the sensor readings may be differentiated to determine the rate of change of the sensor readings and the total photons absorbed value may be used to calculate the CO concentration and/or dose. There are a number of methods to compute the CO hazard.

The major advantages of advanced MICROSIR over SIR include: 1. Lower cost (estimates saving of US$1.00 per sensor, 2. Better control of the gas path therefore more accurate and more precision and longer life 3. Better getter system therefore longer life (as shown by ammonia accelerated age tests), and 4. Better RESERVOIR SYSTEM THEREFORE BETTER humidity CONTROL AT BOTH LOW AND HIGH (as shown by sensor response curves).

5. The MICROSIR Edgeview is faster and meets the Japanese standard for CO and the European Standard for CO enhanced smoke detection, 6. More easily automated as the board of alarms use surface mount and MICROSIR is a surface mount part that attaches over surface mounted optics after the soldering, 7. Much small size and 8. Is now an approved UL recognized component.

The MICROSIR device can also be used to detect the CO, which may be combined with temperature and smoke in a very small package. The detection of one or more indicators such as smoke and CO; increases the sensitivity of the other indicators. Combining signals produces an improved fire detector comprising a CO sensor, heat and a smoke sensor in one unit. The smoke detection sensor may be either ionization or photoelectric either or both may be combined with the CO sensor to provide earlier warning to fire and reduce false alarms.

Many other modifications and variations will be apparent to those skilled in the art, and it is therefore, to be understood that within the scope of the appended claims the invention may be practiced otherwise than as specifically described. Some of the current competitive products on the market, which are battery-operated, use electrochemical cells for sensors. They are expensive, require frequent calibration because of tendency to drift, respond to interference gases causing many false alarms and have a short stable life. Some models using PEM membranes do not operate below zero very well and other EC cells use sulfuric acid, which cause corrosive gases to be emitted in hot conditions and can lead to fire condition. Metal Oxide Semiconductor sensors are another competitive technology used in CO alarm on the market today, the MOS sensor take very large amounts of power and therefore cannot be operated practical for most portable applications or for systems. Therefore, there is a need for a low cost, reliable, accurate, easy to use very low powered unit to detect CO level, as well as rate of change of the CO to low level for fire detection, to meet CO standards of various countries such UL 2034 and UL 2075 in the USA and CAS 6.19-01 in Canada. The MicroSIR is the only low cost sensor that can pass the Lawrence Berkeley National Laboratory (LBNL) false alarm tests. The low cost MICROSIR and smoke sensor combination can meet all these standards (LBNL and UL) at cost that are very competitive with MOS and EC sensor in combination with smoke technology and perform better, more reliably and with much few false alarms. The dual sensor can be used by itself or in combination with other sensors such as heat sensors.

What is claimed is:

1. A system for sensing a target gas, comprising
   at least one sensor having an optical property responsive to the target gas and comprising a substrate coated with boron oxide;
   a sensor chamber defining a sensor space in which the sensor is positioned, the space being configured in close conformity with the sensor;
   a treatment chamber configured with at least one opening to allow diffusion of air from outside the system into the treatment chamber, the air containing the target gas;
   a reservoir assembly having a grid portion, the reservoir assembly storing a chemical mixture;
   a sealed housing configured to provide gaseous communication between the sensor chamber, the treatment chamber and the grid portion of the reservoir assembly, the housing defining a gas path for the air from the at least one opening in the treatment chamber to the sensor chamber; and
   an optical detection assembly having a photon source and a photon detector, the photon source configured to emit photons at the sensor, the photon detector configured to receive photons transmitted through the sensor for detecting a change in the optical property of the sensor,
   wherein the treatment chamber is configured to expose the air to at least the chemical mixture in the reservoir assembly prior to the air reaching the sensor in the sensor chamber.

2. The system of claim 1, further comprising a getter positioned in the treatment chamber, wherein the air is also exposed to the getter before the air reaches the sensor.

3. The system of claim 1, wherein the grid portion is covered by a hydrophobic membrane allowing air and water vapor exchange without liquid penetration with the treatment chamber.

4. The system of claim 1, further comprising a circuit board, wherein both of the photon source and the photon detector are surface mounted on the circuit board.

5. The system of claim 1, wherein the optical property is optical transparency, optical transmission, optical obscuration, photon absorption or photon transmissivity.

6. The system of claim 1, wherein the chemical mixture of the reservoir assembly is adapted to maintain relative humidity in the treatment chamber at between about 15% to 90%.

7. The system of claim 1, wherein the optical detection assembly defines a generally U-shaped photon path between the photon source and the photon detector.

8. The system of claim 7, wherein the at least one sensor is oriented edgeview relative to the photon path.

9. The system of claim 7, wherein the at least one sensor is oriented faceview relative to the photon path.

10. The system of claim 1, wherein the photon source includes an LED.

11. The system of claim 1, wherein the photon detector includes a photodiode.

12. The system of claim 1, further comprising a smoke chamber configured to provide a smoke space for occupation by air-suspended particles, wherein the smoke space and the photon path intersect each other such that photons traveling along the photon path are scattered by the suspended particles.

13. The system of claim 12, further comprising a second photo detector configured to detect at least a portion of the scattered photons.

14. The system of claim 1, wherein the photon detection assembly is configured with a shroud for the photon detector.

15. The system of claim 1, wherein the photon detection assembly includes a light pipe passing the photons from the photon source toward the sensor.

16. The system of claim 15, wherein the light pipe is generally U-shaped.

17. The system of claim 15, wherein the light pipe has two angled reflective surfaces.

18. The system of claim 15, where the light uses prisms or mirrors to move the photon in the generally U shaped area for the CO sensing and in a 90 degree change for the smoke scattering beam which is one beam for both CO and smoke.

19. The system of claim 1, wherein the housing has a cavity configured to receive the reservoir assembly.

20. The system of claim 1, wherein the housing has prongs surrounding the at least one opening, the prongs configured to support a spray nozzle directed at the opening.

21. The system of claim 1, wherein the photon source is adapted to emit photons in the visible or infrared light spectrum.

22. The system of claim 1, wherein the chemical mixture of the reservoir assembly comprises a solid salt, a saturated salt solution, or a supersaturated salt solution.

23. The system of claim 1, wherein the chemical mixture of the reservoir assembly comprises a salt selected from the group consisting of manganese chloride, manganese bromide, and combinations thereof.

24. The system of claim 1, wherein the substrate of the at least one sensor comprises a high surface area porous substrate.

25. The system of claim 1, wherein the boron oxide coating has a thickness of about 1 Å to about 500 Å.

26. The system of claim 1, wherein the boron oxide coating is formed by soaking the substrate in a boric acid solution to impregnate the substrate, drying the impregnated substrate, and heating the impregnated substrate to convert the boric acid to boron oxide.

27. The system of claim 26, wherein the boric acid solution is about 0.1 N to about 2.1 N.

28. The system of claim 1, wherein the boron oxide coated substrate is coated with a mixture comprising at least one palladium salt, at least one molybdenum compound, at least one of copper chloride or copper bromide, at least two cyclodextrin complexing molecules, at least one soluble metal salt of bromide or chloride that does not include copper, at least one organic solvent, co-solvent, or compound including a trifluorinated organic anion, at least one soluble acid, and at least one oxidizer.

29. The system of claim 28, wherein the mixture comprises at least one material from Group 1, at least one material from Group 2, at least one material from Group 3, at least two materials from Group 4, at least one material from Group 5, at least one material from group 6, at least one material from group 7, and at least one material from group 8:
   Group 1: Palladium salts selected from the group consisting of palladium chloride, palladium bromide, $CaPdCl_4$, $CaPdBr_4$, $Na_2PdCl_4$, $Na_2PdBr_4$, $K_2PdCl_4$, $K_2PdBr_4$, $Na_2PdBr_4$, $CaPdCl_xBr_y$, $K_2PdBr_xCl_y$, $Na_2PdBr_xCl_y$ (where x is 3 if y is 1 and where x is 1 if y is 3), and mixtures thereof;
   Group 2: Molybdenum acids or salts selected from the group consisting of silicomolybdic acids, phosphomolybdic acids, soluble salts of silicomolybdic acids, soluble salts of phosphomolybdic acids, mixed heteropolymolybdates, and mixtures thereof;
   Group 3: Copper chloride, copper bromide, or mixtures thereof;

Group 4: Supramolecular complexing molecules selected from the group consisting of alpha cyclodextrins, beta cyclodextrins, and gamma cyclodextrins, and soluble derivatives thereof, and mixtures thereof;

Group 5: Soluble halide salts selected from the group consisting of $AlCl_3$, $AlBr_3$, $CdCl_2$, $CdBr_2$, $CoCl_2$, $CoBr_2$, $CeCl_3$, $CeBr_3$, $CrCl_3$, $CrBr_2$, $FeCl_3$, $FeBr_3$, $MnCl_2$, $MnBr_2$, $NiCl_2$, $NiBr_2$, $SrCl_2$, $SrBr_2$, $ZnCl_2$, $ZnBr_2$, $SnCl_2$, $SnBr_2$, $BaCl_2$, $BaCl_2$, $MgCl_2$, $MgBr_2$, and mixtures thereof;

Group 6: Organic solvents and co-solvents, trichloroacetic acid, trifluoroacetate, copper trifluoroacetylacetonate, and mixtures thereof;

Group 7: Soluble acids selected from the group consisting of hydrochloric acid, nitric acid, triflic acid, and mixtures thereof; and Group 8: Oxidizers selected from the group consisting of nitric acid, hydrogen peroxide, and mixtures thereof.

30. The system of claim 29, wherein the chemicals from Groups 1 through 8 are present in the mixture in the following molar ratios:
Group 1:Group 3=10.19:1:16.98:1;
Group 2:Group 3=3.04:1:5.07:1;
Group 4:Group 3=1.04:1:1.74:1;
Group 5:Group 3=34.11:1:56.84:1;
Group 6:Group 3=1.07:1:1.79:1;
Group 7:Group 3=0.004:1:0.04:1; and
Group 8:Group 3=0.04:1:0.08:1.

31. The system of claim 29, wherein the chemicals from Groups 1 through 8 are present in the mixture in the following molar ratios:
Group 2:Group 1=0.30:1:0.35:1;
Group 3:Group 1=0.10:1:4.75:1;
Group 4:Group 1=0.05:1:0.1:1;
Group 5:Group 1=1.75:1:2.92:1;
Group 6:Group 1=0.00:1:0.00:1;
Group 7:Group 1=0.62:1:1.03:1; and
Group 8:Group 1=0.70:1:1.16:1.

32. The system of claim 28, wherein the mixture is coated on the boron oxide coated substrate by soaking the boron oxide coated substrate in the mixture or by injecting the mixture into the boron oxide coated substrate.

33. The system of claim 1, wherein the substrate of the at least one sensor comprises a high surface area porous substrate comprising a material selected from the group consisting of porous silica, silica gel, silica xerogel, porous silica glass, and mixtures thereof.

34. The system of claim 33, wherein the high surface area porous substrate is a porous silica disk.

35. The system of claim 1, wherein the at least one sensor exhibits a first color when exposed to less than a threshold level of the target gas and the at least one sensor exhibits a second color when exposed to at least the threshold level of the target gas.

* * * * *

UNITED STATES PATENT AND TRADEMARK OFFICE
CERTIFICATE OF CORRECTION

| | |
|---|---|
| PATENT NO. | : 8,956,571 B2 |
| APPLICATION NO. | : 13/657776 |
| DATED | : February 17, 2015 |
| INVENTOR(S) | : Mark K. Goldstein et al. |

It is certified that error appears in the above-identified patent and that said Letters Patent is hereby corrected as shown below:

On the Title Page
(63) Related U.S. Application Data, line 3      Delete "13/565,327",
                                                Insert --13/565,627--

Signed and Sealed this
Sixteenth Day of August, 2016

Michelle K. Lee
*Director of the United States Patent and Trademark Office*